(12) United States Patent
Williams et al.

(10) Patent No.: US 11,897,952 B2
(45) Date of Patent: *Feb. 13, 2024

(54) MECHANICALLY INTERLOCKING COMPLEXES

(71) Applicant: City of Hope, Duarte, CA (US)

(72) Inventors: John Williams, Monrovia, CA (US); Krzysztof P. Bzymek, Pasadena, CA (US); David Horne, Altadena, CA (US); Jun Xie, Duarte, CA (US)

(73) Assignee: City of Hope

( * ) Notice: Subject to any disclaimer, the term of this patent is extended or adjusted under 35 U.S.C. 154(b) by 0 days.

This patent is subject to a terminal disclaimer.

(21) Appl. No.: 15/563,093

(22) PCT Filed: Mar. 30, 2016

(86) PCT No.: PCT/US2016/025066
§ 371 (c)(1),
(2) Date: Sep. 29, 2017

(87) PCT Pub. No.: WO2016/161018
PCT Pub. Date: Oct. 6, 2016

(65) Prior Publication Data
US 2018/0086826 A1    Mar. 29, 2018

Related U.S. Application Data

(60) Provisional application No. 62/140,345, filed on Mar. 30, 2015.

(51) Int. Cl.
C07K 16/28    (2006.01)
C07K 16/02    (2006.01)
(Continued)

(52) U.S. Cl.
CPC .............. C07K 16/02 (2013.01); C07K 7/06 (2013.01); C07K 7/08 (2013.01); C07K 14/7051 (2013.01);
(Continued)

(58) Field of Classification Search
None
See application file for complete search history.

(56) References Cited

U.S. PATENT DOCUMENTS 4,676,980 A    6/1987 Segal et al.
4,816,567 A    3/1989 Cabilly et al.
(Continued)

FOREIGN PATENT DOCUMENTS

EP    0173494 A2    3/1986
EP    0173494 A3    3/1986
(Continued)

OTHER PUBLICATIONS

Bzymek et al., Nature Communications, (2018) 9:1580 (Year: 2018).*

(Continued)

*Primary Examiner* — Karl J Puttlitz
(74) *Attorney, Agent, or Firm* — MINTZ LEVIN COHN FERRIS GLOVSKY AND POPEO, P.C.

(57) ABSTRACT

Provided herein are functionalized monoclonal antibodies (mAbs) including antibody fragments, including those where a Fab-binding molecule (Fab binding moiety) linked to a steric hindering molecule (steric hindering chemical moiety) is mechanically interlocked (e.g., through noncovalent conjugation) with the antibody or antibody fragment. Also provided are compositions that form highly stable and versatile drug delivery and diagnostic compositions.

12 Claims, 30 Drawing Sheets

Specification includes a Sequence Listing.

(51) Int. Cl.
C07K 7/06 (2006.01)
C07K 7/08 (2006.01)
C07K 14/725 (2006.01)
A61K 39/00 (2006.01)

(52) U.S. Cl.
CPC .... *C07K 16/2869* (2013.01); *A61K 2039/505* (2013.01); *A61K 2039/58* (2013.01); *A61K 2039/64* (2013.01); *C07K 2317/55* (2013.01); *C07K 2317/60* (2013.01); *C07K 2317/92* (2013.01); *C07K 2319/00* (2013.01); *C07K 2319/01* (2013.01)

(56) References Cited

U.S. PATENT DOCUMENTS

| | | |
|---|---|---|
| 4,861,760 A | 8/1989 | Mazuel et al. |
| 4,911,920 A | 3/1990 | Jani et al. |
| 4,946,778 A | 8/1990 | Ladner et al. |
| 5,212,162 A | 5/1993 | Missel et al. |
| 5,403,841 A | 4/1995 | Lang et al. |
| 5,530,101 A | 6/1996 | Queen et al. |
| 5,545,806 A | 8/1996 | Longberg et al. |
| 5,545,807 A | 8/1996 | Surani et al. |
| 5,569,825 A | 10/1996 | Longberg et al. |
| 5,585,089 A | 12/1996 | Queen et al. |
| 5,625,126 A | 4/1997 | Longberg et al. |
| 5,633,425 A | 5/1997 | Longberg et al. |
| 5,661,016 A | 8/1997 | Longberg et al. |
| 5,693,761 A | 12/1997 | Queen et al. |
| 5,777,085 A | 7/1998 | Co et al. |
| 5,859,205 A | 1/1999 | Adair et al. |
| 6,180,370 B1 | 1/2001 | Queen et al. |
| 6,210,671 B1 | 4/2001 | Co |
| 6,329,511 B1 | 12/2001 | Vasquez et al. |
| 2012/0177568 A1* | 7/2012 | Williams ........... A61K 47/6897 424/1.49 |
| 2012/0301400 A1 | 11/2012 | Williams et al. |
| 2014/0113348 A1 | 4/2014 | Williams et al. |

FOREIGN PATENT DOCUMENTS

| | | |
|---|---|---|
| JP | 2015-501299 A | 1/2015 |
| WO | WO 87/02671 A1 | 5/1987 |
| WO | WO-91/00360 A1 | 1/1991 |
| WO | WO-93/08829 A1 | 5/1993 |
| WO | 2013055404 * | 4/2013 |
| WO | WO-2013/055404 A1 | 4/2013 |

OTHER PUBLICATIONS

Bruns, C.J. et al. (2012). "The mechanical bond: a work of art," *Top Curr Chem* 323:19-72.

Donaldson, j.m. et al. (Oct. 22, 2013, e-published Oct. 7, 2013). "Identification and grafting of a unique peptide-binding site in the Fab framework of monoclonal antibodies," *PNAS USA* 110(43):17456-17461.

Gordon, C.G. et al. (Jun. 6, 2012, e-published May 24, 2012). "Reactivity of biarylazacyclooctynones in copper-free click chemistry," *J Am Chem Soc* 134(22):9199-9208.

International Search Report dated Aug. 12, 2016, for PCT Application No. PCT/US2016/025066, filed Mar. 30, 2016, 5 pages.

Jewett, J.C. et al. (Apr. 2010). "Cu-free click cycloaddition reactions in chemical biology," *Chem Soc Rev* 39(4):1272-1279.

Perez, H.L. et al. (Jul. 2014, e-published Nov. 15, 2013). "Antibody-drug conjugates: current status and future directions," *Drug Discov Today* 19(7):869-881.

Written Opinion dated Aug. 12, 2016, for PCT Application No. PCT/US2016/025066, filed Mar. 30, 2016, 7 pages.

* cited by examiner

FIG. 9
FIG. 9A
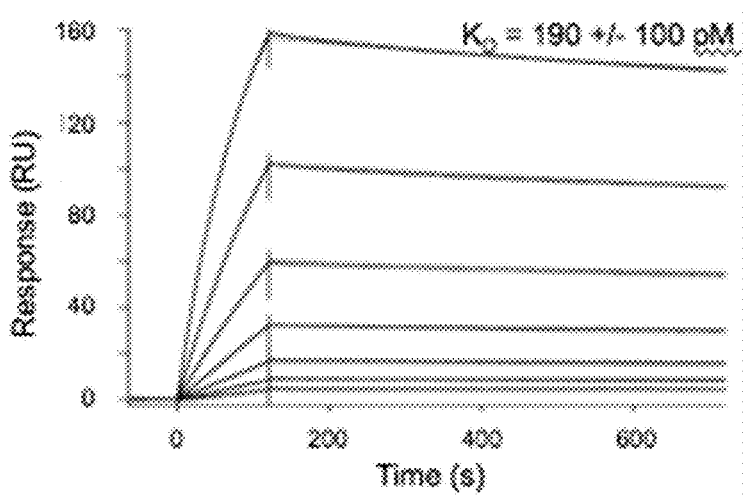
FIG. 9B
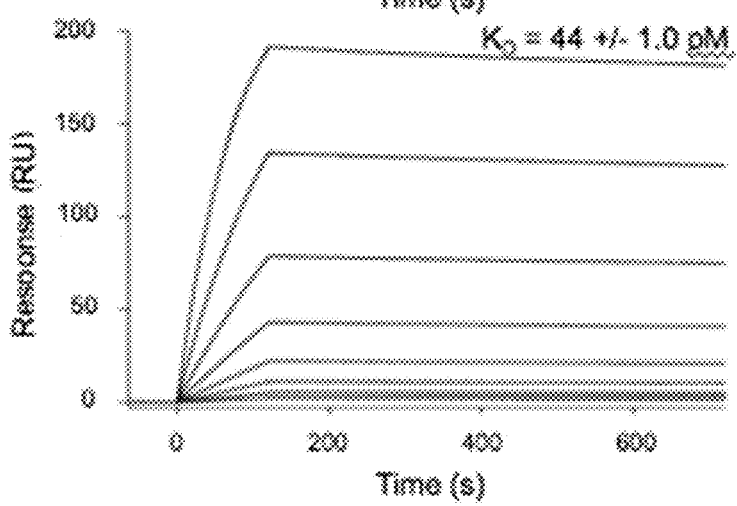
FIG. 9C
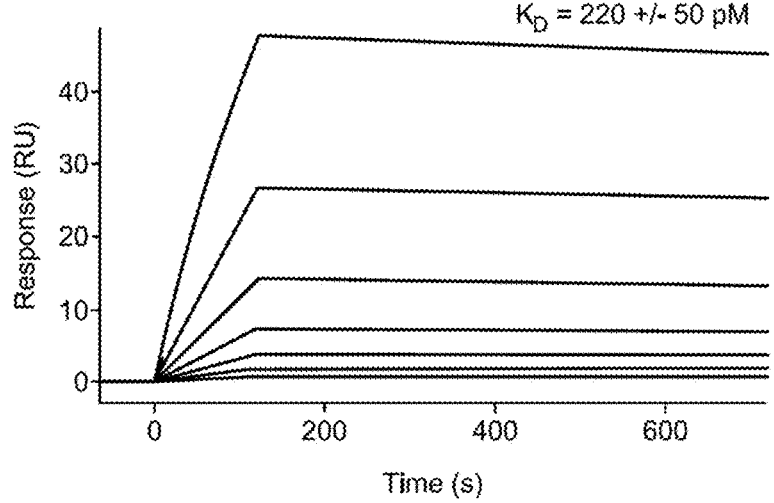

Meditope conjugate

Fab

MECHANICALLY INTERLOCKING COMPLEXES

CROSS-REFERENCE TO RELATED APPLICATIONS

This application is a U.S. National Phase Application of PCT Application No. PCT/US/2016/025066, filed Mar. 30, 2016, which claims the benefit of U.S. Provisional Application No. 62/140,345, filed Mar. 30, 2015, which are incorporated herein by reference in their entirety and for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 48440-561001WO_ST25.TXT, created Mar. 29, 2016, 4,727 bytes, machine format IBM-PC, MS-Windows operating system, is hereby incorporated by reference.

BACKGROUND OF THE INVENTION

Due to their specificity and favorable pharmacokinetics and pharmacodynamics, there have been substantial efforts to arm monoclonal antibodies (mAbs), either with potent cytotoxins or biologics to enhance their therapeutic efficacy or with radionuclides to image disease. These methods are limited by available chemistries of the parental mAb and/or require extensive protein engineering. The novel compositions and methods provided herein cure these and other deficiencies in the art.

BRIEF SUMMARY OF THE INVENTION

In one aspect, a mechanically interlocked complex is provided. The complex includes a compound mechanically interlocked with a fragment antigen-binding (Fab) domain. The Fab domain includes a hole within a central cavity lined by amino acid residues of the VH, VL, CH1, and CL regions of the Fab domain, wherein the central cavity includes a non-CDR binding site. The compound includes a Fab binding moiety attached to a steric hindering chemical moiety through a chemical linker, wherein the Fab binding moiety is bound to the non-CDR binding site, the chemical linker passes through the hole, and steric hindrance occurs between the steric hindering chemical moiety and amino acids lining the hole thereby mechanically interlocking the compound and the Fab.

In one aspect, a compound of formula:

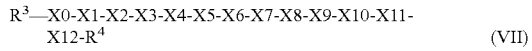
$$R^3\text{—X0-X1-X2-X3-X4-X5-X6-X7-X8-X9-X10-X11-X12-R}^4 \quad \text{(VII)}$$

is provided. In formula (VII) X0 is Ser or null. X1 is Cys, Ser, Gly, β-alanine, diaminopropionic acid, β-azidoalanine, or null. X2 is Gln or null. X3 is Phe, Tyr, β,β'-diphenyl-Ala, His, Asp, 2-bromo-L-phenylalanine, 3-bromo-Lphenylalanine, 4-bromo-L-phenylalanine, Asn, Gln, a modified Phe, a hydratable carbonyl-containing residue, or a boronic acid-containing residue. X4 is Asp or Asn. X5 is Leu; β,β'-diphenyl-Ala, Phe, Trp, Tyr, a non-natural analog of phenylalanine, tryptophan, or tyrosine, a hydratable carbonyl-containing residue, or a boronic acid-containing residue. X6 is Ser or Cys. X7 is Thr, Ser or Cys. X8 is an amino acid including a side chain of the formula $-L^{1.4}-L^1-R^2$, wherein $L^{1.4}$ is bond, —O—, —S—, —C(O)—, —C(O)O—, —C(O)NH—, —S(O)$_2$NH—, —NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene. X9 is Arg or Ala. X10 is Leu, Gln, Glu, β,β'-diphenyl-Ala, Phe, Trp, Tyr, a non-natural analog of phenylalanine, tryptophan, or tyrosine; a hydratable carbonyl-containing residue; or a boronic acid-containing residue. X11 is Lys or Arg. X12 is Cys, Gly, 7-aminoheptanoic acid, β-alanine, diaminopropionic acid, propargylglycine, isoaspartic acid, or null. $L^1$ is a chemical linker. $R^2$ is a steric hindering chemical moiety. $R^3$ and $R^4$ are independently null, $-L^2-R^5$ or an amino acid peptide sequence optionally substituted with $-L^2-R^5$, wherein $L^2$ is a covalent or non-covalent linker and $R^5$ is a therapeutic agent, a diagnostic agent, or a detectable agent, and wherein X1 and X12 are optionally joined together to form a cyclic peptidyl moiety.

In another aspect, a compound having the formula:

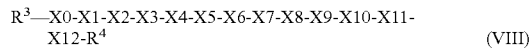
$$R^3\text{—X0-X1-X2-X3-X4-X5-X6-X7-X8-X9-X10-X11-X12-R}^4 \quad \text{(VIII)}$$

is provided. In formula (VIII) X0 is Ser or null. X1 is Cys, Ser, Gly, β-alanine, diaminopropionic acid, β-azidoalanine, or null. X2 is Gln or null. X3 is Phe, Tyr, β,β'-diphenyl-Ala, His, Asp, 2-bromo-L-phenylalanine, 3-bromo-Lphenylalanine, 4-bromo-L-phenylalanine, Asn, Gln, a modified Phe, a hydratable carbonyl-containing residue, or a boronic acid-containing residue. X4 is Asp or Asn. X5 is Leu; β,β'-diphenyl-Ala, Phe, Trp, Tyr, a non-natural analog of phenylalanine, tryptophan, or tyrosine; a hydratable carbonyl-containing residue, or a boronic acid-containing residue. X6 is Ser or Cys. X7 is Thr, Ser or Cys. X8 is an amino acid including a side chain of the formula $-L^{1.4}-L^1-R^6$, wherein $L^{1.4}$ is a bond, —O—, —S—, —C(O)—, —C(O)O—, —C(O)NH—, —S(O)$_2$NH—, —NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene. X9 is Arg or Ala. X10 is Leu, Gln, Glu; β,β'-diphenyl-Ala, Phe, Trp, Tyr, a non-natural analog of phenylalanine, tryptophan, or tyrosine, a hydratable carbonyl-containing residue, or a boronic acid-containing residue. X11 is Lys or Arg and X12 is Cys, Gly, 7-aminoheptanoic acid, β-alanine, diaminopropionic acid, propargylglycine, isoaspartic acid, or null. $L^1$ is a chemical linker. $R^3$ and $R^4$ are independently null, $-L^2-R^5$ or an amino acid peptide sequence optionally substituted with $-L^2-R^5$, wherein $L^2$ is a covalent or non-covalent linker and $R^5$ is a therapeutic agent, a diagnostic agent, or a detectable agent. $R^6$ is a click chemistry reactive functional group and wherein X1 and X12 are optionally joined together to form a cyclic peptidyl moiety.

In one aspect, a method of binding an antigen is provided. The method includes contacting an antigen with the mechanically interlocked complex provided herein including embodiments thereof and allowing said Fab to bind the antigen.

In another aspect, a method of forming a mechanically interlocked complex is provided. The method includes contacting the compound provided herein with a steric hindering chemical moiety including a complementary click chemistry reactive functional group. The complementary click chemistry reactive functional group is allowed to react with the click chemistry reactive functional group thereby forming a chemical linker between the steric hindering chemical moiety and the compound, wherein the chemical linker passes through the hole and steric hindrance occurs between the steric hindering chemical moiety and amino acids lining the hole thereby mechanically interlocking the compound and the Fab.

In another aspect, a method of forming a mechanically interlocked complex is provided. The method includes contacting a compound with a steric hindering chemical moiety. The steric hindering chemical moiety includes a complementary click chemistry reactive functional group and the compound includes a Fab binding moiety attached to a click chemistry reactive functional group. The Fab binding moiety is bound to a non-CDR binding site of a Fab domain, the Fab domain includes a hole within a central cavity lined by amino acid residues of the VH, VL, CH1, and CL regions of the Fab domain, wherein the central cavity includes the non-CDR binding site. The complementary click chemistry reactive functional group is allowed to react with the click chemistry reactive functional group thereby forming a conjugate including a steric hindering chemical moiety linked through a chemical linker to the Fab binding moiety, wherein the chemical linker passes through the hole and steric hindrance occurs between the steric hindering chemical moiety and amino acids lining the hole thereby mechanically interlocking the compound and the Fab.

BRIEF DESCRIPTION OF THE DRAWINGS

FIG. 2A) overall view of meditope bound to trastuzumab memAb. FIG. 2B) Close-up of Leu5 of original meditope bound to original trastuzumab memAB. FIG. 2C) Close-up of long 5-diphenylalanine meditope binding to original trastuzumab memAB. FIG. 2D) Close-up of 183 in the light chain of the original trastuzumab memAb. FIG. 2E) mutation of 183 to glutamate and its juxtaposition to Arg9 of the meditope. The corresponding surface plasmon resonance traces all collected at 37° C. are shown. A ~25 fold increase in the affinity by replacing Leu5 with 5-diphenylalanine in the meditope (top panels left to right, i.e. FIG. 2A, B, C) can be observed. We also observe a ~25 increase in mutating the 183 to glutamate (left panels top to bottom, i.e. FIG. 2A, D, E). The combination produces an 1160 fold increase in the overall affinity.

FIG. 3A-FIG. 3E: Schematic representation of mechanically interlocked meditopes. Copper-free click chemistry was used to effectively create an "infinite" affinity, non covalent meditope-Fab complex. Specifically, the guandinium group of arginine 8 is partially exposed to the opposing cavity of the fab "hole." An azide was threaded through hole through the modification of Arg8. This provides sufficient "space" for DIBO-Alexafluor, a strained cyclooctyne, to react cyclize with the azide. Establishing the interlocked meditope, it is now possible to envision multiple application of this invention. For instance, different cytotoxins (denoted $R_1$) can be conjugated to the clickable meditope. Similarly, other functionalities including imaging agents, cytotoxins, biologics (denoted $R_2$) can be conjugated to DIBO. Mixing different members will give a unique combination. For instance, if there are 10 members of $R_1$ and 10 members of $R_2$, it is possible to create 100 unique, interlocked-Fab combinations. FIG. 3F: Azide meditope binds with high affinity. SPR was used to demonstrate that modified meditope binds to I83E-trastuzumab memab (on chip) with high affinity.

FIGS. 9A-9C: Mechanically interlocked meditope does not affect antigen binding. SPR sensograms comparing the binding interactions of memAb trastuzumab Fab variants FIG. 9A) I83F, FIG. 9B) I83E and FIG. 9C) I83E: rivetope/PEG30K to immobilized HER2 at 25° C. The calculated $K_D$ values are 190+/−100 pM, 44+/−1.0 pM and 220+/−50 pM respectively.

FIG. 15A: Calculated molecular weight 1160.3. FIG. 15B: Mass spectrometry analysis of 8-azido-5-diphenyl-meditope. Calculated molecular weight 2133.0. FIG. 15C: Mass spectrometry analysis of conjugate between 8-azido-5-diphenyl-meditope and DIBO-AlexaFluor647. Calculated molecular weight 3293.3. FIG. 15D top panel: meditope enabled Trastuzumab IgG with interlocked 8-azido-5-diphenyl-meditope-DIBO-AlexaFluor647. FIG. 15D bottom: mass spectroscopy analysis of meditope enabled Trastuzumab IgG. Two additional peaks can be noticed in the top panel shifted by approx. 3.2 kDa and 6.5 kDa with respect to unreacted IgG, corresponding to 2 molecules of interlocked meditope.

FIG. 17A: A high affinity meditope (bolt) was locked on with an Alexafluor647 alkyne (nut) and used to imaging tumor bearing animals (left and middle) and non-tumor bearing (right) 48 hours after tail vein injection. FIG. 17B The major organs were harvested 8 days later and imaged. The fluorophore accumulated and remained in the tumor. The presence of the fluorophone was not detectable in the liver, kidneys or spleen.

DETAILED DESCRIPTION OF THE INVENTION

Definitions

Figure 1:
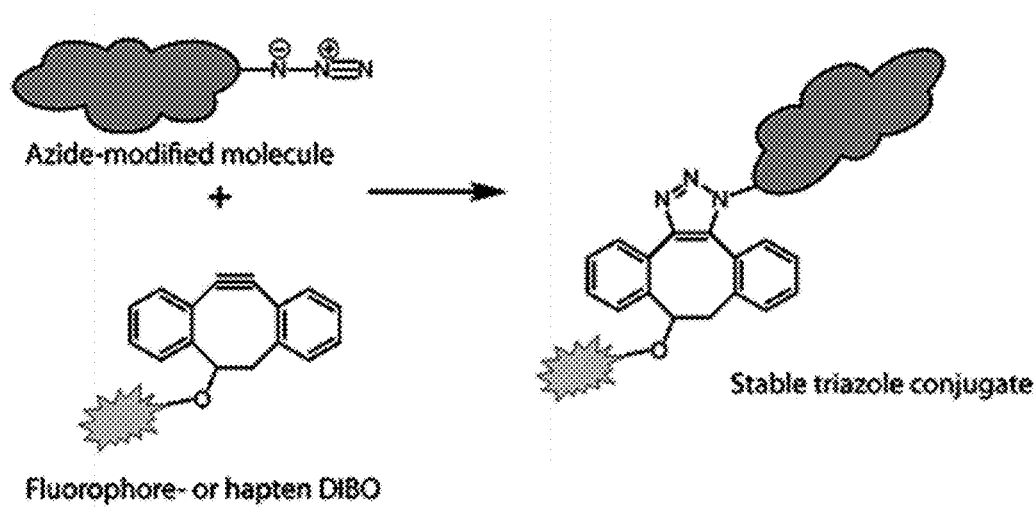
FIG. 1: Schematic representation of mechanical bond formation. Reaction conditions: I83E Fab or IgG present at 100 µM; 5-diphenyl-8-Arg-(PEG)-$N_3$ present at 150 µM (for Fab) or 300 µM (for IgG); Alexa647-DIBO (diphenylcyclooctyne) present at 300 µM (for Fab) or 800 µM (for IgG).
Figure 2A:
FIGS. 2A-2E: SPR sensograms and crystal structures of meditope peptide variants binding to immobilized meditope-enabled antibody variants.
Figure 2B:
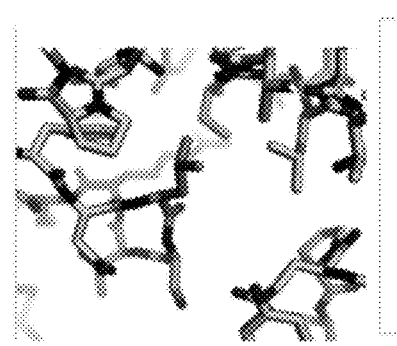
Figure 2C:
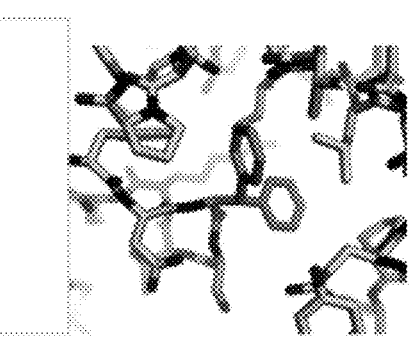
Figures 2D, 2E:
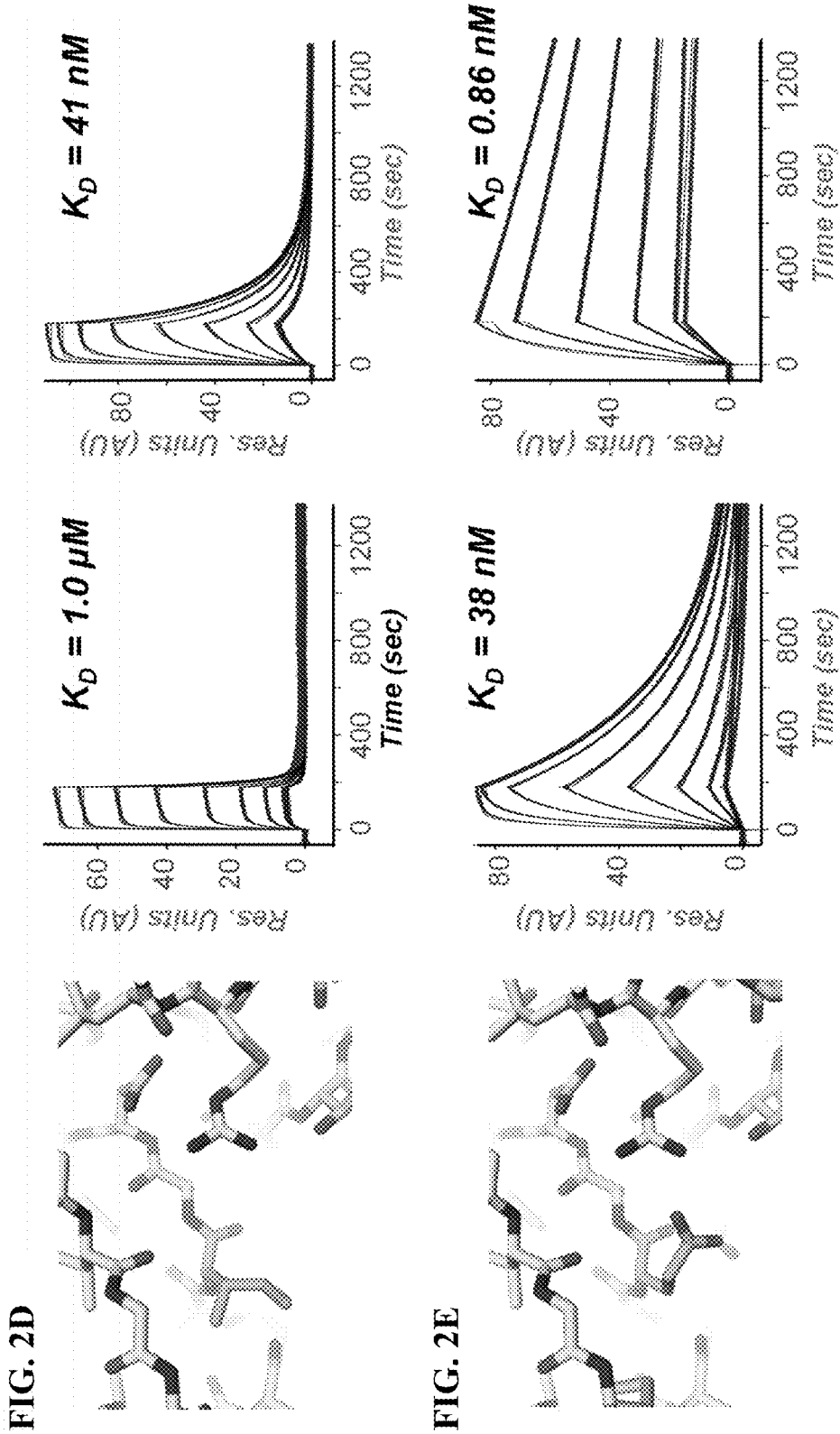

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated.

The term "alkylene," by itself or as part of another substituent, means, unless otherwise stated, a divalent radical derived from an alkyl, as exemplified, but not limited by, —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable non-cyclic straight or branched chain, or combinations thereof, including at least one carbon atom and at least one heteroatom (e.g. O, N, P, Si or S) and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'-represents both —C(O)$_2$R'- and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl,", "cycloalkyl", "heterocycloalkyl", "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R")=NR''', —S(O)R', —S(O)$_2$R', —S(O)$_2$N(R)('R"—NRSO$_2$R'), —CN, and —NO$_2$ in a number ranging from zero to (2m'+1), where m' is the total number of carbon atoms in such radical. R', R", R''', and R'''' each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R''', and R'''' group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R''', —OC(O)R', —C(O)R', —CO$_2$R', —CONR'R", —OC(O)NR'R", —NR"C(O)R', —NR'—C(O)NR"R''', NR"C(O)$_2$R', NRC(NR'R")=NR''', S(O)R', —S(O)$_2$R', —S(O)$_2$N(R')(R", —NRSO$_2$R'), —CN, —NO$_2$, —R', —N$_3$, —CH(Ph)$_2$, fluoro(C$_1$-C$_4$)alkoxy, and fluoro (C$_1$-C$_4$)alkyl, in a number ranging from zero to the total number of open valences on the aromatic ring system; and where R', R", R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R''', and R'''' groups when more than one of these groups is present.

Where a moiety is substituted with an R substituent, the group may be referred to as "R-substituted." Where a moiety is R-substituted, the moiety is substituted with at least one R substituent and each R substituent is optionally different. For example, where a moiety herein is R$^1$A-substituted or unsubstituted alkyl, a plurality of R$^{14}$ substituents may be attached to the alkyl moiety wherein each R$^{14}$ substituent is optionally different. Where an R-substituted moiety is substituted with a plurality R substituents, each of the R-substituents may be differentiated herein using a prime symbol (') such as R', R", etc. For example, where a moiety is R$^1$A-substituted or unsubstituted alkyl, and the moiety is substituted with a plurality of R$^{14}$ substituents, the plurality of R$^{14}$ substituents may be differentiated as R$^{14'}$, R$^{14''}$, R$^{14'''}$, etc. In some embodiments, the plurality of R substituents is 3. In some embodiments, the plurality of R substituents is 2.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C"R"R''')$_d$—, where variables s and d are independently integers of from 0 to 3, and X is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)

NH$_2$, —NHSO$_2$H, —NHC═(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
  (ii) alkyl, heteroalkyl, cycloalkyl, heterocycloalkyl, aryl, heteroaryl, substituted with at least one substituent selected from:
    (a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
    (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NH$_4$NH$_2$, —NHC═(O) NH$_2$, —NHSO$_2$H, —NHC═(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, each substituted or unsubstituted heterocycloalkyl is a substituted or unsubstituted 3 to 8 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, each substituted or unsubstituted heterocycloalkylene is a substituted or unsubstituted 3 to 8 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, each substituted or unsubstituted heterocycloalkyl is a substituted or unsubstituted 3 to 7 membered heterocycloalkyl, each substituted or unsubstituted aryl is a substituted or unsubstituted C$_6$-C$_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted cycloalkylene is a substituted or unsubstituted C$_3$-C$_7$ cycloalkylene, each substituted or unsubstituted heterocycloalkylene is a substituted or unsubstituted 3 to 7 membered heterocycloalkylene, each substituted or unsubstituted arylene is a substituted or unsubstituted C$_6$-C$_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

As used herein, the term "conjugate" refers to the association between atoms or molecules. The association can be direct or indirect. For example, a conjugate between a nucleic acid and a protein can be direct, e.g., by covalent bond, or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the microparticle is non-covalently attached to solid support through a non-covalent chemical reaction between a component of the microparticle and a component of solid support. In other embodiments, the microparticle includes one or more reactive moieties, e.g., a covalent reactive moiety, as described herein (e.g., an amine reactive moiety). In other embodiments, the microparticle includes a linker with one or more reactive moieties, e.g., a covalent reactive moiety, as described herein (e.g., an amine reactive moiety).

Useful reactive moieties or functional groups used for conjugate chemistries (including "click chemistries" as known in the art) herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold;

(h) amine or sulfhydryl groups, which can be, for example, acylated, alkylated or oxidized;

(i) alkenes, which can undergo, for example, cycloadditions, acylation, Michael addition, etc.;

(j) epoxides, which can react with, for example, amines and hydroxyl compounds;

(k) phosphoramidites and other standard functional groups useful in nucleic acid synthesis;

(l) metal silicon oxide bonding;

(m) metal bonding to reactive phosphorus groups (e.g. phosphines) to form, for example, phosphate diester bonds; and (n) sulfones, for example, vinyl sulfone.

Chemical synthesis of compositions by joining small modular units using conjugate ("click") chemistry is well known in the art and described, for example, in H. C. Kolb, M. G. Finn and K. B. Sharpless ((2001). "Click Chemistry: Diverse Chemical Function from a Few Good Reactions". Angewandte Chemie International Edition 40 (11): 2004-2021); R. A. Evans ((2007). "The Rise of Azide-Alkyne 1,3-Dipolar 'Click' Cycloaddition and its Application to Polymer Science and Surface Modification". Australian Journal of Chemistry 60 (6): 384-395; W. C. Guida et al. Med. Res. Rev. p 3 1996; Spiteri, Christian and Moses, John E. ((2010). "Copper-Catalyzed Azide-Alkyne Cycloaddition: Regioselective Synthesis of 1,4,5-Trisubstituted 1,2,3-Triazoles". Angewandte Chemie International Edition 49 (1): 31-33); Hoyle, Charles E. and Bowman, Christopher N. ((2010). "Thiol-Ene Click Chemistry". Angewandte Chemie International Edition 49 (9): 1540-1573); Blackman, Melissa L. and Royzen, Maksim and Fox, Joseph M. ((2008). "Tetrazine Ligation: Fast Bioconjugation Based on Inverse-Electron-Demand Diels-Alder Reactivity". Journal of the American Chemical Society 130 (41): 13518-13519); Devaraj, Neal K. and Weissleder, Ralph and Hilderbrand, Scott A. ((2008). "Tetrazine Based Cycloadditions: Application to Pretargeted Live Cell Labeling". Bioconjugate Chemistry 19 (12): 2297-2299); Stöckmann, Henning; Neves, Andre; Stairs, Shaun; Brindle, Kevin; Leeper, Finian ((2011). "Exploring isonitrile-based click chemistry for ligation with biomolecules". Organic & Biomolecular Chemistry), all of which are hereby incorporated by reference in their entirety and for all purposes.

The reactive functional groups can be chosen such that they do not participate in, or interfere with, the chemical stability of the proteins or nucleic acids described herein. By way of example, the nucleic acids can include a vinyl sulfone or other reactive moiety (e.g., maleimide). Optionally, the nucleic acids can include a reactive moiety having the formula —S—S—R. R can be, for example, a protecting group. Optionally, R is hexanol. As used herein, the term hexanol includes compounds with the formula $C_6H_{13}OH$ and includes, 1-hexanol, 2-hexanol, 3-hexanol, 2-methyl-1-pentanol, 3-methyl-1-pentanol, 4-methyl-1-pentanol, 2-methyl-2-pentanol, 3-methyl-2-pentanol, 4-methyl-2-pentanol, 2-methyl-3-pentanol, 3-methyl-3-pentanol, 2,2-dimethyl-1-butanol, 2,3-dimethyl-1-butanol, 3,3-dimethyl-1-butanol, 2,3-dimethyl-2-butanol, 3,3-dimethyl-2-butanol, and 2-ethyl-1-butanol. Optionally, R is 1-hexanol.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

The symbol "" denotes the point of attachment of a chemical moiety to the remainder of a molecule or chemical formula.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "CTLA-4" or "CTLA-4 protein" as provided herein includes any of the recombinant or naturally-occurring forms of the cytotoxic T-lymphocyte-associated protein 4 (CTLA-4) or variants or homologs thereof that maintain CTLA-4 protein activity (e.g. within at least 50%, 80%, 90%, 95%, 96%, 97%, 98%, 99% or 100% activity compared to CTLA-4). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring CTLA-4 polypeptide. In embodiments, CTLA-4 is the protein as identified by the NCBI sequence reference GI:83700231, homolog or functional fragment thereof.

The term "EGFR" or "EGFR protein" as provided herein includes any of the recombinant or naturally-occurring forms of the epidermal growth factor receptor (EGFR) is the or variants or homologs thereof that maintain EGFR activity (e.g. within at least 50%, 80%, 90%, 95%, 96%, 97%, 98%, 99% or 100% activity compared to EGFR). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring EGFR. In embodiments, EGFR is the protein as identified by the NCBI sequence reference GI: 29725609, homolog or functional fragment thereof.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, NY 1994); Sambrook et al., MOLECULAR CLONING, A LABORATORY MANUAL, Cold Springs Harbor Press (Cold Springs Harbor, N Y 1989). Any methods, devices and materials similar or equivalent to those described herein can be used in the practice of this invention. The following definitions are provided to facilitate understanding of certain terms used frequently herein and are not meant to limit the scope of the present disclosure.

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

A "cell" as used herein, refers to a cell carrying out metabolic or other functions sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., *Spodoptera*) and human cells. Cells may be useful when they are naturally nonadherent or have been treated not to adhere to surfaces, for example by trypsinization.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

The term "peptidyl" and "peptidyl moiety" means a peptide attached to the remainder of the molecule (e.g. -$L^1$-$R^2$). A peptidyl moiety may be substituted with a chemical linker (e.g., (for example, $L^{1.4}$, $L^3$) that serves to attach the peptidyl moiety to the remainder of the molecule (e.g., compound provided herein). The peptidyl moiety may also be substituted with additional chemical moieties (e.g. $R^3$ and/or $R^4$). The peptidyl moiety may also be substituted with an additional mechanically interlocked complex or a masking peptide moiety.

A "label" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

A "labeled protein or polypeptide" is one that is bound, either covalently, through a linker or a chemical bond, or noncovalently, through ionic, van der Waals, electrostatic, or hydrogen bonds to a label such that the presence of the labeled protein or polypeptide may be detected by detecting the presence of the label bound to the labeled protein or polypeptide. Alternatively, methods using high affinity interactions may achieve the same results where one of a pair of binding partners binds to the other, e.g., biotin, streptavidin.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that may be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence. An amino acid residue in a protein "corresponds" to a given residue when it occupies the same essential structural position within the protein as the given residue. For example, a selected residue in a selected antibody (or Fab domain) corresponds to light chain threonine at Kabat position 40, when the selected residue occupies the same essential spatial or other structural relationship as a light chain threonine at Kabat position 40. In some embodiments, where a selected protein is aligned for maximum homology with the light chain of an antibody (or Fab domain), the position in the aligned selected protein aligning with threonine 40 is said to correspond to threonine 40. Instead of a primary sequence alignment, a three dimensional structural alignment can also be used, e.g., where the structure of the selected protein is aligned for maximum correspondence with the light chain threonine at Kabat position 40, and the overall structures compared. In this case, an amino acid that occupies the same essential position as threonine 40 in the structural model is said to correspond to the threonine 40 residue.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids sequences encode any given amino acid residue. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acid as used herein also refers to nucleic acids that have the same basic chemical structure as a naturally occurring nucleic acid. Such analogues have modified sugars and/or modified ring substituents, but retain the same basic chemical structure as the naturally occurring nucleic acid. A nucleic acid mimetic refers to chemical compounds that have a structure that is different the general chemical structure of a nucleic acid, but that functions in a manner similar to a naturally occurring nucleic acid. Examples of such analogues include, without limitation, phosphorothiolates, phosphoramidates, methyl phosphonates, chiral-methyl phosphonates, 2-O-methyl ribonucleotides, and peptide-nucleic acids (PNAs).

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length. The present invention includes polypeptides that are substantially identical to any of SEQ ID NOs:1-20.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J. Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J Mol. Biol.* 215:403-410, respectively.

Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Nat. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Nat. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross-reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "modulation", "modulate", or "modulator" are used in accordance with their plain ordinary meaning and refer to the act of changing or varying one or more properties. "Modulator" refers to a composition that increases or decreases the level of a target molecule or the function of a target molecule or the physical state of the target of the molecule. "Modulation" refers to the process of changing or varying one or more properties. For example, as applied to the effects of a modulator on a biological target, to modulate means to change by increasing or decreasing a property or function of the biological target or the amount of the biological target.

As defined herein, the term "inhibition", "inhibit", "inhibiting" and the like in reference to a protein-inhibitor (e.g. antagonist) interaction means negatively affecting (e.g. decreasing) the activity or function of the protein relative to the activity or function of the protein in the absence of the inhibitor. In embodiments inhibition refers to reduction of a disease or symptoms of disease. Thus, in embodiments, inhibition includes, at least in part, partially or totally blocking stimulation, decreasing, preventing, or delaying activation, or inactivating, desensitizing, or down-regulating signal transduction or enzymatic activity or the amount of a protein.

As defined herein, the term "activation", "activate", "activating" and the like in reference to a protein-activator (e.g. agonist) interaction means positively affecting (e.g. increasing) the activity or function of the relative to the activity or function of the protein in the absence of the activator (e.g. composition described herein). Thus, in embodiments, activation may include, at least in part, partially or totally increasing stimulation, increasing or enabling activation, or activating, sensitizing, or up-regulating signal transduction or enzymatic activity or the amount of a protein decreased in a disease.

The term "recombinant" when used with reference, for example, to a cell, a nucleic acid, a protein, or a vector, indicates that the cell, nucleic acid, protein or vector has been modified by or is the result of laboratory methods. Thus, for example, recombinant proteins include proteins produced by laboratory methods. Recombinant proteins can include amino acid residues not found within the native (non-recombinant) form of the protein or can be include amino acid residues that have been modified, e.g., labeled.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody plays a significant role in determining the specificity and affinity of binding. In some embodiments, antibodies or fragments of antibodies may be derived from different organisms, including humans, mice, rats, hamsters, camels, etc. Antibodies of the invention may include antibodies that have been modified or mutated at one or more amino acid positions to improve or modulate a desired function of the antibody (e.g. glycosylation, expression, antigen recognition, effector functions, antigen binding, specificity, etc.).

Antibodies are large, complex molecules (molecular weight of ~150,000 or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region involved in binding the target antigen, and a constant ("C") region that interacts with other components of the immune system. The light and heavy chain variable regions come together in 3-dimensional space to form a variable region that binds the antigen (for example, a receptor on the surface of a cell). Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-dimensional space to form the actual antibody binding site which docks onto the target antigen. The position and length of the CDRs have been precisely defined by Kabat, E. et al., Sequences of Proteins of Immunological Interest, U.S. Department of Health and Human Services, 1983, 1987. The part of a variable region not contained in the CDRs is called the framework ("FR"), which forms the environment for the CDRs.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. The Fc (i.e. fragment crystallizable region) is the "base" or "tail" of an immunoglobulin and is typically composed of two heavy chains that contribute two or three constant domains depending on the class of the antibody. By binding to specific proteins the Fc region ensures that each antibody generates an appropriate immune response for a given antigen. The Fc region also binds to various cell receptors, such as Fc receptors, and other immune molecules, such as complement proteins.

Antibodies exist, for example, as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH—CH1 by a disulfide bond. The F(ab)'2 may be reduced under mild conditions to break the disulfide linkage in the hinge region, thereby converting the F(ab)'2 dimer into an Fab' monomer. The Fab' monomer is essentially the antigen binding portion with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

A single-chain variable fragment (scFv) is typically a fusion protein of the variable regions of the heavy (VH) and light chains (VL) of immunoglobulins, connected with a short linker peptide of 10 to about 25 amino acids. The linker may usually be rich in glycine for flexibility, as well as serine or threonine for solubility. The linker can either connect the N-terminus of the VH with the C-terminus of the VL, or vice versa.

The epitope of a mAb is the region of its antigen to which the mAb binds. Two antibodies bind to the same or overlapping epitope if each competitively inhibits (blocks) binding of the other to the antigen. That is, a 1×, 5×, 10×, 20× or 100× excess of one antibody inhibits binding of the other by at least 30% but preferably 50%, 75%, 90% or even 99% as measured in a competitive binding assay (see, e.g., Junghans et al., Cancer Res. 50:1495, 1990). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

For preparation of suitable antibodies of the invention and for use according to the invention, e.g., recombinant, monoclonal, or polyclonal antibodies, many techniques known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3rd ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676,980, WO 91/00360; WO 92/200373; and EP 03089).

Methods for humanizing or primatizing non-human antibodies are well known in the art (e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) Nature 321:522; and Verhoyen et al. (1988) Science 239:1534). Humanized antibodies are further described in, e.g., Winter and Milstein (1991) Nature 349:293. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Morrison et al., PNAS USA, 81:6851-6855 (1984), Jones et al., Nature 321:522-525 (1986); Riechmann et al., Nature 332:323-327 (1988); Morrison and Oi, Adv. Immunol., 44:65-92 (1988), Verhoeyen et al., Science 239:1534-1536 (1988) and Presta, Curr. Op. Struct. Biol. 2:593-596 (1992), Padlan, Molec. Immun., 28:489-498 (1991); Padlan, Molec. Immun., 31(3):169-217 (1994)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. For example, polynucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well known procedures from a variety of human cells.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

A "therapeutic antibody" as provided herein refers to any antibody or functional fragment thereof that is used to treat cancer, autoimmune diseases, transplant rejection, cardiovascular disease or other diseases or conditions such as those described herein. Non-limiting examples of therapeutic antibodies include murine antibodies, murinized or humanized chimera antibodies or human antibodies including, but not limited to, Erbitux (cetuximab), ReoPro (abciximab), Simulect (basiliximab), Remicade (infliximab); Orthoclone OKT3 (muromonab-CD3); Rituxan (rituximab), Bexxar (tositumomab) Humira (adalimumab), Campath (alemtuzumab), Simulect (basiliximab), Avastin (bevacizumab), Cimzia (certolizumab pegol), Zenapax (daclizumab), Soliris (eculizumab), Raptiva (efalizumab), Mylotarg (gemtuzumab), Zevalin (ibritumomab tiuxetan), Tysabri (natalizumab), Xolair (omalizumab), Synagis (palivizumab), Vectibix (panitumumab), Lucentis (ranibizumab), and Herceptin (trastuzumab).

Techniques for conjugating therapeutic agents to antibodies are well known (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery ($2^{nd}$ Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)). As used herein, the term "antibody-drug conjugate" or "ADC" refers to a therapeutic agent conjugated or otherwise covalently bound to an antibody. A "therapeutic agent" as referred to herein, is a composition useful in treating or preventing a disease such as cancer.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions typically requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity). protein).

A "ligand" refers to an agent, e.g., a polypeptide or other molecule, capable of binding to a receptor.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be, for example, a compound as described herein and a steric hindering chemical moiety. In embodiments contacting includes, for example, allowing a compound described herein to interact with a steric hindering chemical moiety.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

"Patient" or "subject in need thereof" refers to a living organism suffering from or prone to a disease or condition that can be treated by administration of a composition or pharmaceutical composition as provided herein. Non-limiting examples include humans, other mammals, bovines, rats, mice, dogs, monkeys, goat, sheep, cows, deer, and other non-mammalian animals. In some embodiments, a patient is human.

The terms "disease" or "condition" refer to a state of being or health status of a patient or subject capable of being treated with a compound, pharmaceutical composition, or method provided herein. In embodiments, the disease is cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma).

The terms "treating", or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, include prevention of an injury, pathology, condition, or disease. In embodiments, "treating" refers to treatment of cancer.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "therapeutically effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

As used herein, the term "cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g., hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound, pharmaceutical composition, or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound, pharmaceutical composition, or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound, pharmaceutical composition, or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound, pharmaceutical composition, or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, ductal carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatinifori carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lobular carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tubular carcinoma, tuberous carcinoma, verrucous carcinoma, or carcinoma villosum.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

"Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer.

The term "associated" or "associated with" in the context of a substance or substance activity or function associated with a disease (e.g., diabetes, cancer (e.g. prostate cancer, renal cancer, metastatic cancer, melanoma, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma)) means that the disease (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma) is caused by (in whole or in part), or a symptom of the disease is caused by (in whole or in part) the substance or substance activity or function.

"Chemotherapeutic" or "chemotherapeutic agent" is used in accordance with its plain ordinary meaning and refers to a chemical composition or compound having antineoplastic properties or the ability to inhibit the growth or proliferation of cells.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by using a method as described herein), results in reduction of the disease or one or more disease symptoms.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances, and the like., that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

By "co-administer" it is meant that a composition described herein is administered at the same time, just prior to, or just after the administration of one or more additional therapies. The compound of the invention can be administered alone or can be co-administered to the patient. Co-administration is meant to include simultaneous or sequential administration of the compound individually or in combination (more than one compound or agent). Thus, the preparations can also be combined, when desired, with other active substances (e.g. to reduce metabolic degradation).

The compositions disclosed herein can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions disclosed herein can also be delivered as microspheres for slow release in the body. For example, microspheres can be administered via intradermal injection of drug-containing microspheres, which slowly release subcutaneously (see Rao, *J. Biomater Sci. Polym.* Ed. 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J Microencapsul.* 13:293-306, 1996; Chonn, *Curr. Opin. Biotechnol.* 6:698-708, 1995; Ostro, *Am. J Hosp. Pharm.* 46:1576-1587, 1989). The compositions can also be delivered as nanoparticles.

Pharmaceutical compositions may include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule, and/or reducing, eliminating, or slowing the progression of disease symptoms.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

Complexes

Provided herein, are compositions and methods useful, inter alia, for the delivery of agents to a site or cell (e.g. imaging, therapeutic and/or diagnostic agents). The compositions provided herein include without limitation, functionalized monoclonal antibodies (mAbs) or antibody fragments, where a Fab-binding molecule (Fab binding moiety) linked to a steric hindering molecule (steric hindering chemical moiety) is mechanically interlocked (e.g., through noncovalent conjugation) with the antibody or antibody fragment. In some embodiments, the steric hindering molecule provides for enhanced binding affinity between the Fab-binding molecule and the Fab region of the antibody or antibody fragment. The linker connecting the Fab binding molecule and the steric hindering molecule may be a linker formed through conjugate (e.g. "click") chemistry. A large variety of diagnostic and therapeutic moieties and combinations thereof may be conjugated to the Fab-binding molecule and/or the steric hindering chemical moiety, thereby, providing for highly stable and/or versatile drug delivery and/or diagnostic compositions.

In one aspect, a mechanically interlocked complex is provided. The complex includes a compound mechanically interlocked with a fragment antigen-binding (Fab) domain. The Fab domain includes a hole within a central cavity, lined by amino acid residues of the VH, VL, CH1, and CL regions of the Fab domain, wherein the central cavity includes a non-CDR binding site. The compound includes a Fab binding moiety attached to a steric hindering chemical moiety, through a chemical linker, wherein the Fab binding moiety is bound to the non-CDR binding site, the chemical linker passes through the hole, and steric hindrance occurs between the steric hindering chemical moiety and amino acids lining the hole, thereby mechanically interlocking the compound and the Fab.

The term "mechanically interlocked complex" as provided herein refers to a complex of molecules which are connected at least in part as a consequence of their topology. On the molecular level, the mechanical interlocking of two or more separate components may be accomplished through non-covalent, mechanical means that significantly decrease dissociation of the two or more separate components. The mechanical means is accomplished through steric hindrance (e.g. by using a steric hindering chemical moiety). Thus, interlocked molecules cannot be separated without significant distortion of the covalent bonds that make up the conjoined molecules. Examples of mechanically interlocked molecular architectures include catenanes, rotaxanes, molecular knots, and molecular Borromean rings. In embodiments, the mechanically interlocked complex includes a Fab domain, a Fab binding moiety (e.g., a peptidyl moiety) attached to a steric hindering chemical moiety (e.g., substituted or unsubstituted —$R^2$) through a chemical linker (e.g., -$L^1$-).

A "fragment antigen-binding (Fab) domain" as referred to herein is a region on an antibody that binds to an antigen. As discussed above, the Fab domain is generally composed of one constant and one variable domain of each of the heavy and the light chain (VL, VH, CL and CH1, respectively). The paratope or antigen-binding site is formed on the N-terminus of the Fab domain. The two variable domains of a Fab domain typically bind the epitope on an antigen. In embodiments, the Fab domain forms part of an antibody. In embodiments, the Fab domain forms part of a therapeutic antibody.

Figure 19:
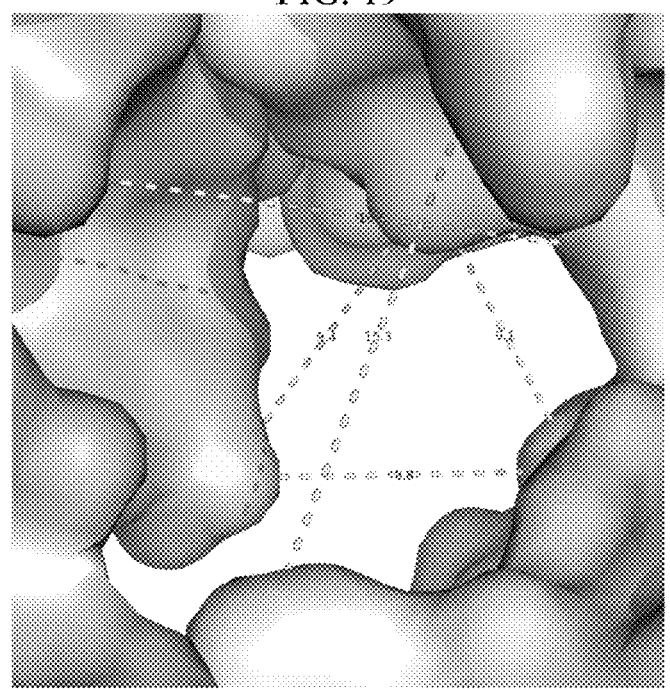
FIG. 19: Closer view of inner cavity with the hole shown in FIG. 18.
Figure 20:
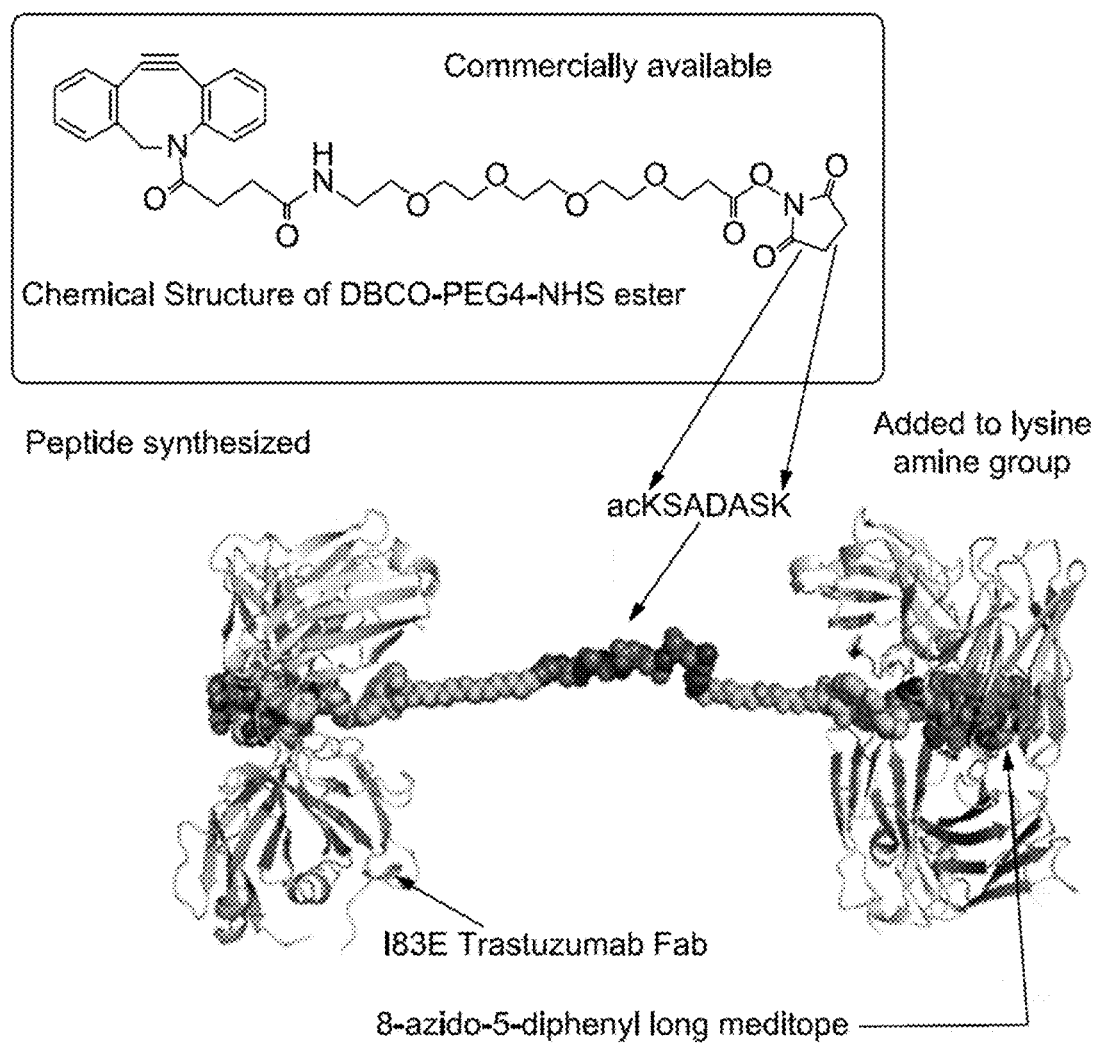
FIG. 20: Cartoon of a molecular dumbells. Applicants isolated a meditope-enabled Fab, added an azido meditope to the Fab, and then added a bis-peptydic DBCO (1:1:1/2 stoichiometry)
Figure 21:
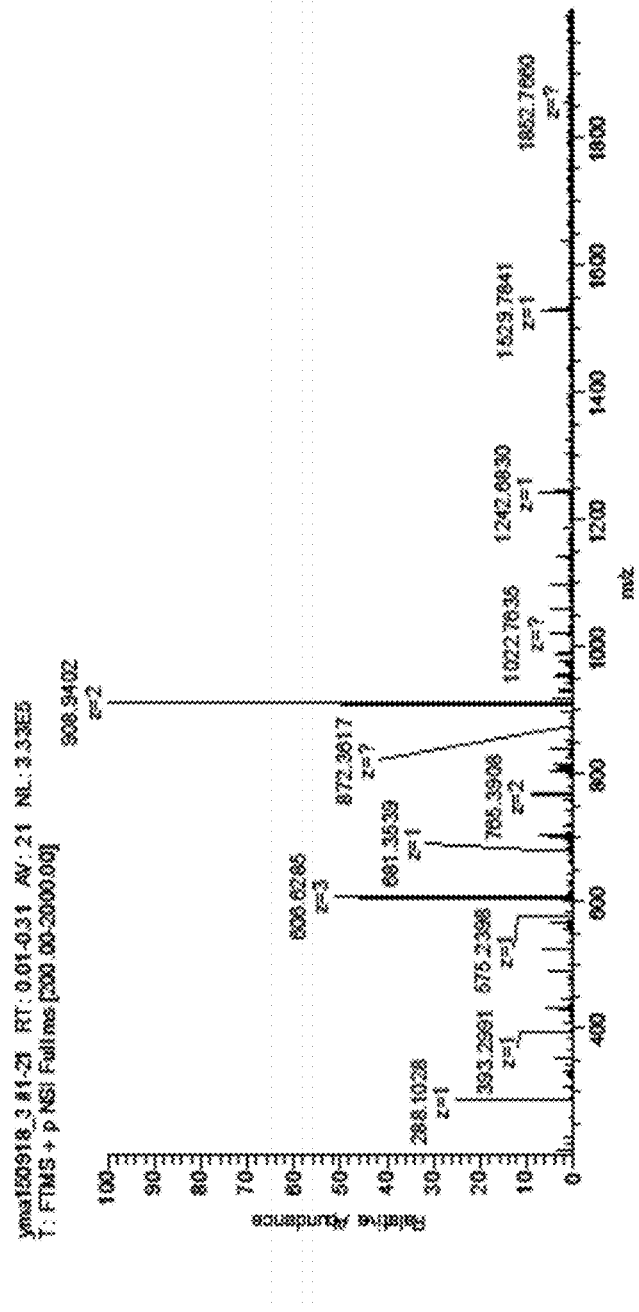
FIG. 21: To specifically control the distance between the two Fab arms, Applicants turned to a peptide. Peptides can be readily synthesized or biosynthesized, and the precise length controlled during synthesis. Moreover, coupling functional groups (e.g., DBCO) to the amine of lysine is well described/understood. For POC, a short peptide sequence with two lysines was synthesized. To ensure the N-terminal amide is not modified, the peptide was acetylated. The the mass spectrum indicting of the peptide indicated in the upper left is shown.
Figure 22:
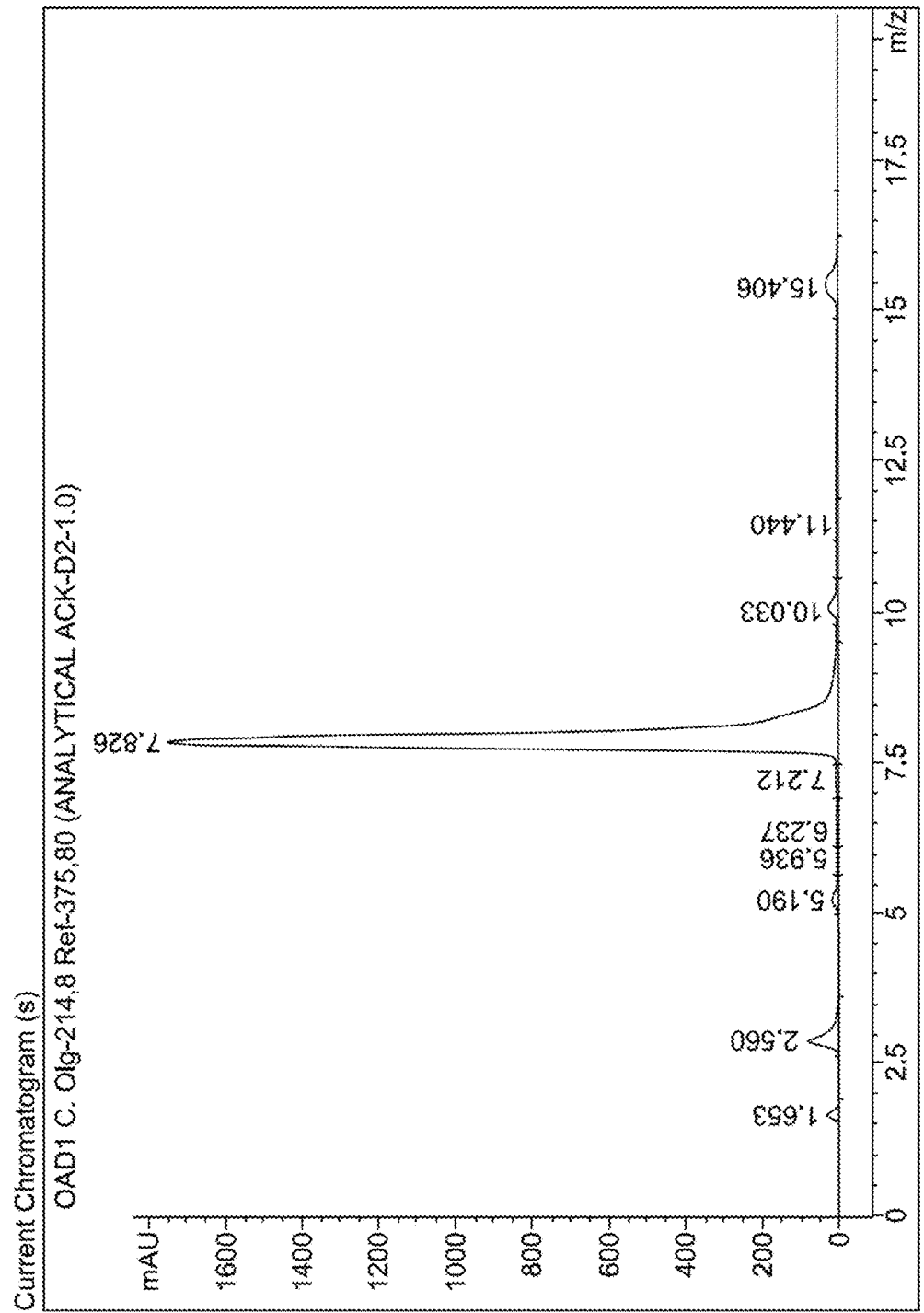
FIG. 22: HLPC trace of the compound described in FIG. 21. Conditions: 5-65% Buffer B in 20 min, Buffer A:0.1% TFA in water; Buffer B: 0.1% TFA in CAN
Figure 23:
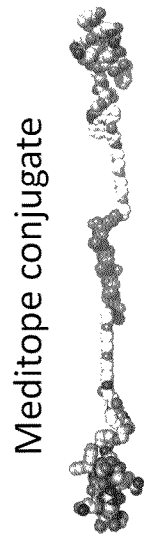
FIG. 23: LC/MS of separated Fab and meditope conjugate.
Figure 23:
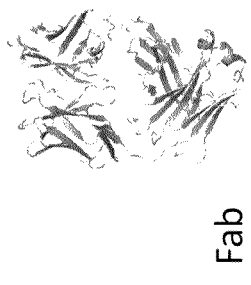
Figure 23:
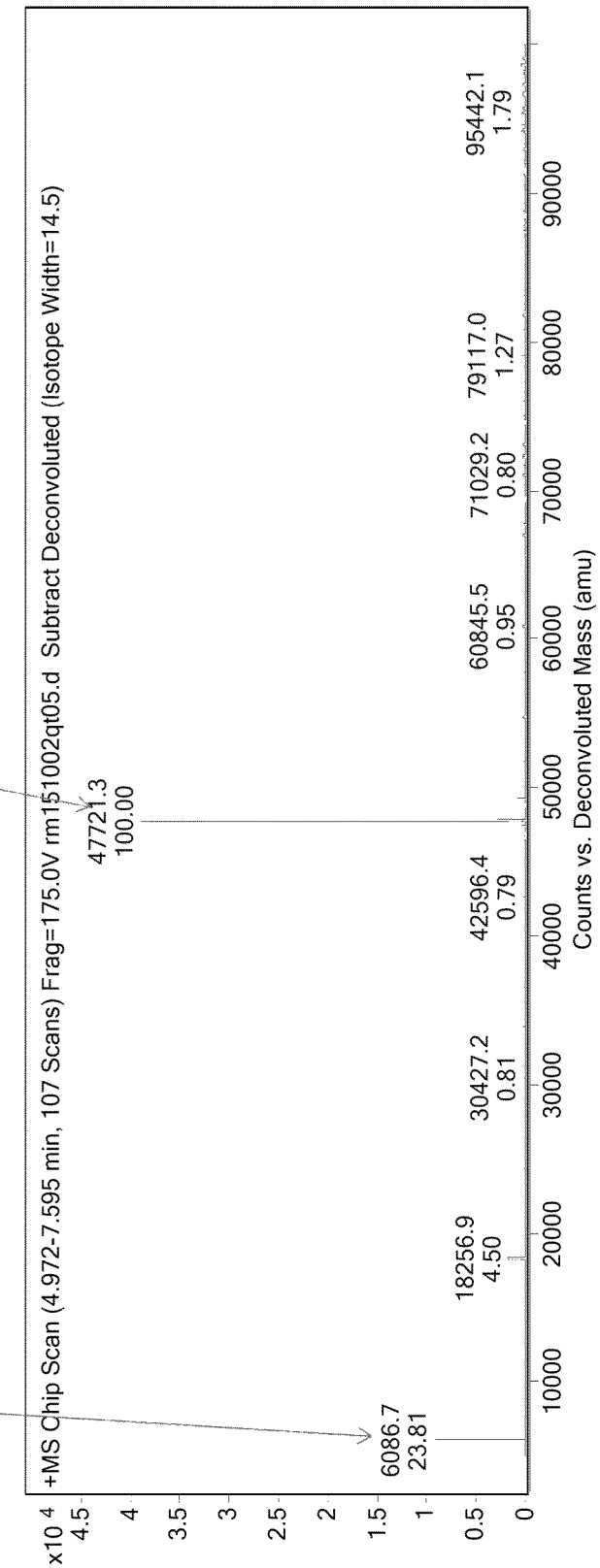
Figure 24:
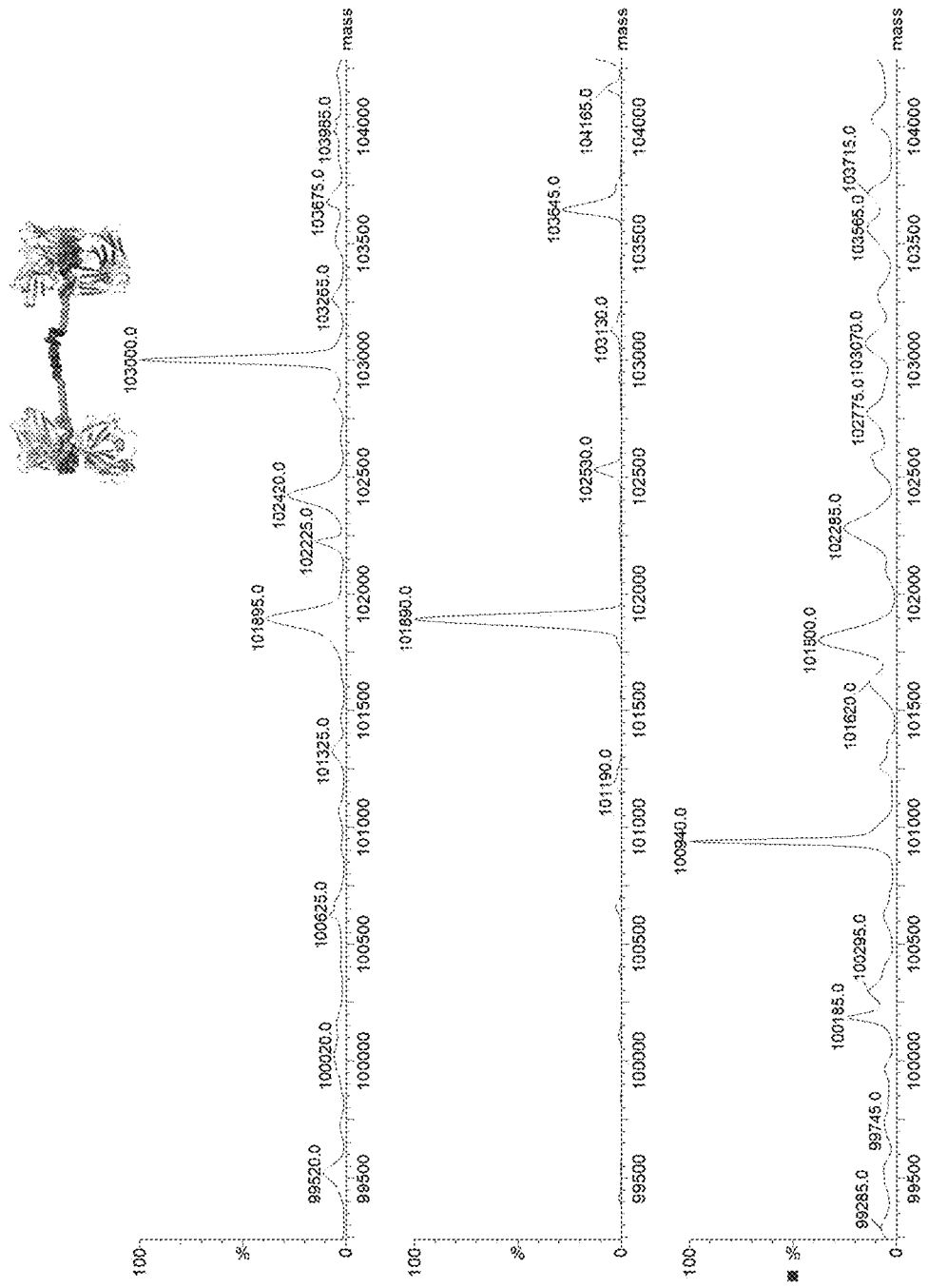
FIG. 24: Native Mass Spec, deconvoluted of linked mechanically interlocked complexes provided herein.
Figure 25:
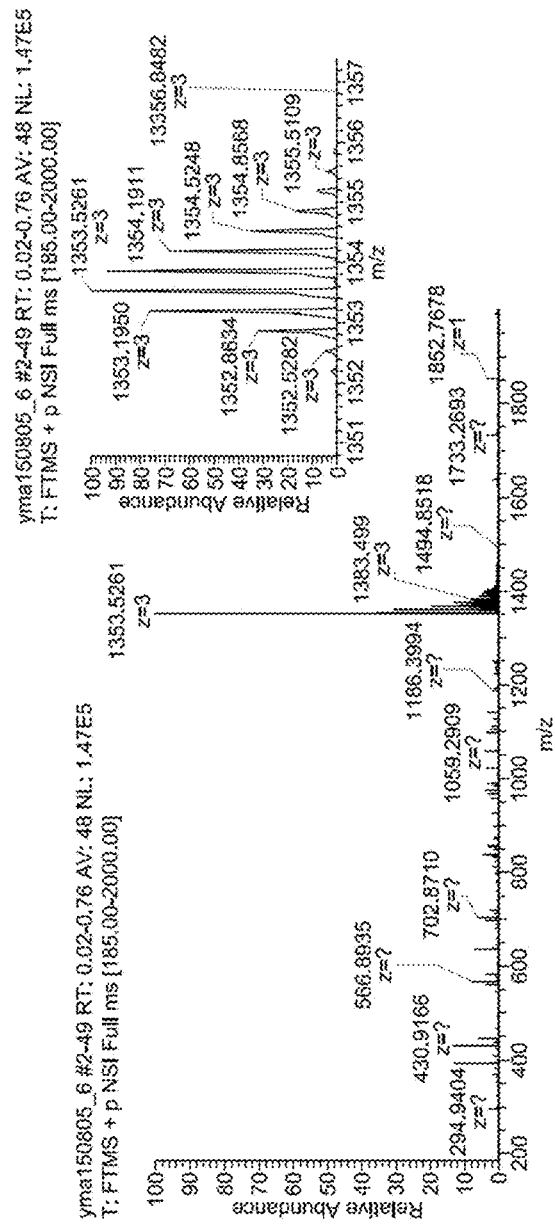
FIG. 25: Mass spectrometery showing that the azido meditope with two dyes added at each terminus was produced. Purified product: Z=3, expected: 1352.8349, observed: 1352.8634

The "central cavity" refers, with respect to the three-dimensional structure of a Fab, to the internal cavity of the Fab, lined by portions of the heavy and light chain variable and constant regions and comprising amino acids lining a hole within the cavity. The central cavity thus is lined by residues of the VH, VL, CH1, and CL regions, respectively, and does not include the antigen binding site. In embodiments, the central cavity is lined by amino acid residues capable of interacting with the compound provided herein including embodiments thereof. In embodiments, the amino acid residues lining (e.g., forming) the central cavity include a residue at a position corresponding to Kabat position 40, a residue at a position corresponding to Kabat position 41, or a residue at a position corresponding to Kabat position 85. In embodiments, the amino acid residues lining (e.g., forming) the central cavity include a residue at a position corresponding to Kabat position 83. In embodiments, the amino acid residues lining the central cavity include a residue at a position corresponding to Kabat position 85. In embodiments, the amino acid residues lining the central cavity include residues forming a peptide binding site as described in published US application US20120301400 A1, which is hereby incorporated by reference in its entirety and for all purposes. In embodiments, the central cavity including the hole has a structure, e.g., as depicted in, or similar to, FIG. 19. In embodiments, the hole is lined by (e.g., formed by) a light chain residue at a position corresponding to Kabat position Gln38, Thr40, Gln41, Gly42, Ser43, Asp85, Tyr87, Lys103, Val163, Thr164, or Glu165. In embodiments, the hole is lined (e.g., formed) by a light chain residue at a position corresponding to Kabat position Gln38. In embodiments, the hole is lined (e.g., formed) by a light chain residue at a position corresponding to Kabat position Thr40 In embodiments, the hole is lined (e.g., formed) by a light chain residue at a position corresponding to Kabat position Gln41. In embodiments, the hole is lined (e.g., formed) by a light chain residue at a position corresponding to Kabat position Gly42. In embodiments, the hole is lined (e.g., formed) by a light chain residue at a position corresponding to Kabat position to Ser43. In embodiments, the hole is lined (e.g., formed) by a light chain residue at a position corresponding to Kabat position Asp85. In embodiments, the hole is lined (e.g., formed) by a light chain residue at a position corresponding to Kabat position Tyr87. In embodiments, the hole is lined (e.g., formed) by a light chain residue at a position corresponding to Kabat position Lys103. In embodiments, the hole is lined (e.g., formed) by a light chain residue at a position corresponding to Kabat position Val163. In embodiments, the hole is lined (e.g., formed) by a light chain residue at a position corresponding to Kabat position Thr164 In embodiments, the hole is lined (e.g., formed) by a light chain residue at a position corresponding to Kabat position Glu165. A "light chain residue" as provided herein refers to a residue forming part of a light chain of an antibody or antibody fragment.

In embodiments, the hole is lined by (e.g., formed by) a heavy chain residue at a position corresponding to Kabat position Gln39, Pro40, Thr91, Ala92, Ile93, Tyr95, Gln112, Leu115, Glu155, Pro156, Pro174, Ala175, or Tyr183. In embodiments, the hole is lined (e.g., formed) by a heavy chain residue at a position corresponding to Kabat position Gln39. In embodiments, the hole is lined (e.g., formed) by a heavy chain residue at a position corresponding to Kabat position. In embodiments, the hole is lined (e.g., formed) by a heavy chain residue at a position corresponding to Kabat position Pro40. In embodiments, the hole is lined (e.g., formed) by a heavy chain residue at a position corresponding to Kabat position Thr91. In embodiments, the hole is lined (e.g., formed) by a heavy chain residue at a position corresponding to Kabat position Ala92. In embodiments, the hole is lined (e.g., formed) by a heavy chain residue at a position corresponding to Kabat position Ile93. In embodiments, the hole is lined (e.g., formed) by a heavy chain residue at a position corresponding to Kabat position Tyr95. In embodiments, the hole is lined (e.g., formed) by a heavy chain residue at a position corresponding to Kabat position Gln112. In embodiments, the hole is lined (e.g., formed) by a heavy chain residue at a position corresponding to Kabat position Leu115. In embodiments, the hole is lined (e.g., formed) by a heavy chain residue at a position corresponding to Kabat position Glu155. In embodiments, the hole is lined (e.g., formed) by a heavy chain residue at a position corresponding to Kabat position Pro156. In embodiments, the hole is lined (e.g., formed) by a heavy chain residue at a position corresponding to Kabat position Pro174. In embodiments, the hole is lined (e.g., formed) by a heavy chain residue at a position corresponding to Kabat position Ala175. In embodiments, the hole is lined (e.g., formed) by a heavy chain residue at a position corresponding to Kabat position Tyr183. A "heavy chain residue" as provided herein refers to a residue forming part of a heavy chain of an antibody or antibody fragment.

The "non-CDR binding site" included in the central cavity provided herein is a binding site within the Fab domain that does not include CDR residues of the heavy chains and CDR residues of the light chains. In embodiments, the non-CDR binding site includes FR residues of the heavy chains and FR residues of the light chains. In embodiments, the non-CDR binding site includes a residue at a position corresponding to Kabat position 40, a residue at a position corresponding to Kabat position 41, or a residue at a position corresponding to Kabat position 85. In embodiments, the non-CDR binding site includes a residue at a position corresponding to Kabat position 83. In embodiments, the non-CDR binding site includes a residue at a position corresponding to Kabat position 85. In embodiments, the non-CDR binding site includes an isoleucine to glutamic acid mutation at a position corresponding to Kabat position 83. In embodiments, residues forming a non-CDR binding site are, as described in published US application US20120301400 A1, which is hereby incorporated by reference in its entirety and for all purposes.

The non-CDR binding site provided herein is capable of binding a compound including a Fab binding moiety attached to a steric hindering chemical moiety through a chemical linker. The Fab binding moiety provided herein may be a peptide, small molecule, aptamer, nucleic acid molecule, peptibody and/or any other substance capable to bind to the non-CDR binding site. In embodiments, the Fab binding moiety is a peptide. In embodiments, the Fab binding moiety is a small molecule. In embodiments, the Fab binding moiety is an aptamer. In embodiments, the Fab binding moiety is a nucleic acid molecule. In embodiments, the Fab binding moiety is a peptibody. A "peptibody" as provided herein refers to a peptide moiety attached (through a covalent or non-covalent linker) to the Fc domain of an antibody. In embodiments, the Fab binding moiety binds the non-CDR binding site. In embodiments, the Fab binding moiety includes a substituted peptidyl moiety. In embodiments, the Fab binding moiety is a substituted peptidyl moiety.

The Fab binding moiety is bound to a steric hindering chemical moiety through a chemical linker (e.g. $-L^1-$). The chemical linker provided herein (e.g., $-L^{1.4}-$, $-L^1-$, $-L^2-$ and $-L^3-$, independently) may be a covalent or noncovalent linker. In embodiments, the chemical linker is a covalent linker. The chemical linker provided herein may include the remnants of a chemically reactive functional group reacted with a second chemically reactive functional group, thereby forming a covalent linker. Thus, a chemical linker (e.g., $-L^{1.4}-$, $-L^1-$, $-L^2-$ and $-L^3-$, independently) as referred to herein may include the resulting linker formed by reacting two reactive groups (moieties), for example, a covalent reactive group as described herein (e.g., alkyne, thiol, azide, maleimide). In embodiments, the chemical linker is a 1,3 triazole linker (i.e., a linker including a 1,3-triazolene linker moiety wherein the linker may further optionally include alkylene (substituted or unsubstituted), heteroalkylene (substituted or unsubstituted), cycloalkylene (substituted or unsubstituted), heterocycloalkylene (substituted or unsubstituted), arylene (substituted or unsubstituted), heteroarylene (substituted or unsubstituted), amide (—C(O)NH—), ester (—C(O)O—), sulfonamide (—SO$_2$NH—) and the like, including combinations thereof). The linkers provided herein may be covalently attached to the Fab binding moiety or the steric hindering chemical moiety applying methods well known in the art and compatible with the composition of the complex provided herein. The linkers provided herein may include the conjugated product of reactive groups, at the point of attachment to, for example, the Fab binding moiety or the steric hindering chemical moiety. Thus, the linkers provided herein may be polyvalent and/or may be formed by conjugate chemistry techniques. Non-limiting examples of linkers useful for the compositions and methods provided herein are linkers that include alkylene groups (substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene including substituted or unsubstituted alkylene groups and substituted or unsubstituted heteroalkylene amide (—C(O)NH—), ester (—C(O)O—), sulfonamide (—SO$_2$NH—), amine groups (—NH—), epoxyene groups, sulfone groups (—S(O)— or —SO$_2$—), ether group (—O—) or ethylene glycol or derivatives or combinations thereof.

In embodiments, the chemical linker provided herein is or includes a cleavable peptide linker, including a protease cleavage site. A "cleavage site" as used herein, refers to a recognizable site for cleavage of a portion of a linker described herein. Thus, a cleavage site may be found in the sequence of a cleavable peptide linker as described herein, including embodiments thereof. In embodiments, the cleavage site is an amino acid sequence that is recognized and cleaved by a cleaving agent (e.g., a peptidyl sequence). Exemplary cleaving agents include proteins, enzymes, DNAzymes, RNAzymes, metals, acids, and bases. In embodiments, the protease cleavage site is a tumor-associated protease cleavage site. A "tumor-associated protease cleavage site" as provided herein is an amino acid sequence recognized by a protease, whose expression is specific for a tumor cell or tumor cell environment thereof. In embodiments, the protease cleavage site is a matrix metalloprotease (MMP) cleavage site, a disintegrin and metalloprotease domain-containing (ADAM) metalloprotease cleavage site, a prostate specific antigen (PSA) protease cleavage site, a urokinase-type plasminogen activator (uPA) protease cleavage site, a membrane type serine protease 1 (MT-SP1) protease cleavage site or a legumain protease cleavage site. In embodiments, the matrix metalloprotease (MMP) cleavage site is a MMP 9 cleavage site, a MMP 13 cleavage site or a MMP 2 cleavage site. In embodiments, the disintegrin and metalloprotease domain-containing (ADAM) metalloprotease cleavage site is a ADAM 9 metalloprotease cleavage site, a ADAM 10 metalloprotease cleavage site or a ADAM 17 metalloprotease cleavage site.

A chemical linker as provided herein (e.g., $-L^{1.4}-$, $-L^1-$, $-L^2-$ and $-L^3-$, independently) may be a bond —O—, —S—, —C(O)—, —C(O)O—, —C(O)NH—, —S(O)$_2$NH—, —NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene. In embodiments, the chemical linker is a bond, —O—, —S—, —C(O)—, —C(O)O—, —C(O)NH—, —S(O)$_2$NH—, —NH—, —NHC(O)NH—, unsubstituted alkylene, unsubstituted heteroalkylene, unsubstituted cycloalkylene, unsubstituted heterocycloalkylene, unsubstituted arylene or unsubstituted heteroarylene. The chemical linker may be unsubstituted $C_1$-$C_{20}$ (e.g., $C_1$-$C_6$) alkylene, unsubstituted 2 to 20 membered (e.g., 2 to 6 membered) heteroalkylene, unsubstituted $C_3$-$C_8$ (e.g., $C_5$-$C_7$) cykloalkylene, unsubstituted 3 to 8 membered (e.g., 3 to 6 membered) heterocycloalkylene, unsubstituted $C_5$-$C_{10}$ (e.g., $C_5$-$C_6$) arylene, or unsubstituted 5 to 10 membered (e.g., 5 to 6 membered) heteroarylene. In embodiments, the chemical linker is —O—, —S—, —C(O)—, —C(O)O—, —C(O)NH—, —S(O)$_2$NH—, —NH— or —NHC(O)NH—.

In embodiments, the chemical linker is substituted with —OH, oxo, —SH, —NH$_2$, —C(O)NH$_2$, —CN, substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, the chemical linker is $R^{14}$-substituted alkylene, $R^{14}$-substituted heteroalkylene, $R^{14}$-substituted cycloalkylene, $R^{14}$-substituted heterocycloalkylene, $R^{14}$-substituted arylene or $R^{14}$-substituted heteroarylene. The chemical linker may be $R^{14}$-substituted $C_1$-$C_{20}$ (e.g., $C_1$-$C_6$) alkylene, $R^{14}$-substituted 2 to 20 membered (e.g., 2 to 6 membered) heteroalkylene, $R^{14}$-substituted $C_3$-$C_8$ (e.g., $C_5$-$C_7$) cykloalkylene, $R^{14}$-substituted 3 to 8 membered (e.g., 3 to 6 membered) heterocycloalkylene, $R^{14}$-substituted $C_5$-$C_{10}$ (e.g., $C_5$-$C_6$) arylene, or $R^{14}$-substituted 5 to 10 membered (e.g., 5 to 6 membered) heteroarylene.

$R^{14}$ is —OH, oxo, —SH, —NH$_2$, —C(O)NH$_2$, —CN, $R^{15}$-substituted or unsubstituted alkyl, $R^{15}$-substituted or unsubstituted heteroalkyl, $R^{15}$-substituted or unsubstituted cycloalkyl, $R^{15}$-substituted or unsubstituted heterocycloalkyl, $R^{15}$-substituted or unsubstituted aryl or $R^{15}$-substituted or unsubstituted heteroaryl. In embodiments, $R^{14}$ is $R^{15}$-substituted or unsubstituted $C_1$-$C_{20}$ (e.g., $C_1$-$C_6$) alkyl, $R^{15}$-substituted or unsubstituted 2 to 20 membered (e.g., 2 to 6 membered) heteroalkyl, $R^{15}$-substituted or unsubstituted $C_3$-$C_8$ (e.g., $C_5$-$C_7$) cykloalkyl, $R^{15}$-substituted or unsubstituted 3 to 8 membered (e.g., 3 to 6 membered) heterocycloalkyl, $R^{15}$-substituted or unsubstituted $C_5$-$C_{10}$ (e.g., $C_5$-$C_6$) aryl, or $R^{15}$-substituted or unsubstituted 5 to 10 membered (e.g., 5 to 6 membered) heteroaryl. In embodiments, $R^{14}$ is —OH, oxo, —SH, —NH$_2$, —C(O)NH$_2$, —CN, unsubstituted alkyl, unsubstituted heteroalkyl, unsubstituted cycloalkyl, unsubstituted heterocycloalkyl, unsubstituted aryl or unsubstituted heteroaryl.

$R^{15}$ is —OH, oxo, —SH, —NH$_2$, —C(O)NH$_2$, —CN, $R^{16}$-substituted or unsubstituted alkyl, $R^{16}$-substituted or unsubstituted heteroalkyl, $R^{16}$-substituted or unsubstituted cycloalkyl, $R^{16}$-substituted or unsubstituted heterocycloalkyl, $R^{16}$-substituted or unsubstituted aryl or $R^{16}$-substituted or unsubstituted heteroaryl. In embodiments, $R^{15}$ is $R^{16}$-substituted or unsubstituted $C_1$-$C_{20}$ (e.g., $C_1$-$C_6$) alkyl, $R^{16}$-substituted or unsubstituted 2 to 20 membered (e.g., 2 to 6 membered) heteroalkyl, $R^{16}$-substituted or unsubstituted $C_3$-$C_8$ (e.g., $C_5$-$C_7$) cykloalkyl, $R^{16}$-substituted or unsubstituted 3 to 8 membered (e.g., 3 to 6 membered) heterocycloalkyl, $R^{16}$-substituted or unsubstituted $C_5$-$C_{10}$ (e.g., $C_5$-$C_6$) aryl, or $R^{16}$-substituted or unsubstituted 5 to 10 membered (e.g., 5 to 6 membered) heteroaryl. In embodiments, $R^{15}$ is —OH, oxo, —SH, —NH$_2$, —C(O)NH$_2$, —CN, unsubstituted alkyl, unsubstituted heteroalkyl, unsubstituted cycloalkyl, unsubstituted heterocycloalkyl, unsubstituted aryl or unsubstituted heteroaryl.

$R^{16}$ is —OH, oxo, —SH, —NH$_2$, —C(O)NH$_2$, —CN, $R^{17}$-substituted or unsubstituted alkyl, $R^{17}$-substituted or unsubstituted heteroalkyl, $R^{17}$-substituted or unsubstituted cycloalkyl, $R^{17}$-substituted or unsubstituted heterocycloalkyl, $R^{17}$-substituted or unsubstituted aryl or $R^{17}$-substituted or unsubstituted heteroaryl. In embodiments, $R^{16}$ is $R^{17}$-substituted or unsubstituted $C_1$-$C_{20}$ (e.g., $C_1$-$C_6$) alkyl, $R^{17}$-substituted or unsubstituted 2 to 20 membered (e.g., 2 to 6 membered) heteroalkyl, $R^{17}$-substituted or unsubstituted $C_3$-$C_8$ (e.g., $C_5$-$C_7$) cykloalkyl, $R^{17}$-substituted or unsubstituted 3 to 8 membered (e.g., 3 to 6 membered) heterocycloalkyl, $R^{17}$-substituted or unsubstituted $C_5$-$C_{10}$ (e.g., $C_5$-$C_6$) aryl, or $R^{17}$-substituted or unsubstituted 5 to 10 membered (e.g., 5 to 6 membered) heteroaryl. In embodiments, $R^{16}$ is —OH, oxo, —SH, —NH$_2$, —C(O)NH$_2$, —CN, unsubstituted alkyl, unsubstituted heteroalkyl, unsubstituted cycloalkyl, unsubstituted heterocycloalkyl, unsubstituted aryl or unsubstituted heteroaryl.

$R^{17}$ is —OH, oxo, —SH, —NH$_2$, —C(O)NH$_2$, —CN, $R^{18}$-substituted or unsubstituted alkyl, $R^{18}$-substituted or unsubstituted heteroalkyl, $R^{18}$-substituted or unsubstituted cycloalkyl, $R^{18}$-substituted or unsubstituted heterocycloalkyl, $R^{18}$-substituted or unsubstituted aryl or $R^{18}$-substituted or unsubstituted heteroaryl. In embodiments, $R^{17}$ is $R^{18}$-substituted or unsubstituted $C_1$-$C_{20}$ (e.g., $C_1$-$C_6$) alkyl, $R^{18}$-substituted or unsubstituted 2 to 20 membered (e.g., 2 to 6 membered) heteroalkyl, $R^{18}$-substituted or unsubstituted $C_3$-$C_8$ (e.g., $C_5$-$C_7$) cykloalkyl, $R^{18}$-substituted or unsubstituted 3 to 8 membered (e.g., 3 to 6 membered) heterocycloalkyl, $R^{18}$-substituted or unsubstituted $C_5$-$C_{10}$ (e.g., $C_5$-$C_6$) aryl, or $R^{18}$-substituted or unsubstituted 5 to 10 membered (e.g., 5 to 6 membered) heteroaryl. In embodiments, $R^{17}$ is —OH, oxo, —SH, —NH$_2$, —C(O)NH$_2$, —CN, unsubstituted alkyl, unsubstituted heteroalkyl, unsubstituted cycloalkyl, unsubstituted heterocycloalkyl, unsubstituted aryl or unsubstituted heteroaryl.

$R^{18}$ is —OH, oxo, —SH, —NH$_2$, —C(O)NH$_2$, —CN, unsubstituted alkyl, unsubstituted heteroalkyl, unsubstituted cycloalkyl, unsubstituted heterocycloalkyl, unsubstituted aryl or unsubstituted heteroaryl. In embodiments, $R^{18}$ is unsubstituted $C_1$-$C_{20}$ (e.g., $C_1$-$C_6$) alkyl, unsubstituted 2 to 20 membered (e.g., 2 to 6 membered) heteroalkyl, unsubstituted $C_3$-$C_8$ (e.g., $C_5$-$C_7$) cykloalkyl, unsubstituted 3 to 8 membered (e.g., 3 to 6 membered) heterocycloalkyl, unsubstituted $C_5$-$C_{10}$ (e.g., $C_5$-$C_6$) aryl, or unsubstituted 5 to 10 membered (e.g., 5 to 6 membered) heteroaryl.

In some embodiments, a compound as described herein may include multiple instances of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$ and/or other variables (e.g., $L^1$, $L^{1.4}$, $L^2$, $L^3$). In such embodiments, each variable may optional be different and be appropriately labeled to distinguish each group for greater clarity. For example, where each $R^1$, $R^2$, $R^3$, $R^4$, $R^5$, $R^6$, $R^7$, $R^8$, $R^9$, $R^{10}$, $R^{11}$ $R^{12}$, $R^{13}$, $R^{14}$, $R^{15}$, $R^{16}$, $R^{17}$, $R^{18}$, $R^{19}$, $R^{20}$ and/or $R^{21}$, is different, they may be referred to, for example, as $R^{1.1}$, $R^{1.2}$, $R^{1.3}$, $R^{1.4}$, $R^{1.5}$, $R^{1.6}$, $R^{2.1}$, $R^{2.2}$, $R^{2.3}$, $R^{2.4}$, $R^{2.5}$, $R^{2.6}$, $R^{3.1}$, $R^{3.2}$, $R^{3.3}$, $R^{3.4}$, $R^{3.5}$, $R^{3.6}$, $R^{4.1}$, $R^{4.2}$, $R^{4.3}$, $R^{4.4}$, $R^{4.5}$, $R^{4.6}$, $R^{5.1}$, $R^{5.2}$, $R^{5.3}$, $R^{5.4}$, $R^{5.5}$, $R^{5.6}$, $R^{6.1}$, $R^{6.2}$, $R^{6.3}$, $R^{6.4}$, $R^{6.5}$, $R^{6.6}$, $R^{7.1}$, $R^{7.2}$, $R^{7.3}$, $R^{7.4}$, $R^{7.5}$, $R^{7.6}$, $R^{8.1}$, $R^{8.2}$, $R^{8.3}$, $R^{8.4}$, $R^{8.5}$, $R^{8.6}$, $R^{9.1}$, $R^{9.2}$, $R^{9.3}$, $R^{9.4}$, $R^{9.5}$, $R^{9.6}$, $R^{10.1}$, $R^{10.2}$, $R^{10.3}$, $R^{10.4}$, $R^{10.5}$, $R^{10.6}$, $R^{11.1}$, $R^{11.2}$, $R^{11.3}$, $R^{11.4}$, $R^{11.5}$, $R^{11.6}$, $R^{12.1}$, $R^{12.2}$, $R^{12.3}$, $R^{12.4}$, $R^{12.5}$, $R^{12.6}$, $R^{13.1}$, $R^{13.2}$, $R^{13.3}$, $R^{13.4}$, $R^{13.5}$, $R^{13.6}$, $R^{14.1}$, $R^{14.2}$, $R^{14.3}$, $R^{14.4}$, $R^{14.5}$, $R^{14.6}$, $R^{15.1}$, $R^{15.2}$, $R^{15.3}$, $R^{15.4}$, $R^{15.5}$, $R^{15.6}$, $R^{16.1}$, $R^{16.2}$, $R^{16.3}$, $R^{16.4}$, $R^{16.5}$, $R^{16.6}$, $R^{17.1}$, $R^{17.2}$, $R^{17.3}$, $R^{17.4}$, $R^{17.5}$, $R^{17.6}$, $R^{18.1}$, $R^{18.2}$, $R^{18.3}$, $R^{18.4}$, $R^{18.5}$, $R^{18.6}$, $R^{19.1}$, $R^{19.2}$, $R^{19.3}$, $R^{19.4}$, $R^{19.5}$, $R^{19.6}$, $R^{20.1}$, $R^{20.2}$, $R^{20.3}$, $R^{20.4}$, $R^{20.5}$, $R^{20.6}$, $R^{21.1}$, $R^{21.2}$, $R^{21.3}$, $R^{21.4}$, $R^{21.5}$, or $R^{21.6}$, respectively, wherein the definition of $R^1$ is assumed by $R^{1.1}$, $R^{1.2}$, $R^{1.3}$, $R^{1.4}$, $R^{1.5}$, $R^{1.6}$, $R^2$ is assumed by $R^{2.1}$, $R^{2.2}$, $R^{2.3}$, $R^{2.4}$, $R^{2.5}$, $R^{2.6}$, $R^{3.1}$ is assumed by $R^{3.1}$, $R^{3.2}$, $R^{3.3}$, $R^{3.4}$, $R^{3.5}$, $R^{3.6}$, $R^4$ is assumed by $R^{4.1}$, $R^{4.2}$, $R^{4.3}$, $R^{4.4}$, $R^{4.5}$, $R^{4.6}$, $R^5$ is assumed by $R^{5.1}$, $R^{5.2}$, $R^{5.3}$, $R^{5.4}$, $R^{5.5}$, $R^{5.6}$, $R^6$ is assumed by $R^{6.1}$, $R^{6.2}$, $R^{6.3}$, $R^{6.4}$, $R^{6.5}$, $R^{6.6}$, $R^7$ is assumed by $R^{7.1}$, $R^{7.2}$, $R^{7.3}$, $R^{7.4}$, $R^{7.5}$, $R^{7.6}$, $R^8$ is assumed by $R^{8.1}$, $R^{8.2}$, $R^{8.3}$, $R^{8.4}$, $R^{8.5}$, $R^{8.6}$, $R^9$ is assumed by $R^{9.1}$, $R^{9.2}$, $R^{9.3}$, $R^{9.4}$, $R^{9.5}$, $R^{9.6}$, $R^{10}$ is assumed by $R^{10.1}$, $R^{10.2}$, $R^{10.3}$, $R^{10.4}$, $R^{10.5}$, $R^{10.6}$, $R^{11}$ is assumed by $R^{11.1}$, $R^{11.2}$, $R^{11.3}$, $R^{11.4}$, $R^{11.5}$, $R^{11.6}$, $R^{12}$ is assumed by $R^{12.1}$, $R^{12.2}$, $R^{12.3}$, $R^{12.4}$, $R^{12.5}$, $R^{12.6}$, $R^{13}$ is assumed by $R^{13.1}$, $R^{13.2}$, $R^{13.3}$, $R^{13.4}$, $R^{13.5}$, $R^{13.6}$, $R^{14}$ is assumed by $R^{14.1}$, $R^{14.2}$, $R^{14.3}$, $R^{14.4}$, $R^{14.5}$, $R^{14.6}$, $R^{15}$ is assumed by $R^{15.1}$, $R^{15.2}$, $R^{15.3}$, $R^{15.4}$, $R^{15.5}$, $R^{15.6}$, $R^{16.6}$, $R^{16}$ is assumed by $R^{16.2}$, $R^{16.3}$, $R^{16.4}$, $R^{16.5}$, $R^{16.6}$, $R^{17}$ is assumed by $R^{17.1}$, $R^{17.2}$, $R^{17.3}$, $R^{17.4}$, $R^{17.5}$, $R^{17.6}$, $R^{18}$ is assumed by $R^{18.1}$, $R^{18.2}$, $R^{18.3}$, $R^{18.4}$, $R^{18.5}$, $R^{18.6}$, $R^{19}$ is assumed $R^{19.1}$, $R^{19.2}$, $R^{19.3}$, $R^{19.4}$, $R^{19.5}$, $R^{19.6}$, $R^{20}$ is assumed $R^{20.1}$, $R^{20.2}$, $R^{20.3}$, $R^{20.4}$, $R^{20.5}$, $R^{20.6}$, and/or $R^{21}$ is assumed $R^{21.1}$, $R^{21.2}$, $R^{21.3}$, $R^{21.4}$, $R^{21.5}$, or $R^{21.6}$. The variables used within a definition of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$ and/or other variables (e.g., $L^1$, $L^{1A}$, $L^2$, $L^3$, $L^{3A}$, $L^{3B}$, $L^{3C}$, $L^{3D}$) that appear at multiple instances and are different may similarly be appropriately labeled to distinguish each group for greater clarity. In some embodiments, the compound is a compound described herein (e.g., in an aspect, embodiment, example, claim, table, scheme, drawing, or figure).

In embodiments, the chemical linker is a covalent linker, a non-covalent linker, a peptide linker (a linker including a peptide moiety), a cleavable peptide linker, a substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene or any combination thereof. Thus, a chemical linker as provided herein may include a plurality of chemical moieties, wherein each of the plurality of moieties are chemically different. In embodiments, the chemical linker includes a first substituted or unsubstituted heteroalkylene (e.g., substituted or unsubstituted polyethylene glycol) connected through a peptide linker with a second substituted or unsubstituted heteroalkylene (e.g., substituted or unsubstituted polyethylene glycol).

In embodiments, the chemical linker is or includes a substituted or unsubstituted polyethylene glycol or derivative thereof. In embodiments, the chemical linker is a substituted polyethylene glycol or derivative thereof. In embodiments, the chemical linker is an unsubstituted polyethylene glycol or derivative thereof.

Upon binding of the Fab binding to the non-CDR binding site, the chemical linker passes through the hole of the Fab domain and may be reacted with the steric hindering chemical moiety. The steric hindering chemical moiety provided herein is a moiety which is sterically hindered to pass through the hole forming part of the Fab domain. The steric hindrance occurs between the steric hindering chemical moiety and the amino acids lining the Fab hole, thereby facilitating the mechanical interlock. Thus, the steric hindering chemical moiety is sufficient in size, dimension or volume to create steric hindrance ("plug"), thereby significantly decreasing (e.g., inhibiting or preventing) the ability of the steric hindering chemical moiety to pass through the hole towards the side of the Fab domain to which the Fab binding moiety is attached. In embodiments, the longest diameter of the hole (e.g., the longest distance across the hole measured from amino acid residue to amino acid residue by crystal structure) in which the steric hindering chemical moiety could pass is shorter than the longest dimension (e.g., diameter) of the steric hindering chemical moiety (also referred to herein as $R^2$). In embodiments, the hole (e.g., the longest diameter of the hole as measure in a crystal structure) is from about 3 to about 10 Å in size (e.g., in length, in diameter). In embodiments, the longest dimension of the steric hindering chemical moiety is more than about 3 to about 10 Å in size. For example, where the hole is 8 Å in size (e.g., the longest diameter of the hole as measure in a crystal structure or diameter), the steric hindering chemical moiety is more than about 8 Å in size (i.e., the longest dimension is more than about 8 Å in size). Binding of the steric hindering chemical moiety to the remainder of the compound is typically accomplished using click chemistry. In embodiments, a chemically reactive functional group (e.g., alkyne) is present on the steric hindering chemical moiety that is reacted with a conjugate (click) chemistry present on the chemical linker to be reacted. In embodiments, the chemically reactive functional group of the steric hindering chemical moiety is alkyne and the chemically reactive functional group of the linker is azide (e.g., $L^1$) is azide.

In embodiments, the steric hindering chemical moiety is a substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl. In embodiments, the steric hindering chemical moiety is substituted or unsubstituted diphenyl. Thus, in embodiments, $R^2$ is a substituted or unsubstituted alkyl, substituted or unsubstituted heteroalkyl, substituted or unsubstituted cycloalkyl, substituted or unsubstituted heterocycloalkyl, substituted or unsubstituted aryl or substituted or unsubstituted heteroaryl.

In embodiments, $R^2$ is $R^{19}$-substituted or unsubstituted alkyl, $R^{19}$-substituted or unsubstituted heteroalkyl, $R^{19}$-substituted or unsubstituted cycloalkyl, $R^{19}$-substituted or unsubstituted heterocycloalkyl, $R^{19}$-substituted or unsubstituted aryl, or $R^{19}$-substituted or unsubstituted heteroaryl. $R^2$ may be $R^{19}$-substituted or unsubstituted $C_1$-$C_{20}$ (e.g., $C_1$-$C_6$) alkyl, $R^{19}$-substituted or unsubstituted 2 to 20 membered (e.g., 2 to 6 membered) heteroalkyl, $R^{19}$-substituted or unsubstituted $C_3$-$C_8$ (e.g., $C_5$-$C_7$) cycloalkyl, $R^{19}$-substituted or unsubstituted 3 to 8 membered (e.g., 3 to 6 membered) heterocycloalkyl, $R^{19}$-substituted or unsubstituted $C_5$-$C_{10}$ (e.g., $C_5$-$C_6$) aryl, or $R^{19}$-substituted or unsubstituted 5 to 10 membered (e.g., 5 to 6 membered) heteroaryl. In embodiments, $R^2$ is unsubstituted alkyl, unsubstituted heteroalkyl, unsubstituted cycloalkyl, heterocycloalkyl, unsubstituted aryl, or unsubstituted heteroaryl.

$R^{19}$ is halogen, =O (oxo), —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, or —NHC=(O)$NHNH_2$, $R^{20}$-substituted or unsubstituted alkyl, $R^{20}$-substituted or unsubstituted heteroalkyl, $R^{20}$-substituted or unsubstituted cycloalkyl, $R^{20}$-substituted or unsubstituted heterocycloalkyl, $R^{20}$-substituted or unsubstituted aryl, or $R^{20}$-substituted or unsubstituted heteroaryl. $R^{19}$ may be $R^{20}$-substituted or unsubstituted $C_1$-$C_{20}$ (e.g., $C_1$-$C_6$) alkyl, $R^{20}$-substituted or unsubstituted 2 to 20 membered (e.g., 2 to 6 membered) heteroalkyl, $R^{20}$-substituted or unsubstituted $C_3$-$C_8$ (e.g., $C_5$-$C_7$) cykloalkyl, $R^{20}$-substituted or unsubstituted 3 to 8 membered (e.g., 3 to 6 membered) heterocycloalkyl, $R^{20}$-substituted or unsubstituted $C_5$-$C_{10}$ (e.g., $C_5$-$C_6$) aryl, or $R^{20}$-substituted or unsubstituted 5 to 10 membered (e.g., 5 to 6 membered) heteroaryl. In embodiments, $R^{19}$ is unsubstituted alkyl, unsubstituted heteroalkyl, unsubstituted cycloalkyl, heterocycloalkyl, unsubstituted aryl, or unsubstituted heteroaryl.

$R^{20}$ is halogen, =O (oxo), —$CF_3$, —CN, —$CCl_3$, —COOH, —$CH_2COOH$, —$CONH_2$, —OH, —SH, —$SO_2Cl$, —$SO_3H$, —$SO_4H$, —$SO_2NH_2$, —$NO_2$, —$NH_2$, —$NHNH_2$, —$ONH_2$, or —NHC=(O)$NHNH_2$, $R^{21}$-substituted or unsubstituted alkyl, $R^{21}$-substituted or unsubstituted heteroalkyl, $R^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl. $R^{20}$ may be $R^{21}$-substituted or unsubstituted $C_1$-$C_{20}$ (e.g., $C_1$-$C_6$) alkyl, $R^{21}$-substituted or unsubstituted 2 to 20 membered (e.g., 2 to 6 membered) heteroalkyl, $R^{21}$-substituted or unsubstituted $C_3$-$C_8$ (e.g., $C_5$-$C_7$) cykloalkyl, $R^{21}$-substituted or unsubstituted 3 to 8 membered (e.g., 3 to 6 membered) heterocycloalkyl, $R^{21}$-substituted or unsubstituted $C_5$-$C_{10}$ (e.g., $C_5$-$C_6$) aryl, or $R^{21}$-substituted or unsubstituted 5 to 10 membered (e.g., 5 to 6 membered) heteroaryl. In embodiments, $R^{20}$ is unsubstituted alkyl, unsubstituted heteroalkyl, unsubstituted cycloalkyl, heterocycloalkyl, unsubstituted aryl, or unsubstituted heteroaryl.

$R^{21}$ is halogen, =O oxo), —$CF_3$, —CN, —$CCl_3$, —COOH, —$CH_2$COOH, —$CONH_2$, —OH, —SH, —$SO_2$Cl, —$SO_3$H, —$SO_4$H, —$SO_2NH_2$, —$NO_2$, —$NH_2$, —$NHNH_2$, —$ONH_2$, —NHC=(O)$NHNH_2$, unsubstituted alkyl, unsubstituted heteroalkyl, unsubstituted cycloalkyl, unsubstituted heterocycloalkyl, unsubstituted aryl, or unsubstituted heteroaryl. In embodiments, $R^{21}$ is unsubstituted $C_1$-$C_{20}$ (e.g., $C_1$-$C_6$) alkyl, unsubstituted 2 to 20 membered (e.g., 2 to 6 membered) heteroalkyl, unsubstituted $C_3$-$C_8$ (e.g., $C_5$-$C_7$) cykloalkyl, unsubstituted 3 to 8 membered (e.g., 3 to 6 membered) heterocycloalkyl, unsubstituted $C_5$-$C_{10}$ (e.g., $C_5$-$C_6$) aryl, or unsubstituted 5 to 10 membered (e.g., 5 to 6 membered) heteroaryl.

The steric hindering chemical moiety may or may not bind or interact with the non-CDR binding site. In embodiments, the steric hindering chemical moiety does not bind or interact with the non-CDR binding site.

The complexes provided herein may include a therapeutic agent, a diagnostic agent or a detectable agent (also referred to herein as a detectable agent). The therapeutic agent, diagnostic agent or detectable agent (also referred to herein as $R^5$) may be attached through a non-covalent or covalent linker (also referred to herein as $L^2$) to the steric hindering chemical moiety (also referred to herein as $R^2$) and/or the Fab binding domain (also referred to herein as $R^1$) provided herein including embodiments thereof. In embodiments, $R^5$ is attached to the steric hindering chemical moiety through a chemical linker, $L^2$, that is a non-covalent or covalent linker. In embodiments, $L^2$ is a covalent linker. $L^2$ provided herein may include the remnants of a chemically reactive functional group reacted with a second chemically reactive functional group, thereby forming a covalent linker. In embodiments, $L^2$ is a bond, —O—, —S—, —C(O)—, —C(O)O—, —C(O)NH—, —S(O)$_2$NH—, —NH—, —NHC(O)NH—, unsubstituted alkylene, unsubstituted heteroalkylene, unsubstituted cycloalkylene, unsubstituted heterocycloalkylene, unsubstituted arylene or unsubstituted heteroarylene. In embodiments, $R^2$ is a substituted or unsubstituted diphenyl, $L^2$ is —O— or substituted or unsubstituted heteroalkyl (e.g., unsubstituted 2 to 5-membered heteroalkyl) and $R^5$ is a detectable moiety (e.g., ALEXA fluor) (e.g., FIG. 1).

In embodiments, $R^5$ is attached to the Fab binding domain through chemical linker, $L^2$, that is a non-covalent or covalent linker. In some aspects, the linker, $L^2$, may be a covalent linker as described herein and formed through conjugate (e.g. "click") chemistry. The linker, $L^2$, may further be a cleavable peptide linker as described herein. Where the therapeutic, diagnostic or detectable agent forms part (e.g., through covalent attachment) of the complex provided herein, including embodiments thereof, the therapeutic, diagnostic or detectable agent may be referred to as a "compound moiety" (e.g., therapeutic moiety, imaging moiety, detectable). In some aspects, the complexes provided herein including embodiments thereof, may provide highly specific and efficient means for targeted cancer drug delivery and/or molecular imaging.

In embodiments, the complex includes a therapeutic moiety (also referred to herein as $R^5$) covalently attached to the complex through a linker, $L^2$. In embodiments, $R^5$ is a therapeutic moiety. In embodiments, $R^5$ is connected to the Fab binding domain through a covalent linker, $L^2$. In embodiments, $R^5$ is connected to the steric hindering chemical moiety through a covalent linker, $L^2$. The term "therapeutic moiety" as provided herein is used in accordance with its plain ordinary meaning and refers to a monovalent compound having a therapeutic benefit (e.g., prevention, eradication, amelioration of the underlying disorder being treated) when given to a subject in need thereof. Therapeutic moieties as provided herein may include, without limitation, peptides, proteins, nucleic acids, nucleic acid analogs, small molecules, antibodies, enzymes, prodrugs, cytotoxic agents (e.g. toxins) including, but not limited to ricin, doxorubicin, daunorubicin, taxol, ethidium bromide, mitomycin, etoposide, tenoposide, vincristine, vinblastine, colchicine, dihydroxy anthracin dione, actinomycin D, diphtheria toxin, Pseudomonas exotoxin (PE) A, PE40, abrin, and glucocorticoid. In embodiments, the therapeutic moiety is an anticancer agent or chemotherapeutic agent as described herein. In embodiments, the therapeutic moiety is a nucleic acid moiety, a peptide moiety or a small molecule drug moiety. In embodiments, the therapeutic moiety is a nucleic acid moiety. In embodiments, the therapeutic moiety is an antibody moiety. In embodiments, the therapeutic moiety is a peptide moiety. In embodiments, the therapeutic moiety is a small molecule drug moiety. In embodiments, the therapeutic moiety is a nuclease. In embodiments, the therapeutic moiety is an immunostimulator. In embodiments, the therapeutic moiety is a toxin. In embodiments, the therapeutic moiety is a nuclease. In embodiments, the therapeutic moiety is auristatin. In embodiments, the therapeutic moiety is mertansine.

The complex provided herein may include an imaging or detectable moiety. In embodiments, $R^5$ is a detectable moiety. In embodiments, $R^5$ is connected to the Fab binding domain through a covalent linker, $L^2$. In embodiments, $R^5$ is connected to the steric hindering chemical moiety through a covalent linker, $L^2$. An "imaging or detectable moiety" as provided herein is a monovalent compound detectable by spectroscopic, photochemical, biochemical, immunochemical, chemical, or other physical means. In embodiments, the imaging moiety is covalently attached to the Fab binding domain. In embodiments, the imaging moiety is covalently attached to the steric hindering chemical moiety. Exemplary imaging moieties are without limitation $^{32}$P, radionuclides, positron-emitting isotopes, fluorescent dyes, fluorophores, antibodies, bioluminescent molecules, chemiluminescent molecules, photoactive molecules, metals, electron-dense reagents, enzymes (e.g., as commonly used in an ELISA), magnetic contrast agents, quantum dots, nanoparticles, biotin, digoxigenin, haptens and proteins or other entities which can be made detectable, e.g., by incorporating a radiolabel into a peptide or antibody specifically reactive with a target peptide. Any method known in the art for conjugating an antibody to the moiety may be employed, e.g., using methods described in Hermanson, Bioconjugate Techniques 1996, Academic Press, Inc., San Diego. Exemplary fluorophores include fluorescein, rhodamine, GFP, coumarin, FITC, ALEXA fluor, Cy3, Cy5, BODIPY, and cyanine dyes. Exemplary radionuclides include Fluorine-18, Gallium-68, and Copper-64. Exemplary magnetic contrast agents include gadolinium, iron oxide and iron platinum, and manganese. In embodiments, the imaging moiety is a bioluminescent molecule. In embodiments, the imaging moiety is a photoactive molecule. In embodiments, the imaging moiety is a metal. In embodiments, the imaging moiety is a nanoparticle.

In one embodiment, the compound has the structure:
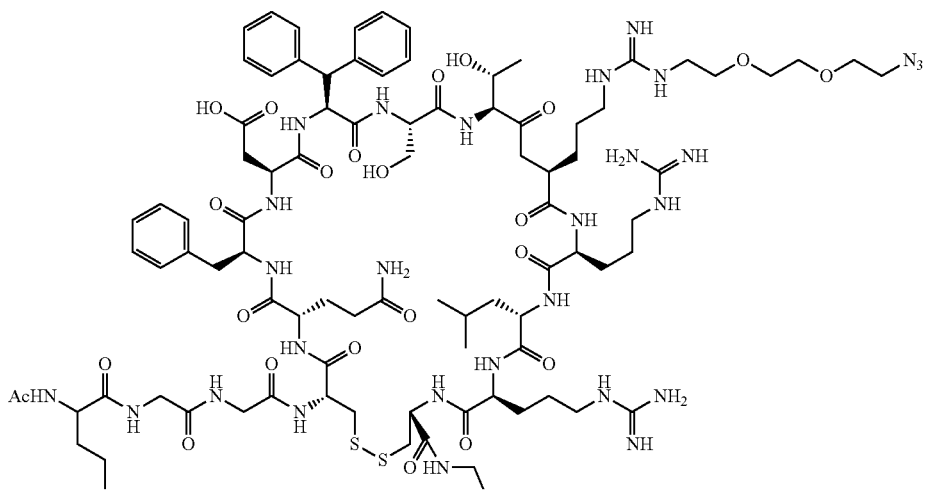
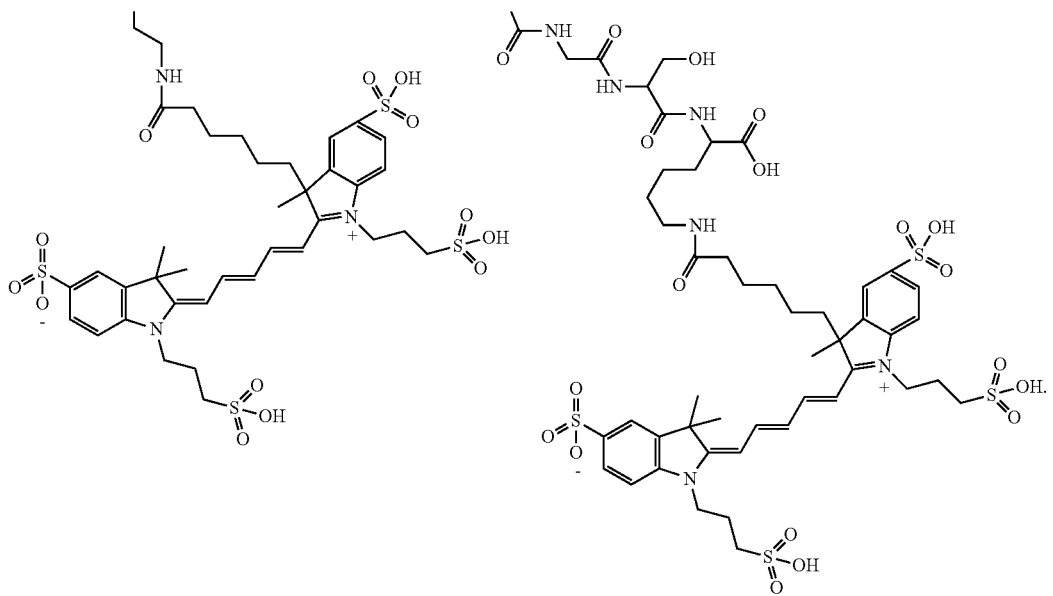
Chemical Formula: $C_{173}H_{246}N_{38}O_{55}S_{10}$
Exact Mass: 4055.4828
1 4056.4901
2 2028.7487
3 1352.8349
4 1014.8780
5 812.1038

Linked Complexes

As described herein the steric hindering chemical moiety (also referred to herein as $R^2$) may be substituted or unsubstituted. In embodiments, $R^2$ is substituted with a chemical linker (referred to herein as $L^3$) to an additional chemical moiety. $L^3$ is a chemical linker as described herein. In embodiments, $L^3$ is a bond, covalent linker, a non-covalent linker, a peptide linker, a cleavable peptide linker, a substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene or any combination thereof. In embodiments, $L^3$ is —O—, —S—, —C(O)—, —C(O)O—, —C(O)NH—, —S(O)$_2$NH—, —NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene. In embodiments, $L^3$ is or includes a peptide linker. In embodiments, $L^3$ is or includes a cleavable peptide linker. In embodiments, $L^3$ links an additional chemical moiety to the steric chemical hindering moiety. In embodiments, $L^3$ links an additional chemical moiety to the peptidyl moiety. Thus, in embodiments, $L^3$ links an additional chemical moiety to $R^2$. In embodiments, $L^3$ links an additional chemical moiety to $R^1$. In embodiments, $L^3$ links an additional chemical moiety to $R^3$ or $R^4$. The additional chemical moiety may be a second mechanically interlocked complex as provided herein or a masking peptide moiety.

Linked Mechanically Interlocked Complexes

Where the chemical moiety is a second mechanically interlocked complex, the chemical linker $L^3$ may link a first mechanically interlocked complex to a second mechanically interlocked complex. Thus, in embodiments, a composition comprising a plurality of mechanically interlocked complexes is provided. The plurality of complexes may include a first mechanically interlocked complex and a second mechanically interlocked complex covalently attached through a chemical linker (such as $L^3$) as provided herein. Thus, in one aspect, a linked mechanically interlocked complex is provided. The linked mechanically interlocked complex includes a first mechanically interlocked complex as provided herein including embodiments thereof bound to a second mechanically interlocked complex as provided herein including embodiments thereof through a chemical linker.

Figure 3A:
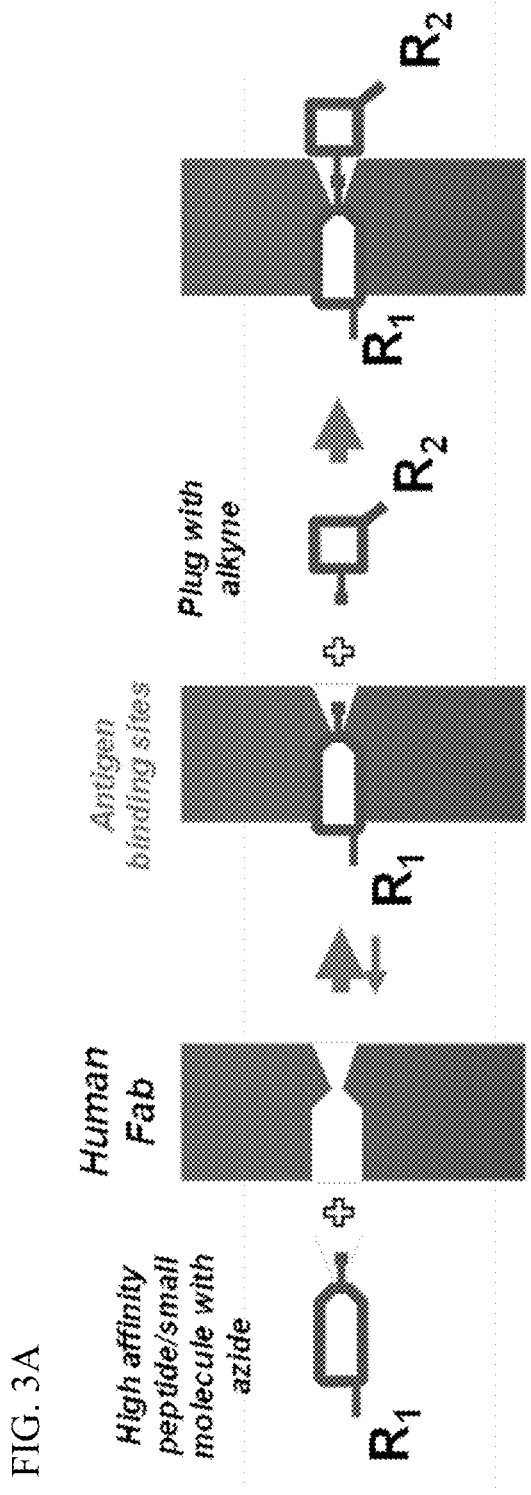
FIGS. 3A-3F.
Figure 3B:
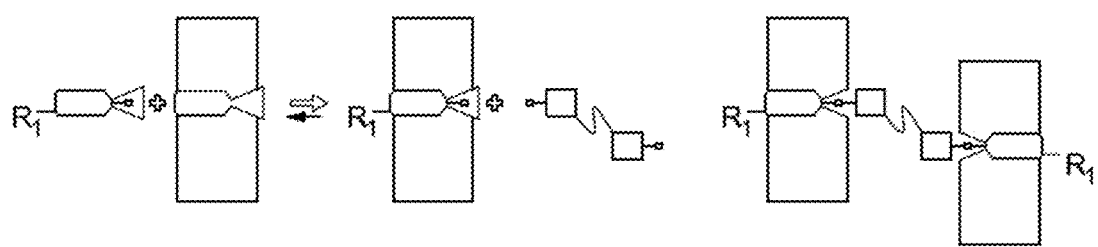
Figure 3B:
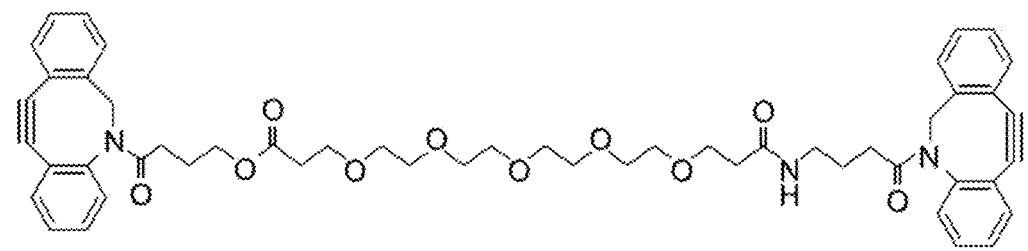
Figure 3B:
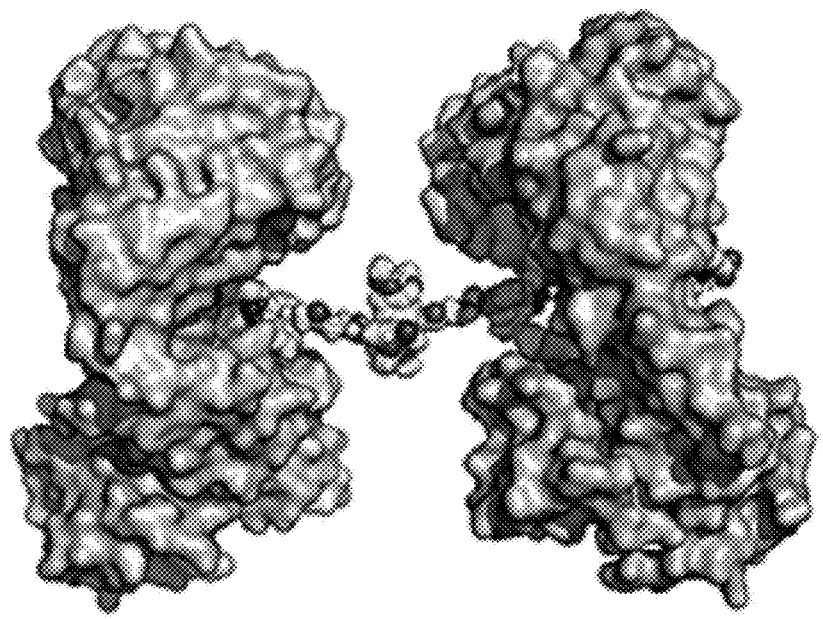

In embodiments, the chemical linker binds the steric hindering chemical moiety of the first mechanically interlocked complex to the steric hindering chemical moiety of the second mechanically interlocked complex (e.g., FIG. 3B). In embodiments, the linked mechanically interlocked complex has the formula:

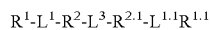
(I).

In formula (I), $R^1$, $L^1$, $R^2$ are as defined herein, $L^3$ is a chemical linker as defined herein and $R^{1.1}$ is the peptidyl moiety of the second mechanically interlocked complex, $L^{1.11}$ is the chemical linker of the second mechanically interlocked complex and $R^{2.1}$ is the steric hindering chemical group of the second mechanically interlocked complex. As described herein, the molecules provided herein may include multiple instances of for example, $R^1$, $L^1$ and $R^2$ and each variable may optionally be different and be appropriately labeled to distinguish each group for greater clarity. Therefore, additional occurrences of, for example, $R^1$, $L^1$ and $R^2$ are labeled herein as $R^{2.1}$-$L^{1.1}$-$R^{1.1}$. In embodiments, $L^3$ is a covalent linker. In embodiments, $L^3$ is a bond, —O—, —S—, —C(O)—, —C(O)O—, —C(O)NH—, —S(O)$_2$NH—, —NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene. In embodiments, $L^3$ is substituted or unsubstituted heteroalkylene. In embodiments, $L^3$ is or includes a substituted or unsubstituted polyethylene glycol. In embodiments, $L^3$ has the formula:

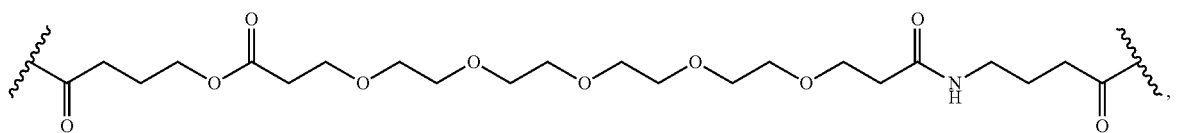
(IA)

wherein the point of attachment on the right side of $L^3$ connects to $R^{2.1}$ and the point of attachment on the left side of $L^3$ binds to $R^2$.

In embodiments, $L^3$ is a chemical linker including a combination of linkers (i.e. at least two linkers). Thus, in embodiments, $L^3$ has the formula

(II).

In formula (II), $L^{3A}$, $L^{3B}$ and $L^{3C}$ are independently a bond, —O—, —S—, —C(O)—, —C(O)O—, —C(O)NH—, —S(O)$_2$NH—, —NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene, a peptide linker or a cleavable peptide linker. In embodiments, $L^{3A}$, $L^{3B}$ and $L^{3C}$ are independently substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene. In embodiments, $L^{3A}$, $L^{3B}$ and $L^{3C}$ are independently substituted or unsubstituted heteroalkylene. In embodiments, $L^{3A}$, $L^{3B}$ and $L^{3C}$ are independently a peptide linker. In embodiments, $L^{3A}$, $L^{3B}$ and $L^{3C}$ are independently a cleavable peptide linker. In embodiments, $L^{3C}$ is a cleavable peptide linker. In embodiments, $L^{3C}$ includes a modified amino acid residue. In embodiments, $L^{3C}$ includes a modified lysine residue. In embodiments, $L^{3C}$ includes an acetylated lysine residue. In embodiments, $L^{3C}$ includes a sequence of SEQ ID NO:16 (KSADASK).

In embodiments, $L^3$ has the formula:

(IIA).

$L^{3A.1}$, $L^{3B.1}$, $L^{3C.1}$, $L^{3A.2}$, $L^{3B.2}$ and $L^{3C.2}$ are independently a bond, —O—, —S—, —C(O)—, —C(O)O—, —C(O)

NH—, —S(O)$_2$NH—, —NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene, a peptide linker or a cleavable peptide linker. In embodiments, $L^{3A.1}$, $L^{3B.1}$ $L^{3C.1}$, $L^{3A.2}$, $L^{3B.2}$ and $L^{3C.2}$ are independently substituted or unsubstituted (e.g., 2-30 membered) heteroalkylene. In embodiments, $L^{3A.1}$, $L^{3B.1}$, $L^{3C.1}$, $L^{3A.2}$, $L^{3B.2}$ and $L^{3C.2}$ are independently a peptide linker. In embodiments, $L^{3A.1}$, $L^{3B.1}$, $L^{3C.1}$, $L^{3A.2}$, $L^{3B.2}$ and $L^{3C.2}$ are independently a cleavable peptide linker. In embodiments, $L^{3A.1}$ and $L^{3A.2}$ are independently:

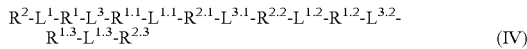

(IV)

In formula (IV), $R^1$, $L^1$, $R^2$, $L^3$, $L^{3.1}$, $L^{3.2}$, $R^{1.1}$, $L^{1.1}$, $R^{2.1}$, $R^{1.2}$, $L^{1.2}$, $R^{2.2}$, $R^{1.3}$, $L^{1.3}$ and $R^{2.3}$ are as described herein. For example, $L^3$, $L^{3.1}$ and $L^{3.2}$ are chemical linkers; $R^1$, $R^{1.1}$, $R^{1.2}$ and $R^{1.3}$ are the peptidyl moiety of the first, second, third and fourth mechanically interlocked complex, respectively; $R^2$, $R^{2.1}$, $R^{2.2}$ and $R^{2.3}$ are the steric hindering chemical moiety of the first, second, third and fourth mechanically interlocked complex, respectively; and $L^1$, $L^{1.1}$, $L^{1.2}$ and $L^{1.3}$ are the chemical linkers of the first, second, third and fourth mechanically interlocked complex, respectively.

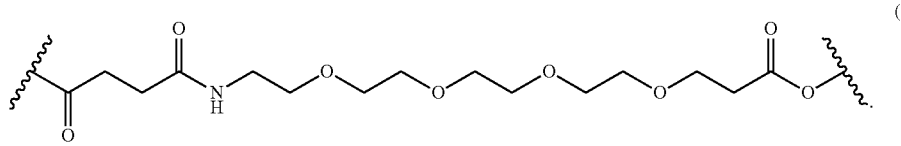

(IIB)

In formula (IIB), the point of attachment on the right side of $L^{3A.1}$ connects to $L^{3B.1}$ and the point of attachment on the left side of $L^{3A.1}$ binds to $R^2$. In formula (IIB), the point of attachment on the right side of $L^{3A.2}$ connects to $R^{2.1}$ and the point of attachment on the left side of $L^{3A.2}$ binds to $L^{3B.2}$.

In embodiments, $L^{3B.1}$ and $L^{3B.2}$ are independently —C(O)NH—. In embodiments, $L^{3C.1}$ and $L^{3C.2}$ are independently a peptide linker. In embodiments, $L^{3C.1}$ and $L^{3C.2}$ independently include the sequence of SEQ ID NO: 16 (KSADASK). In one embodiment, $L^{3A.1}$ and $L^{3A.2}$ have the structure of formula (IIB), $L^{3B.1}$ and $L^{3B.2}$ are —C(O)NH—, $L^{3C.1}$ is a peptide linker of SEQ ID NO:16 and $L^{3C.2}$ is a bond.

Figure 3C:
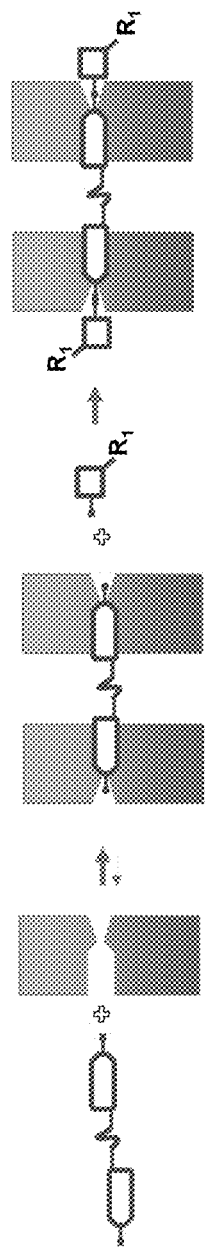

In embodiments, the chemical linker connects the Fab binding domain of the first mechanically interlocked complex to the Fab binding domain of the second mechanically interlocked complex (e.g., FIG. 3C). In embodiments, the linked mechanically interlocked complex has the formula:

$R^2$-$L^1$-$R^1$-$L^3$-$R^{1.1}$-$L^{1.1}$-$R^{2.1}$ (III)

In formula (III), $R^1$, $L^1$, $R^2$, $L^3$, $R^{1.1}$, $L^1$, $R^{2.1}$ are as described herein. For example, $L^3$ is a chemical linker, $R^1$ is the peptidyl moiety of the first mechanically interlocked complex, $L^1$ is a chemical linker of the first mechanically interlocked complex, $R^2$ is the steric hindering chemical moiety of the first mechanically interlocked complex, $R^{1.1}$ is the peptidyl moiety of the second mechanically interlocked complex, $L^{1.1}$ is the chemical linker of the second mechanically interlocked complex and $R^{2.1}$ is the steric hindering chemical moiety of the first mechanically interlocked complex.

Figure 3D:
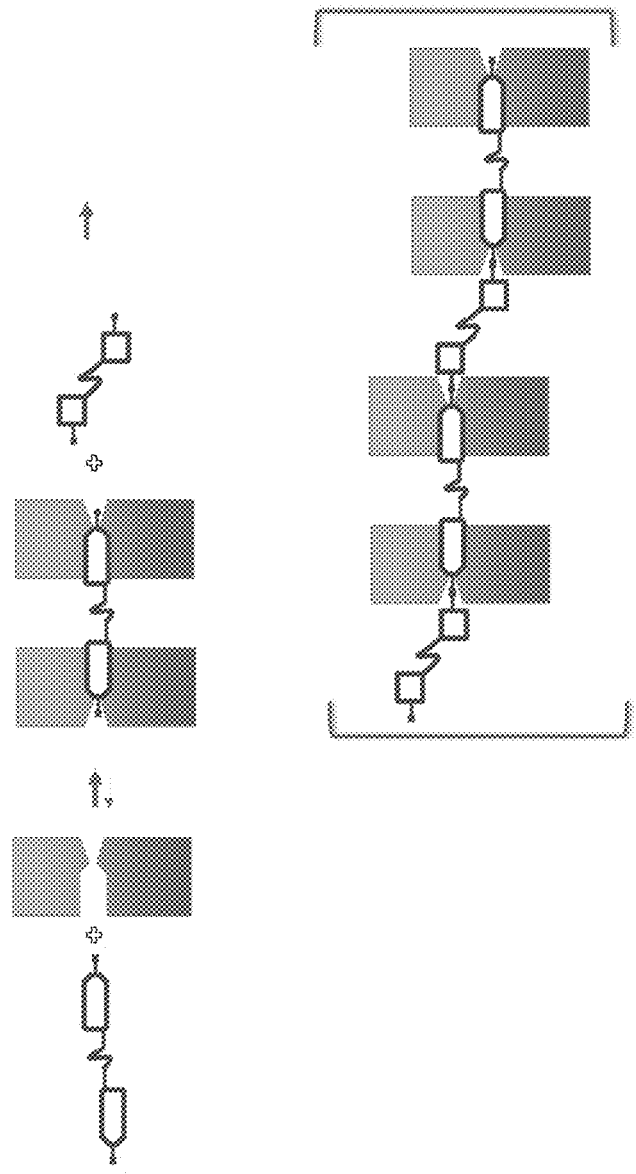
Figure 3E:
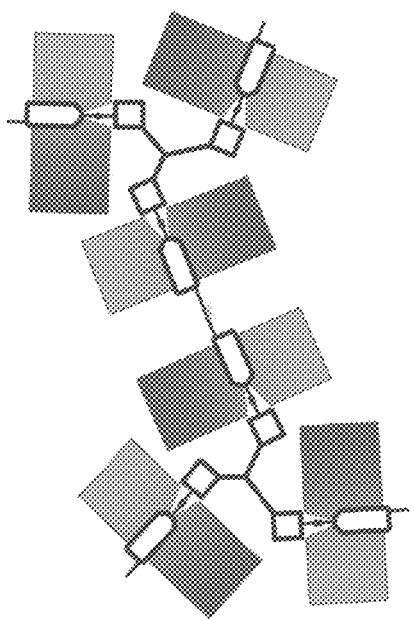
Figure 3F:
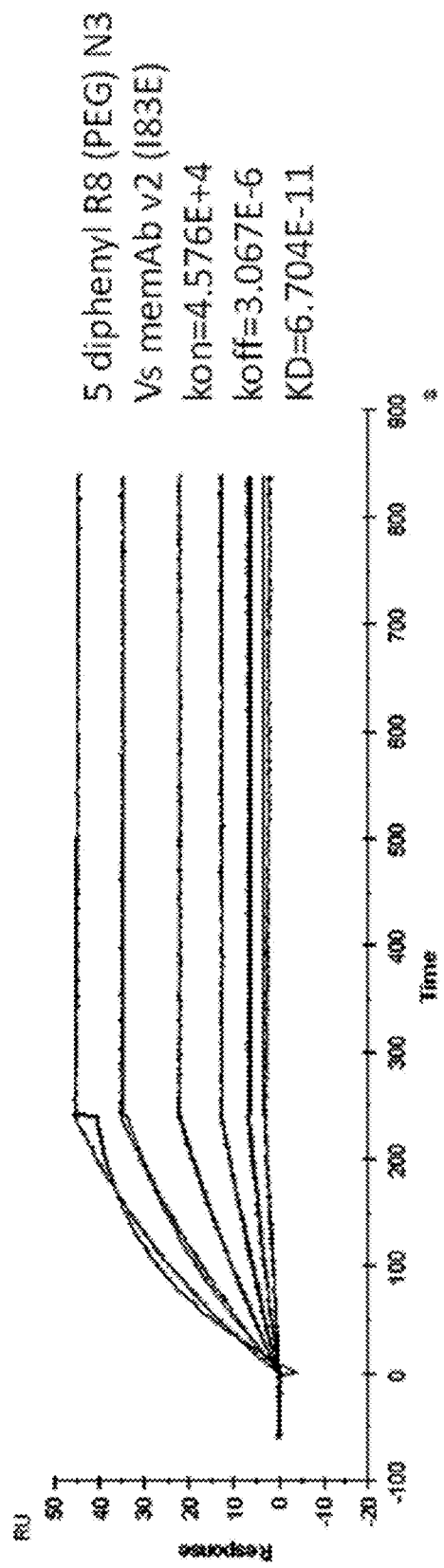

In embodiments, a first chemical linker (e.g., $L^3$) connects the Fab binding domain of the first mechanically interlocked complex to the Fab binding domain of the second mechanically interlocked complex, a second chemical linker (e.g., $L^{3.1}$) connects the steric hindering chemical moiety of the second mechanically interlocked complex to the steric hindering chemical moiety of a third mechanically interlocked complex and a third chemical linker (e.g., $L^{3.2}$) connects the Fab binding domain of the third mechanically interlocked complex to the Fab binding domain of a forth mechanically interlocked complex (e.g., FIG. 3D). Thus, in embodiments, the linked mechanically interlocked complex has the formula:

Linked Masking Peptide Moieties

As described as described herein the steric hindering chemical ments, L³ᴬ has the structure of formula (IIB). In embodiments, L³ᴮ, L³ᶜ and L³ᴰ are independently a peptide linker. In embodiments, L³ᴮ, L³ᶜ and L³ᴰ are independently a cleavable peptide linker. In embodiments, L³ᴮ includes the sequence of SEQ ID NO:17 (SSGTGGSGSGK). In embodiments, L³ᶜ includes the sequence of SEQ ID NO:18 (SGRSDNHG). In embodiments, L³ᴰ includes the sequence of SEQ ID NO:19 (GSSGGSGGSGGSGL). In embodiments, the masking peptide moiety includes the sequence of

SEQ ID NO: 20
(QGQSGQCISPRGCPDGPYVMYGSSGGSGGSGGSGLSGRSDNHGSSGTGG
SGSGK).

A "masking peptide" as provided herein refers to a peptide capable of binding to, or otherwise exhibiting an affinity for, the paratope or antigen-binding site of the Fab domain. When non-covalently bound to the antigen binding site (paratope), the masking peptide inhibits (e.g. decreases) or otherwise prevents (masks) the activity or binding of the paratope to its cognate receptor or protein (e.g., EGFR, CTLA-4). The masking peptide exhibits sufficient affinity for the paratope to prevent the activity or binding of the paratope to its antigen. Methods for determining the extent of binding of a paratope to its antigen are well known in the art.

In embodiments, the masking peptide has a length of at least 4 amino acids. In embodiments, the masking peptide is a circular peptide. In embodiments, the circularized peptide is a 12-mer. Where the masking peptide is a circularized peptide, a circularized peptide is formed by a di-sulfide bond connecting two cysteine amino acid residues. In some embodiments, the cysteine amino acid residues are terminal cysteines (i.e., are located at the N-terminus and/or the C-terminus of the masking peptide). In embodiments, the di-sulfide bond connects an N-terminal cysteine with a C-terminal cysteine.

In embodiments, the masking peptide includes a sequence having about 90% homology to SEQ ID NO:1 (QGQSGQ-CISPRGCPDGPYVMY). In embodiments, the sequence has at least 90% homology to SEQ ID NO:1. In embodiments, the sequence has at least 80% homology to SEQ ID NO: 1. In embodiments, the sequence has at least 70% homology to SEQ ID NO:1. In embodiments, the sequence has at least 60% homology to SEQ ID NO:1. In embodiments, the sequence is SEQ ID NO: 1. In embodiments, the sequence has about 70%, 75%, 80%, 85%, 90%, 91%, 92%, 93%, 94%, 95%, 96%, 97%, 98%, 99% or 100% homology to SEQ ID NO:1.

In embodiments, the masking peptide includes a sequence having about 90% homology to SEQ ID NO:2. In embodiments, the sequence has at least 90% homology to SEQ ID NO:2. In embodiments, the sequence has at least 80% homology to SEQ ID NO:2. In embodiments, the sequence has at least 70% homology to SEQ ID NO:2. In embodiments, the sequence has at least 60% homology to SEQ ID NO:2. In embodiments, the sequence is SEQ ID NO:2. In embodiments, the sequence has about 70%, 75%, 80%, 85%, 90%, 91%, 92%, 93%, 94%, 95%, 96%, 97%, 98%, 99% or 100% homology to SEQ ID NO:2.

In embodiments, the masking peptide includes a sequence having about 90% homology to SEQ ID NO:3. In embodiments, the sequence has at least 90% homology to SEQ ID NO:3. In embodiments, the sequence has at least 80% homology to SEQ ID NO:3. In embodiments, the sequence has at least 70% homology to SEQ ID NO:3. In embodiments, the sequence has at least 60% homology to SEQ ID NO:3. In embodiments, the sequence is SEQ ID NO:3. In embodiments, the sequence has about 70%, 75%, 80%, 85%, 90%, 91%, 92%, 93%, 94%, 95%, 96%, 97%, 98%, 99% or 100% homology to SEQ ID NO:3.

In embodiments, the masking peptide includes a sequence having about 90% homology to SEQ ID NO:4. In embodiments, the sequence has at least 90% homology to SEQ ID NO:4. In embodiments, the sequence has at least 80% homology to SEQ ID NO:4. In embodiments, the sequence has at least 70% homology to SEQ ID NO:4. In embodiments, the sequence has at least 60% homology to SEQ ID NO:3. In embodiments, the sequence is SEQ ID NO:4. In embodiments, the sequence has about 70%, 75%, 80%, 85%, 90%, 91%, 92%, 93%, 94%, 95%, 96%, 97%, 98%, 99% or 100% homology to SEQ ID NO:4.

In embodiments, the masking peptide includes a sequence having about 90% homology to SEQ ID NO:4. In embodiments, the sequence has at least 90% homology to SEQ ID NO:5. In embodiments, the sequence has at least 80% homology to SEQ ID NO:5. In embodiments, the sequence has at least 70% homology to SEQ ID NO:5. In embodiments, the sequence has at least 60% homology to SEQ ID NO:5. In embodiments, the sequence is SEQ ID NO:5. In embodiments, the sequence has about 70%, 75%, 80%, 85%, 90%, 91%, 92%, 93%, 94%, 95%, 96%, 97%, 98%, 99% or 100% homology to SEQ ID NO:5.

In embodiments, the masking peptide includes a sequence having about 90% homology to SEQ ID NO:6. In embodiments, the sequence has at least 90% homology to SEQ ID NO:6. In embodiments, the sequence has at least 80% homology to SEQ ID NO:6. In embodiments, the sequence has at least 70% homology to SEQ ID NO:6. In embodiments, the sequence has at least 60% homology to SEQ ID NO:7. In embodiments, the sequence is SEQ ID NO:6. In embodiments, the sequence has about 70%, 75%, 80%, 85%, 90%, 91%, 92%, 93%, 94%, 95%, 96%, 97%, 98%, 99% or 100% homology to SEQ ID NO:6.

In embodiments, the masking peptide includes a sequence having about 90% homology to SEQ ID NO:7. In embodiments, the sequence has at least 90% homology to SEQ ID NO:7. In embodiments, the sequence has at least 80% homology to SEQ ID NO:7. In embodiments, the sequence has at least 70% homology to SEQ ID NO:7. In embodiments, the sequence has at least 60% homology to SEQ ID NO:7. In embodiments, the sequence is SEQ ID NO:7. In embodiments, the sequence has about 70%, 75%, 80%, 85%, 90%, 91%, 92%, 93%, 94%, 95%, 96%, 97%, 98%, 99% or 100% homology to SEQ ID NO:7.

In embodiments, the masking peptide includes a sequence having about 90% homology to SEQ ID NO:8. In embodiments, the sequence has at least 90% homology to SEQ ID NO:8. In embodiments, the sequence has at least 80% homology to SEQ ID NO:8. In embodiments, the sequence has at least 70% homology to SEQ ID NO:8. In embodiments, the sequence has at least 60% homology to SEQ ID NO:8. In embodiments, the sequence is SEQ ID NO:8. In embodiments, the sequence has about 70%, 75%, 80%, 85%, 90%, 91%, 92%, 93%, 94%, 95%, 96%, 97%, 98%, 99% or 100% homology to SEQ ID NO:8.

In embodiments, the masking peptide includes a sequence having about 90% homology to SEQ ID NO:9. In embodiments, the sequence has at least 90% homology to SEQ ID NO:9. In embodiments, the sequence has at least 80% homology to SEQ ID NO:9. In embodiments, the sequence has at least 70% homology to SEQ ID NO:9. In embodiments, the sequence has at least 60% homology to SEQ ID NO:9. In embodiments, the sequence is SEQ ID NO:9. In embodiments, the sequence has about 70%, 75%, 80%, 85%, 90%, 91%, 92%, 93%, 94%, 95%, 96%, 97%, 98%, 99% or 100% homology to SEQ ID NO:9.

In embodiments, the masking peptide includes a sequence having about 90% homology to SEQ ID NO: 10. In embodiments, the sequence has at least 90% homology to SEQ ID NO:10. In embodiments, the sequence has at least 80% homology to SEQ ID NO:10. In embodiments, the sequence has at least 70% homology to SEQ ID NO:10. In embodiments, the sequence has at least 60% homology to SEQ ID NO:10. In embodiments, the sequence is SEQ ID NO:10. In embodiments, the sequence has about 70%, 75%, 80%, 85%, 90%, 91%, 92%, 93%, 94%, 95%, 96%, 97%, 98%, 99% or 100% homology to SEQ ID NO:10.

In embodiments, the masking peptide includes a sequence having about 90% homology to SEQ ID NO: 11. In embodiments, the sequence has at least 90% homology to SEQ ID NO:11. In embodiments, the sequence has at least 80% homology to SEQ ID NO: 11. In embodiments, the sequence has at least 70% homology to SEQ ID NO:11. In embodiments, the sequence has at least 60% homology to SEQ ID NO:11. In embodiments, the sequence is SEQ ID NO:11. In embodiments, the sequence has about 70%, 75%, 80%, 85%, 90%, 91%, 92%, 93%, 94%, 95%, 96%, 97%, 98%, 99% or 100% homology to SEQ ID NO:11.

In embodiments, the masking peptide includes a sequence having about 90% homology to SEQ ID NO: 12. In embodiments, the sequence has at least 90% homology to SEQ ID NO:12. In embodiments, the sequence has at least 80% homology to SEQ ID NO:12. In embodiments, the sequence has at least 70% homology to SEQ ID NO:12. In embodiments, the sequence has at least 60% homology to SEQ ID NO:12. In embodiments, the sequence is SEQ ID NO:12. In embodiments, the sequence has about 70%, 75%, 80%, 85%, 90%, 91%, 92%, 93%, 94%, 95%, 96%, 97%, 98%, 99% or 100% homology to SEQ ID NO:12.

In embodiments, the masking peptide includes a sequence having about 90% homology to SEQ ID NO: 13. In embodiments, the sequence has at least 90% homology to SEQ ID NO:13. In embodiments, the sequence has at least 80% homology to SEQ ID NO:13. In embodiments, the sequence has at least 70% homology to SEQ ID NO:13. In embodiments, the sequence has at least 60% homology to SEQ ID NO:13. In embodiments, the sequence is SEQ ID NO:13. In embodiments, the sequence has about 70%, 75%, 80%, 85%, 90%, 91%, 92%, 93%, 94%, 95%, 96%, 97%, 98%, 99% or 100% homology to SEQ ID NO:13.

In embodiments, the masking peptide includes a sequence having about 90% homology to SEQ ID NO: 14. In embodiments, the sequence has at least 90% homology to SEQ ID NO:14. In embodiments, the sequence has at least 80% homology to SEQ ID NO:14. In embodiments, the sequence has at least 70% homology to SEQ ID NO:14. In embodiments, the sequence has at least 60% homology to SEQ ID NO:14. In embodiments, the sequence is SEQ ID NO:14. In embodiments, the sequence has about 70%, 75%, 80%, 85%, 90%, 91%, 92%, 93%, 94%, 95%, 96%, 97%, 98%, 99% or 100% homology to SEQ ID NO:14.

In embodiments, the masking peptide includes a sequence having about 90% homology to SEQ ID NO: 15. In embodiments, the sequence has at least 90% homology to SEQ ID NO:15. In embodiments, the sequence has at least 80% homology to SEQ ID NO:15. In embodiments, the sequence has at least 70% homology to SEQ ID NO:15. In embodiments, the sequence has at least 60% homology to SEQ ID NO:15. In embodiments, the sequence is SEQ ID NO:15. In embodiments, the sequence has about 70%, 75%, 80%, 85%, 90%, 91%, 92%, 93%, 94%, 95%, 96%, 97%, 98%, 99% or 100% homology to SEQ ID NO:15.

In embodiments, the masking peptide is any of the peptides described in Table 1.

TABLE 1

Identification of CTLA-4 masking peptide.

| Peptide No. | Sequence | SEQ ID NO: |
|---|---|---|
| 6 | CEKWFRFMC | 2 |
| 9 | CVTGFEFLC | 3 |
| 12 | CSVLPPFMC | 4 |
| 19 | CSVLLPFMC | 5 |
| 16 | CWSPLPFMC | 6 |
| 11 | CPRPLYWLC | 7 |
| 3 | CFTPWPEAC | 8 |
| 20 | CFHAPWAPC | 9 |
| 13 | CNNYKGGRC | 10 |
| 4 | CWPEWDLWC | 11 |
| 15 | CLPEISFLC | 12 |
| 2 | CRIDERLQC | 13 |
| 8 | CYLELMHSC | 14 |
| 1 | CYGLGFNFC | 15 |

In embodiments, the non-CDR binding site is a peptide binding site including framework region amino acid residues and the Fab binding moiety is a peptidyl moiety. In embodiments, the peptidyl moiety is a moiety as described in published US application US20120301400 A1, which is hereby incorporated by reference in its entirety and for all purposes.

In embodiments, the peptidyl moiety binds to the peptide binding site with a $K_D$ of less than 10 µM. In embodiments, the peptidyl moiety binds to the peptide binding site with a $K_D$ of less than 9 µM. In embodiments, the peptidyl moiety binds to the peptide binding site with a $K_D$ of less than 8 µM. In embodiments, the peptidyl moiety binds to the peptide binding site with a $K_D$ of less than 7 µM. In embodiments, the peptidyl moiety binds to the peptide binding site with a $K_D$ of less than 6 µM. In embodiments, the peptidyl moiety binds to the peptide binding site with a $K_D$ of less than 5 µM. In embodiments, the peptidyl moiety binds to the peptide binding site with a $K_D$ of less than 4 µM. In embodiments, the peptidyl moiety binds to the peptide binding site with a $K_D$ of less than 3 µM. In embodiments, the peptidyl moiety binds to the peptide binding site with a $K_D$ of less than 2 µM. In embodiments, the peptidyl moiety binds to the peptide binding site with a $K_D$ of less than 1 µM. In embodiments, the peptidyl moiety binds to the peptide binding site with a $K_D$ of less than 0.5 µM. In embodiments, the peptidyl moiety binds to the peptide binding site with a $K_D$ of less than 100 nM. In embodiments, the peptidyl moiety binds to the peptide binding site with a $K_D$ of less than 90 nM. In embodiments, the peptidyl moiety binds to the peptide binding site with a $K_D$ of less than 80 nM. In embodiments, the peptidyl moiety binds to the peptide binding site with a $K_D$ of less than 70 nM. In embodiments, the peptidyl moiety binds to the peptide binding site with a $K_D$ of less than 60 nM. In embodiments, the peptidyl moiety binds to the peptide binding site with a $K_D$ of less than 50 nM. In embodiments, the peptidyl moiety binds to the peptide binding site with a $K_D$ of less than 10 nM. In embodiments, the peptidyl moiety binds to the peptide binding site with a $K_D$ of less than 1 nM.

In embodiments, the peptidyl moiety binds to the peptide binding site with a $\tau_{1/2}$ of more than 200 seconds. In embodiments, the peptidyl moiety binds to the peptide binding site with a $\tau_{1/2}$ of more than 500 seconds. In embodiments, the peptidyl moiety binds to the peptide binding site with a $\tau_{1/2}$ of more than 1000 seconds. In embodiments, the peptidyl moiety binds to the peptide binding site with a $\tau_{1/2}$ of more than 2000 seconds. In embodiments, the compound and the Fab are bound together with a $\tau_{1/2}$ of more than 4000 seconds. In embodiments, the compound and said Fab are bound together with a $\tau_{1/2}$ of more than 4500 seconds.

In embodiments, the compound is conjugated to a therapeutic agent, a diagnostic agent, or a detectable agent. In embodiments, the Fab binding moiety is conjugated to a therapeutic agent, a diagnostic agent, or a detectable agent.

In embodiments, the compound has the formula: $R^1$-$L^1$-$R^2$, wherein $R^1$ is the peptidyl moiety; $L^1$ is the chemical linker of about 5 Å to about 15 Å in length; and $R^2$ is the steric hindering chemical moiety wherein the longest bond length distance is at least 8 A.

In embodiments, the chemical linker is a covalent linker. In embodiments, the chemical linker is a substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene. In embodiments, the chemical linker is a PEG linker. In embodiments, the chemical linker is a hydrocarbon linker. In embodiments, the chemical linker is a cleavable peptide linker.

In embodiments, $R^1$ is:

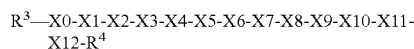

wherein X0 is Ser or null; X1 is Cys, Ser, Gly, β-alanine, diaminopropionic acid, β-azidoalanine, or null; X2 is Gln or null; X3 is Phe, Tyr, β,β'-diphenyl-Ala, His, Asp, 2-bromo-L-phenylalanine, 3-bromo-Lphenylalanine, 4-bromo-L-phenylalanine, Asn, Gln, a modified Phe, a hydratable carbonyl-containing residue, or a boronic acid-containing residue; X4 is Asp or Asn; X5 is Leu, β,β'-diphenyl-Ala, Phe, Trp, Tyr, a non-natural analog of phenylalanine, tryptophan, or tyrosine, a hydratable carbonyl-containing residue, or a boronic acid-containing residue; X6 is Ser or Cys; X7 is Thr, Ser or Cys; X8 is an amino acid including a side chain of the formula -$L^{1,4}$-$L^1$-$R^2$, wherein $L^{1,4}$ is a bond, —O—, —S—, —C(O)—, —C(O)O—, —C(O)NH—, —S(O)$_2$NH—, —NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene; X9 is Arg or Ala; X10 is Leu, Gln, Glu, β,β'-diphenyl-Ala, Phe, Trp, Tyr; a non-natural analog of phenylalanine, tryptophan, or tyrosine, a hydratable carbonyl-containing residue, or a boronic acid-containing residue; X11 is Lys or Arg; X12 is Cys, Gly, 7-aminoheptanoic acid, β-alanine, diaminopropionic acid, propargylglycine, isoaspartic acid, or null, $R^3$ and $R^4$ are independently null, -$L^2$-$R^5$ or an amino acid peptide sequence optionally substituted with -$L^2$-$R^5$, wherein $L^2$ is a covalent or non-covalent linker and $R^5$ is a therapeutic agent, a diagnostic agent, or a detectable agent; and wherein X1 and X12 are optionally joined together to form a cyclic peptidyl moiety. $L^2$ and $L^1$ may be a chemical linker as defined herein. Thus, $L^2$ and $L^1$ may be a covalent linker. $L^2$ and $L^1$ may include the resulting linker formed by reacting two reactive groups (moieties), e.g., a covalent reactive group, as described herein (e.g., alkyne, thiol, azide, maleimide). $L^2$ and $L^1$ may be a cleavable peptide linker as described herein.

In embodiments, X1 and X2 are Cys and are joined together through a disulfide bond to form a cyclic peptidyl moiety. Various methods for cyclization of a peptide moiety may be used, e.g., to address in vivo stability and to enable chemoselective control for subsequent conjugation chemistry. In some embodiments, the cyclization strategy is a lactam cyclization strategy, including head-to-tail (head-tail) lactam cyclization (between the terminal residues of the acyclic peptide) and/or lactam linkage between other residues. Lactam formation may also be effected by incorporating residues such as glycine, β-Ala, and/or 7-aminoheptanoic acid, and the like, into the acyclic peptide cyclization precursors to produce different lactam ring sizes and modes of connectivity. Additional cyclization strategies such as "click" chemistry and olefin metathesis also can be used. Such methods of peptide and peptidomimetic cyclization are well known in the art.

In embodiments, X0 is null. In embodiments, X2 is Gln. In embodiments, X5 is β,β'-diphenyl-Ala. In embodiments, $L^{1,4}$ is —(CH$_2$)$_3$—NH(N)—NH—. In embodiments, $R^3$ and $R^4$ are independently null, -$L^2$-$R^5$ or a 1 to 100 amino acid peptide sequence optionally substituted with -$L^2$-$R^5$, wherein $L^2$ is a covalent or non-covalent linker and $R^5$ is a therapeutic agent, a diagnostic agent, or a detectable agent. In embodiments, $R^3$ is -$L^2$-$R^5$ or an amino acid peptide sequence optionally substituted with -$L^2$-$R^5$, and $R^4$ is null. In embodiments, $R^3$ is a three amino acid peptide sequence optionally substituted with -$L^2$-$R^5$. In embodiments, $R^3$ is Lys-Gly-Gly-optionally substituted with -$L^2$-$R^5$.

In embodiments, the non-CDR binding site is formed by amino acids at positions 8, 9, 10, 38, 39, 40, 4142, 43, 44, 45, 82, 83, 84, 85, 86, 87, 99, 100, 101, 102, 103, 104, 105, 142, 162, 163, 164, 165, 166, 167, 168, and 173 of the light chain and 6, 9, 38, 39, 40, 41, 42, 43, 44, 45, 84, 86, 87, 88, 89, 90, 91, 103, 104, 105, 106, 107, 108, 111, 110, 147, 150, 151, 152, 173, 174, 175, 176, 177, 185, 186, and 187 of the heavy chain of the Fab, according to Kabat numbering. In embodiments, the Fab includes a Glu at position 83, according to Kabat numbering. In embodiments, the Fab includes a Thr or Ser at position 40, according to Kabat numbering. In embodiments, the Fab includes an Asn at position 41, according to Kabat numbering. In embodiments, the Fab includes an Asp or Asn at position 85, according to Kabat numbering.

Compounds

Provided herein, are peptide compounds capable of binding a Fab domain of an antibody or antibody fragment and chemically interlocking with a steric hindering chemical moiety provided herein. In one aspect a compound of formula:

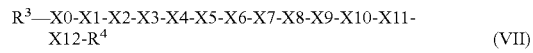

is provided. In formula (VII) X0 is Ser or null. X1 is Cys, Ser, Gly, β-alanine, diaminopropionic acid, β-azidoalanine, or null. X2 is Gln or null. X3 is Phe, Tyr, β,β'-diphenyl-Ala, His, Asp, 2-bromo-L-phenylalanine, 3-bromo-Lphenylalanine, 4-bromo-L-phenylalanine, Asn, Gln, a modified Phe, a hydratable carbonyl-containing residue, or a boronic acid-containing residue. X4 is Asp or Asn. X5 is Leu, β,β'-diphenyl-Ala, Phe, Trp, Tyr, a non-natural analog of phenylalanine, tryptophan, or tyrosine, a hydratable carbonyl-containing residue, or a boronic acid-containing residue. X6 is Ser or Cys. X7 is Thr, Ser or Cys. X8 is an amino acid including a side chain of the formula -$L^{1A}$-$L^1$-$R^2$, wherein $L^{1A}$ is a bond, —O—, —S—, —C(O)—, —C(O)O—, —C(O)NH—, —S(O)$_2$NH—, —NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene. X9 is Arg or Ala. X10 is Leu, Gln, Glu, β,β'-diphenyl-Ala, Phe, Trp, Tyr, a non-natural analog of phenylalanine, tryptophan, or tyrosine; a hydratable carbonyl-containing residue; or a boronic acid-containing residue. X11 is Lys or Arg. X12 is Cys, Gly, 7-aminoheptanoic acid, β-alanine, diaminopropionic acid, propargylglycine, isoaspartic acid, or null. $L^1$ is a chemical linker (covalent or non-covalent linker). $L^1$ provided herein may include the remnants of a chemically reactive functional group reacted with a second chemically reactive functional group, thereby forming a covalent linker. In embodiments, $L^1$ is a bond, —O—, —S—, —C(O)—, —C(O)O—, —C(O)NH—, —S(O)$_2$NH—, —NH—, —NHC(O)NH—, unsubstituted alkylene, unsubstituted heteroalkylene, unsubstituted cycloalkylene, unsubstituted heterocycloalkylene, unsubstituted arylene or unsubstituted heteroarylene. $R^2$ is a steric hindering chemical moiety. $R^3$ and $R^4$ are independently null, -$L^2$-$R^5$ or an amino acid peptide sequence optionally substituted with -$L^2$-$R^5$, wherein $L^2$ is a covalent or non-covalent linker (chemical linker) and $R^5$ is a therapeutic agent, a diagnostic agent, or a detectable agent, and wherein X1 and X12 are optionally joined together to form a cyclic peptidyl moiety. As described above, $L^2$ and $L^1$ may be a chemical linker as defined herein. Thus, $L^2$ and $L^1$ may be a covalent linker. $L^2$ and $L^1$ may include a chemically reactive functional group to react with a second chemically reactive functional group thereby forming a covalent linker. $L^2$ and $L^1$ may include the resulting linker formed by reacting two reactive groups (moieties), e.g., a covalent reactive group, as described herein (e.g., alkyne, thiol, azide, maleimide). $L^2$ and $L^1$ may be a cleavable peptide linker as described herein.

In embodiments, the steric hindering chemical moiety (also referred to herein as $R^2$) is orthogonally bound to $L^1$. Thus, the steric hindering chemical moiety and $L^1$ may form a rectangular angle. In embodiments, $L^1$ is of about 5 Å to about 15 Å in length. In embodiments, $L^1$ is of about 5 Å to about 14 Å in length. In embodiments, $L^1$ is of about 5 Å to about 13 Å in length. In embodiments, $L^1$ is of about 5 Å to about 12 Å in length. In embodiments, $L^1$ is of about 5 Å to about 11 Å in length. In embodiments, $L^1$ is of about 5 Å to about 10 Å in length. In embodiments, $L^1$ is of about 5 Å to about 9 Å in length. In embodiments, $L^1$ is of about 5 Å to about 8 Å in length. In embodiments, $L^1$ is of about 5 Å to about 7 Å in length. In embodiments, $L^1$ is of about 5 Å to about 6 Å in length. In embodiments, $L^1$ is about 5, 6, 7, 8, 9, 10, 11, 12, 13, 14, or 15 Å in length. In embodiments, $L^1$ is about at least 5 Å in length. In embodiments, $L^1$ is less than about 15 Å in length.

In embodiments, $R^2$ is a steric hindering chemical moiety, wherein the longest bond length distance is at least 8 Å. In embodiments, the longest bond length distance is about 8 Å. In embodiments, the longest bond length distance is about 9 Å. In embodiments, the longest bond length distance is about 10 Å. In embodiments, the longest bond length distance is about 11 Å. In embodiments, the longest bond length distance is about 12 Å. In embodiments, the longest bond length distance is about 13 Å. In embodiments, the longest bond length distance is about 14 Å. In embodiments, the longest bond length distance is about 15 Å.

In embodiments, $R^3$ and $R^4$ are -$L^2$-$R^5$, wherein $L^2$ is a covalent or non-covalent linker and $R^5$ is a therapeutic agent. In embodiments, $R^3$ and $R^4$ are -$L^2$-$R^5$, wherein $L^2$ is a covalent or non-covalent linker and $R^5$ is a diagnostic agent. In embodiments, $R^3$ and $R^4$ are -$L^2$-$R^5$, wherein $L^2$ is a covalent or non-covalent linker and $R^5$ is a detectable agent, and wherein X1 and X12 are optionally joined together to form a cyclic peptidyl moiety.

In embodiments, the compound has the formula:

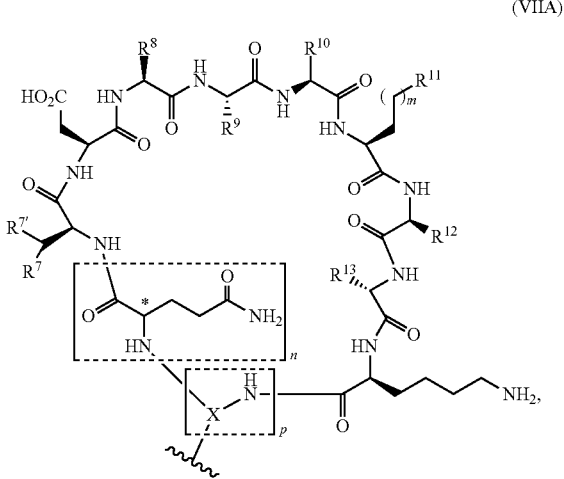

(VIIA)

In formula (VIIA), $R^7$ is hydrogen, $R^{7A}$-substituted or unsubstituted aryl, wherein $R^{7A}$ is hydrogen, halogen or $C_{1-4}$ unsubstituted alkyl. $R^{7'}$ is hydrogen, $R^{7A'}$-substituted or unsubstituted aryl, wherein $R^{7A'}$ is hydrogen, halogen or $C_{1-4}$ unsubstituted alkyl. $R^8$ is $R^{8A}$-substituted or unsubstituted $C_{1-8}$ alkyl. $R^{8A}$ is oxo, acetal, ketal, —B(OH)$_2$, boronic ester, phosphonate ester, ortho ester, —CO$_2$C$_{1-4}$alkyl, —CH=CH—CHO, —CH=CH—C(O)R$^{8A'}$, —CH=CH—CO$_2$R$^{8A'}$, —CO$_2$H, —CONH$_2$, or $R^{8B}$-substituted or unsubstituted aryl, wherein $R^{8B}$ is —OH, fluoro, chloro, bromo or iodo, and $R^{8A'}$ is substituted or unsubstituted $C_{1-4}$ alkyl. $R^9$ is -$L^{9'}$OH or -$L^{9'}$SH, wherein $L^{9'}$ is substituted or unsubstituted C$_{1-4}$ alkylene (e.g., unsubstituted C$_{1-4}$ alkylene). $R^{10}$ is -$L^{10'}$ OH or -$L^{10'}$ SH, wherein $L^{10'}$ is substituted or unsubstituted C$_{1-4}$ alkyl (e.g., unsubstituted C$_{1-4}$ alkylene). The symbol m is 0, 1, 2, 3, 4, or 5.

In formula (VIIA), $R^{11}$ is —OH, —NR$^a$R$^b$, —N(R$^c$)C(O) R$^e$, or —N(R$^c$)C(=NR$^d$)R$^e$. R$^a$ is H. R$^b$ is H or C$_{1-8}$ alkyl optionally substituted with one or more substituents selected from the group consisting of oxo, acetal, and ketal, —B(OH)$_2$, —SH, boronic ester, phosphonate ester, ortho ester, —CH=CH—CHO, —CH=CH—C(O)C$_{1-4}$ alkyl, —CH=CH—CO$_2$C$_{1-4}$ alkyl, —CO$_2$H, or —CO$_2$C$_{1-4}$ alkyl group. R$^c$ is H, C$_{1-8}$ alkyl, C$_{3-8}$ cycloalkyl, branched alkyl, or aryl. R$^d$ is H or a C$_{1-8}$ alkyl, C$_{2-8}$ alkenyl, C$_{2-8}$ alkynyl, C$_{3-8}$ cycloalkyl, branched alkyl, or aryl group, each optionally substituted with one or more substituents selected from the group consisting of —N$_3$, —NH$_2$, —OH, —SH, halogen, oxo, acetal, ketal, —B(OH)$_2$, boronic ester, phosphonate ester, ortho ester, —CH=CH—CHO, —CH=CH—C(O)C$_{1-4}$ alkyl, —CH=CH—CO$_2$C$_{1-4}$ alkyl, —CO$_2$H, and —CO$_2$C$_{1-4}$ alkyl group. R$^e$ is H; —NHR$^d$; or a C$_{1-12}$ alkyl, C$_{3-8}$ cycloalkyl, C$_{2-12}$ alkenyl, C$_{2-8}$ alkynyl, or aryl group, each optionally substituted with one or more substituents selected from the group consisting of —N$_3$, —NH$_2$, —OH, —SH, oxo, C$_{2-4}$ acetal, C$_{2-4}$ ketal, —B(OH)$_2$, boronic ester, phosphonate ester, ortho ester, —CH=CH—CHO, —CH=CH—C(O)C$_{1-4}$ alkyl, —CH=CH—CO$_2$C$_{1-4}$ alkyl, and —CO$_2$C$_{1-4}$ alkyl group.

In formula (VIIA), R$^{12}$ is substituted or unsubstituted C$_{1-4}$ alkyl. R$^{13}$ is R$^{13A}$-substituted or unsubstituted C$_{1-8}$ alkyl, wherein R$^{13A}$ is oxo, acetal, ketal, —B(OH)$_2$, boronic ester, phosphonate ester, ortho ester, —CH=CH—CHO, —CH=CH—C(O)C$_{1-4}$ alkyl, —CH=CH—CO$_2$C$_{1-4}$ alkyl, —CO$_2$C$_{1-4}$ alkyl, —CO$_2$H, —CONH$_2$ group, R$^{13B}$-substituted or unsubstituted phenyl, R$^{13B}$-substituted or unsubstituted naphthyl, R$^{13B}$-substituted or unsubstituted imidazolyl, or R$^{13B}$-substituted or unsubstituted indolyl, wherein R$^{13B}$ is —OH or halogen. The symbol n is 0 or 1. The symbol p is 0 or 1.

In formula (VIIA), X is R$^X$-substituted or unsubstituted C$_{1-8}$ alkylene, R$^x$-substituted or unsubstituted C$_{2-8}$ alkenylene, R$^x$ is oxo, —C(O)—, —NH$_2$, —NHC(O)— or —NHC(O)R$^y$, wherein one carbon of the alkylene is optionally replaced with —C(O)NH—, a 5-membered heteroarylene, or —S—S—, and R$^y$ is —C$_{1-4}$ alkyl, —CH(R$^z$)C(O)— or —CH(R$^z$)CO$_2$H, wherein R$^z$ is —H or R$^{z'}$-substituted or unsubstituted —C$_{1-4}$ alkyl wherein R$^{z'}$ is —OH, —SH, or —NH$_2$. Formula (VII) or (VIIA) includes all appropriate pharmaceutically acceptable salts. In some embodiments, X is:

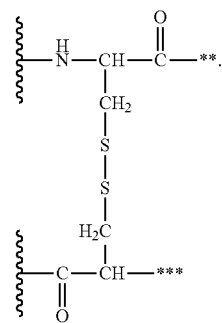

(VIIB)

In Formula (VIIB),  represents the point of attachment to the glutamine attached to X in Formula (VIIA) and * represents the point of attachment to the nitrogen attached to X and lysine in Formula (VIIA). The symbol denotes the point of attachment of X to R$^3$ and R$^4$, respectively.

In embodiments, R$^{8A}$ is phenyl, naphthyl, imidazolyl, or indolyl.

In embodiments, R$^{11}$ is a C$_{1-12}$ alkyl substituted with an oxo, acetal, ketal, —B(OH)$_2$, boronic ester, —SH, —OH, phosphonate ester, ortho ester, —CH=CH—CHO, —CH=CH—C(O)C$_{1-4}$ alkyl, —CH=CH—CO$_2$C$_{1-4}$ alkyl, or —CO$_2$C$_{1-4}$ alkyl group.

In embodiments, X is a linker resulting from any of the meditope cyclization strategies as discussed herein.

In embodiments, the compound has the structure of formula:

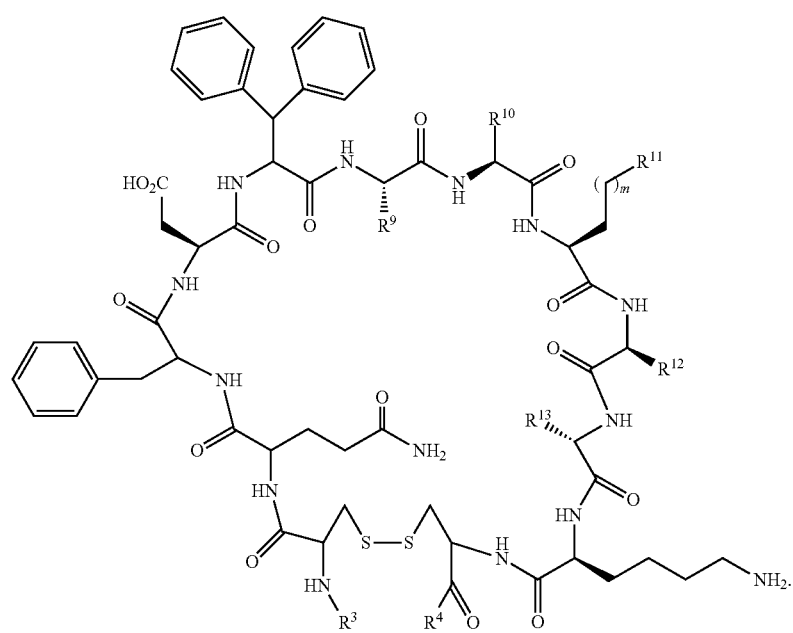

(VIIC)

In formula (VIIC) $R^3$, $R^4$, $R^9$, $R^{10}$, $R^{11}$, $R^{12}$ and $R^{13}$ are defined as described herein. $R^9$ is -$L^{9'}$OH or -$L^{9'}$SH, wherein $L^{9'}$ is substituted or unsubstituted $C_{1-4}$ alkylene (e.g., unsubstituted $C_{1-4}$ alkylene). $R^{10}$ is -$L^{10'}$OH or -$L^{10'}$SH, wherein $L^{10'}$ is substituted or unsubstituted $C_{1-4}$ alkyl (e.g., unsubstituted $C_{1-4}$ alkylene). The symbol m is 0, 1, 2, 3, 4, or 5. For example, $R^9$ is —COH, $R^{10}$ is —C(CH$_3$)OH, $R^{11}$ is -$L^{14}$-$L^1$-$R^2$, wherein $R^2$ is a steric hindering chemical moiety, $R^{12}$ is —CH$_2$CH$_2$CH$_2$NHC(NH$_2$)NH$_2^+$ and $R^{13}$ is —CH$_2$CH$_2$(CH$_3$)CH$_3$.

In embodiments, the compound has the structure of formula:

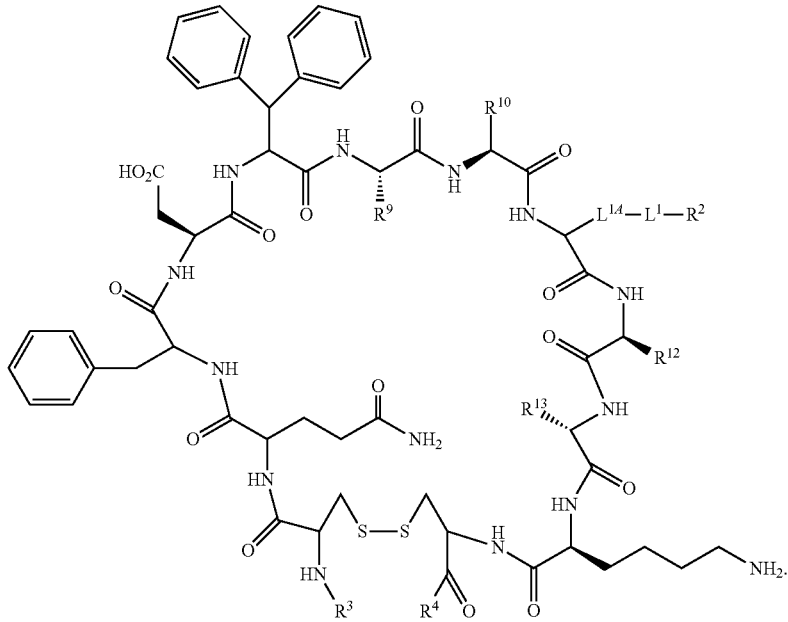

(VIID)

In formula (VIID) $R^3$, $R^4$, $R^9$, $R^{10}$, $R^{12}$ and $R^{13}$ are defined as described herein. For example, $R^9$ is —COH, $R^{10}$ is —C(CH$_3$)OH, $R^{12}$ is —CH$_2$CH$_2$CH$_2$NHC(NH$_2$)NH$_2$+ and $R^{13}$ is —CH$_2$CH$_2$(CH$_3$)CH$_3$.

In another aspect a compound having the formula:

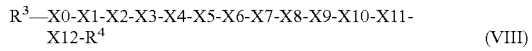

is provided. In formula (VIII) X0 is Ser or null. X1 is Cys, Ser, Gly, β-alanine, diaminopropionic acid, β-azidoalanine, or null. X2 is Gln or null. X3 is Phe, Tyr, β,β'-diphenyl-Ala, His, Asp, 2-bromo-L-phenylalanine, 3-bromo-Lphenylalanine, 4-bromo-L-phenylalanine, Asn, Gln, a modified Phe, a hydratable carbonyl-containing residue, or a boronic acid-containing residue. X4 is Asp or Asn. X5 is Leu; β,β'-diphenyl-Ala, Phe, Trp, Tyr, a non-natural analog of phenylalanine, tryptophan, or tyrosine; a hydratable carbonyl-containing residue, or a boronic acid-containing residue. X6 is Ser or Cys. X7 is Thr, Ser or Cys. X8 is an amino acid including a side chain of the formula -$L^{14}$-$L^1$-$R^6$, wherein $L^{14}$ is a bond, —O—, —S—, —C(O)—, —C(O)O—, —C(O)NH—, —S(O)$_2$NH—, —NH—, —NHC(O)NH—, substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene. X9 is Arg or Ala. X10 is Leu, Gln, Glu; β,β'-diphenyl-Ala, Phe, Trp, Tyr, a non-natural analog of phenylalanine, tryptophan, or tyrosine, a hydratable carbonyl-containing residue, or a boronic acid-containing residue. X11 is Lys or Arg and X12 is Cys, Gly, 7-aminoheptanoic acid, β-alanine, diaminopropionic acid, propargylglycine, isoaspartic acid, or null. $R^3$ and $R^4$ are independently null, -$L^2$-$R^5$ or an amino acid peptide sequence optionally substituted with -$L^2$-$R^5$, wherein $L^2$ is a covalent or non-covalent linker and $R^5$ is a therapeutic agent, a diagnostic agent, or a detectable agent. $R^6$ is a click chemistry reactive functional group and wherein X1 and X12 are optionally joined together to form a cyclic peptidyl moiety.

In embodiments, the compound has the structure of formula:

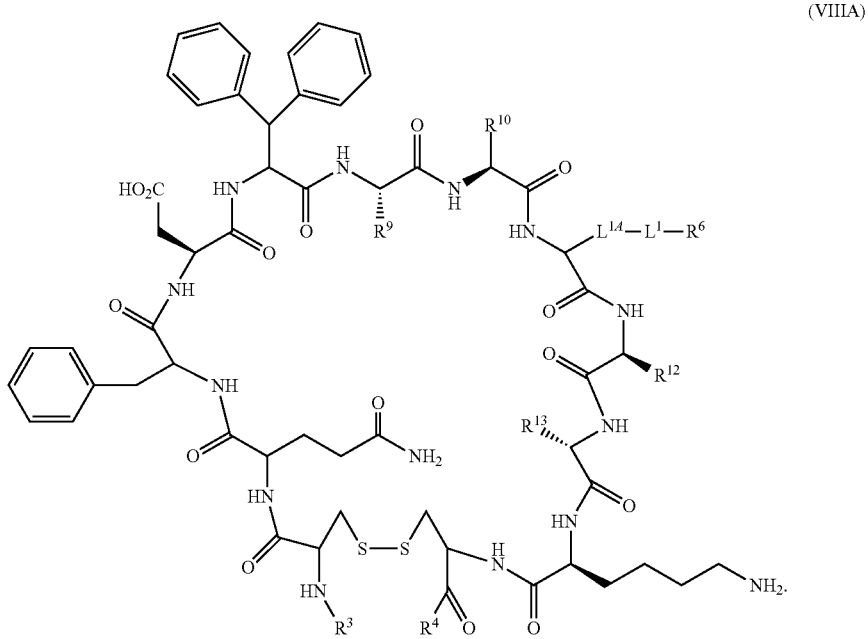

(VIIIA)

In formula (VIIIA) $R^3$, $R^4$, $R^9$, $R^{10}$, $R^{12}$ and $R^{13}$ are defined as described herein. For example, $R^6$ is an azide, an alkyne, a thiol or a maleimide reactive functional group, $R^9$ is —COH, $R^{10}$ is —C(CH$_3$)OH, $R^{12}$ is —CH$_2$CH$_2$CH$_2$NHC(NH$_2$)NH$_2^+$ and $R^{13}$ is —CH$_2$CH$_2$(CH$_3$)CH$_3$. Thus, in embodiments, $R^6$ is —N$_3$ or —SH.

In embodiments, the compound is bound to a fragment antigen-binding (Fab) domain. In embodiments, the Fab domain includes a hole within a central cavity lined (e.g., formed) by amino acid residues of the VH, VL, CH1, and CL regions of the Fab domain, wherein the central cavity includes a non-CDR binding site, wherein the compound is bound to the non-CDR binding site.

Methods

In one aspect, a method of binding an antigen is provided. The method includes contacting an antigen with the mechanically interlocked complex provided herein including embodiments thereof and allowing said Fab to bind the antigen.

In another aspect, a method of forming a mechanically interlocked complex is provided. The method includes contacting the compound provided herein with a steric hindering chemical moiety including a complementary click chemistry reactive functional group. The complementary click chemistry reactive functional group is allowed to react with the click chemistry reactive functional thereby forming a chemical linker between the steric hindering chemical moiety and the compound, wherein the chemical linker passes through the hole and steric hindrance occurs between the steric hindering chemical moiety and amino acids lining the hole thereby mechanically interlocking the compound and the Fab.

In another aspect, a method of forming a mechanically interlocked complex is provided. The method includes contacting a compound with a steric hindering chemical moiety. The steric hindering chemical moiety includes a complementary click chemistry reactive functional group and the compound includes a Fab binding moiety attached to a click chemistry reactive group. The Fab binding moiety is bound to a non-CDR binding site of a Fab domain, and the Fab domain includes a hole within a central cavity lined by amino acid residues of the VH, VL, CH1, and CL regions of the Fab domain, wherein the central cavity includes the non-CDR binding site. The complementary click chemistry reactive functional group is allowed to react with the click chemistry reactive functional group thereby forming a conjugate including a steric hindering chemical moiety linked through a chemical linker to the Fab binding moiety, wherein the chemical linker passes through the hole and steric hindrance occurs between the steric hindering chemical moiety and amino acids lining the hole thereby mechanically interlocking the compound and the Fab.

In some aspects, the antibodies include a heavy chain variable (VH) region and/or a light chain variable (VL) region. In some aspects, the VL region has an amino acid sequence comprising a threonine, serine, or aspartate at position 40, a residue other than glycine at position 41, and/or an aspartate or asparagine at position 85, according to Kabat numbering, and/or comprises an isoleucine or leucine at position 10 and isoleucine at position 83, according to Kabat numbering, and/or comprises a valine or isoleucine at position 9 and a residue other than glutamine at position 100, according to Kabat numbering. In some examples, the amino acid sequence of the VL region has a threonine at position 40, an asparagine at position 41, and an aspartate at position 85, according to Kabat numbering.

In some aspects, the VH region has an amino acid sequence comprising a serine or proline at position 40 and an isoleucine, tyrosine, methionine, phenylalanine, or tryptophan at position 89, according to Kabat numbering. In some examples, the amino acid sequence of the VH region has a serine at position 40 and an isoleucine at position 89, according to Kabat numbering.

EXAMPLES

Example 1

Based on the discovery of a unique peptide binding site within the Fab arm of cetuximab, it was sought to develop a non-covalent approach to efficiently functionalize monoclonal antibodies (mAbs). To enhance affinity of peptide-Fab interactions, structural and biophysical methods were used to introduce non-natural amino acids in the peptide and to generate specific mutations within the Fab and achieved a high affinity peptide-Fab complex. Based on the structure of the high affinity complex, it was observed that guandinium nitrogen (NH1/2) of arginine 8 in the peptide was accessible from the opposing side of the Fab. A peptide was prepared with arginine 8 modified to include a short polyethylene linker and a terminal azide. This modified peptide was allowed to bind to the Fab, and copper-free click chemistry was used to create an interlocked, mechanical bond.

Figure 4:
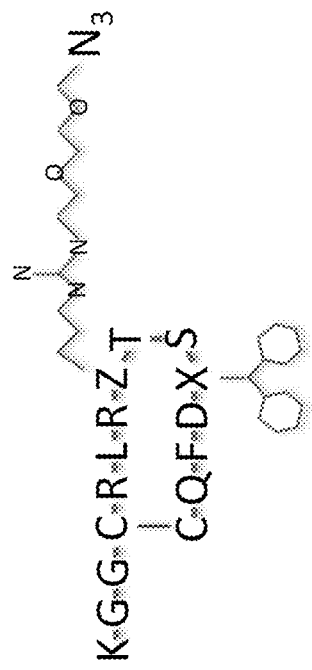
FIG. 4: Crystal structure of I83E trastuzumab memAb bound to long 8-azido-5diphenyl meditope. Left panel shows that the guandinium group (circle) of Arg is accessible from the opposite side of the mAb (based on x-ray structure). The right panel shows a close view of the 8-azido-peg-arginine extending through the Fab hole. The azide group is highlighted.
Figure 4:
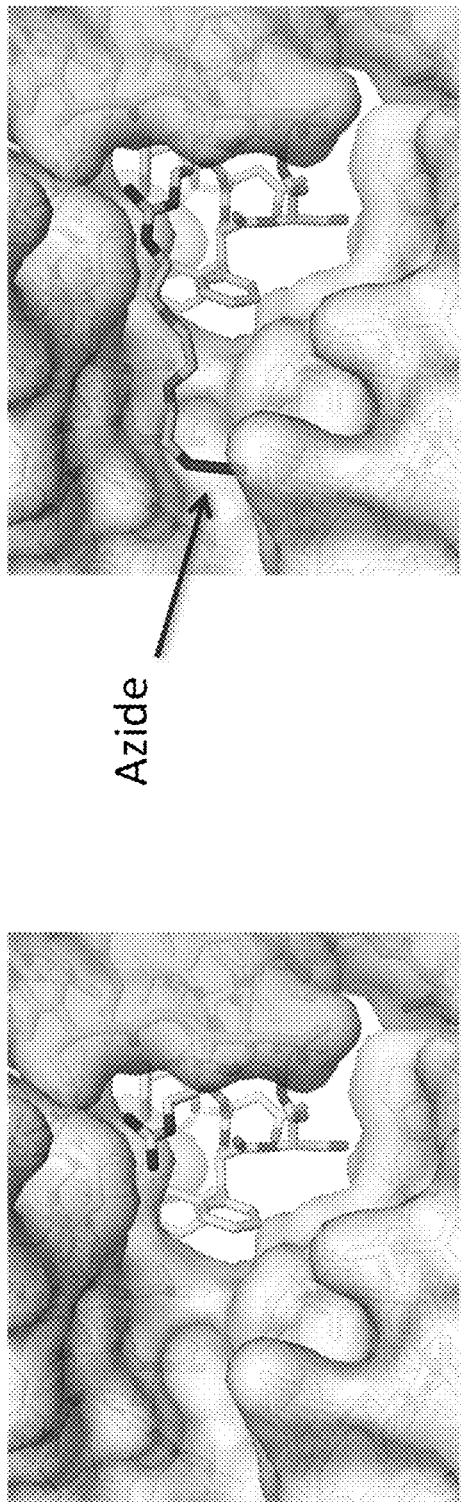
Figure 5:
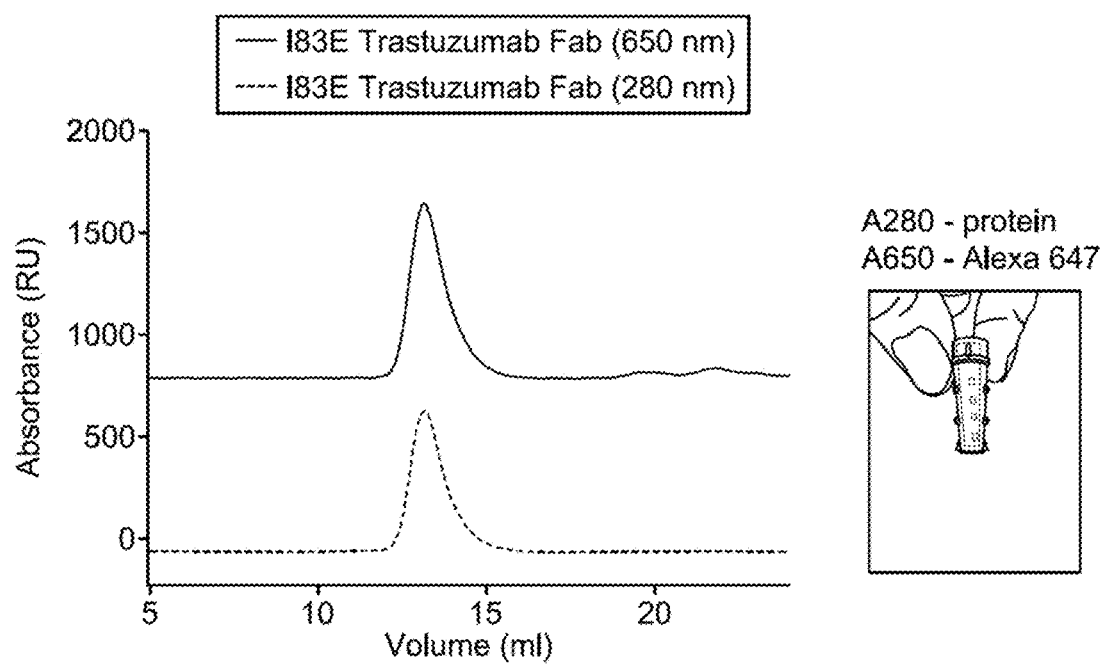
FIG. 5: I83E trastuzumab Fab contacted with azide-meditope and Alexa647-DIBO. Meditope-enabled trastuzumab Fab was mixed with 8-azido-5-diphenylalanine meditope at near stoichiometry concentrations. Alexafluor 647-DIBO was then added to the solution and allowed to react for up to 2 h. The mixture was then applied to a size exclusion chromatography column and the absorbance at 280 nm (protein) and 650 nm (Alexafluor647) was simultaneously monitored. The Alexafluor 647 signal co-migrated with the IgG, indicating that the Alexafluor647-DIBO reacted with the meditope azido group.
Figure 6:
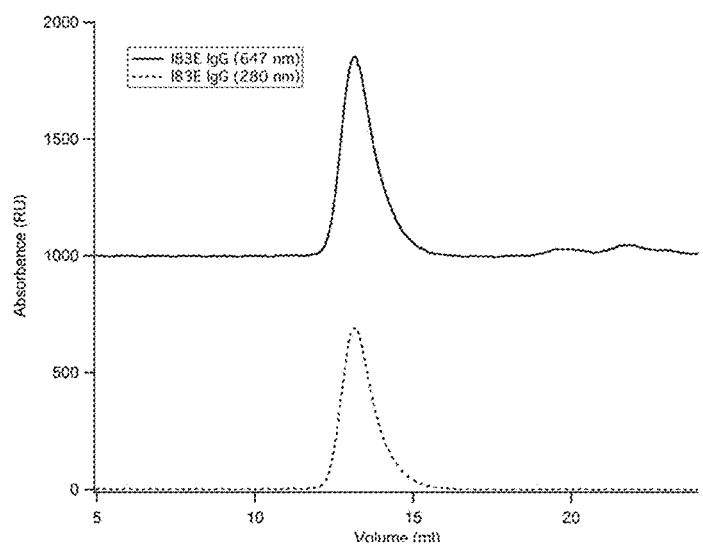
FIG. 6: I83E IgG contacted with Alexa647-DIBO. Meditope-enabled trastuzumab was mixed with 8-azido-5-diphenylalanine meditope at near stoichiometry concentrations. Alexafluor 647-DIBO was then added to the solution and allowed to react for up to 2 h. The mixture was then applied to a size exclusion chromatography column and the absorbance at 280 nm (protein) and 647 nm (Alexafluor647) was simultaneously monitored. Of note, the Alexafluor 647 signal co-migrated with the IgG, indicating that the Alexafluor647-DIBO reacted with the meditope azido group and created a mechanical bond.
Figure 7:
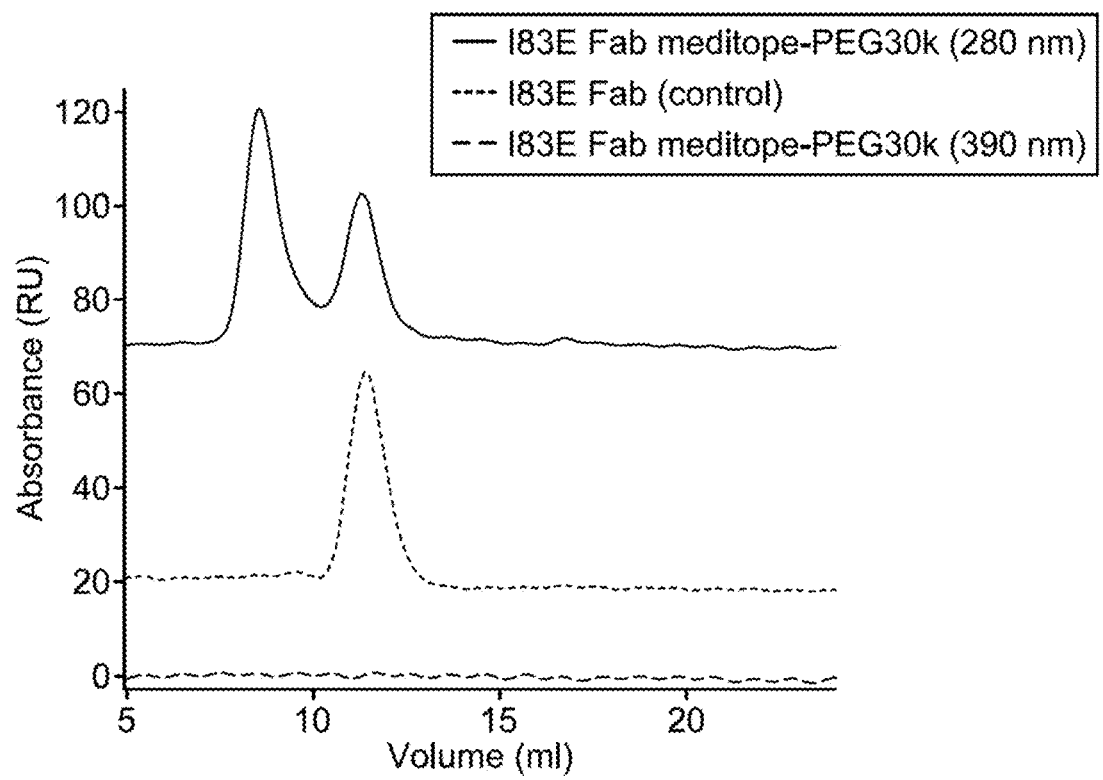
FIG. 7: I83E trastuzumab meFab contacted with DIBP-PEG 30 KDal. Meditope-enabled trastuzumab was mixed with 8-azido-5-diphenylalanine meditope at near stoichiometry concentrations. DIBO-PEG30K was then added to the solution and allowed to react for 2 h. The mixture was then applied to a size exclusion chromatography column and the absorbance at 280 nm (protein) and 390 nm (marker for unreacted DIBO-PEG30K) was simultaneously monitored. The addition of the 30 kDa PEG to the Fab (~50 kDa) results in a mass ~80 kDa. The new peak is observed that elutes earlier than the Fab (top trace) is consistent with an 80 kDa protein. Unreacted Fab (second peak) elutes at the same volume as the control Fab (middle trace). The lower trace indicates the absence of unreacted DIBO-PEG30K.
Figure 8:
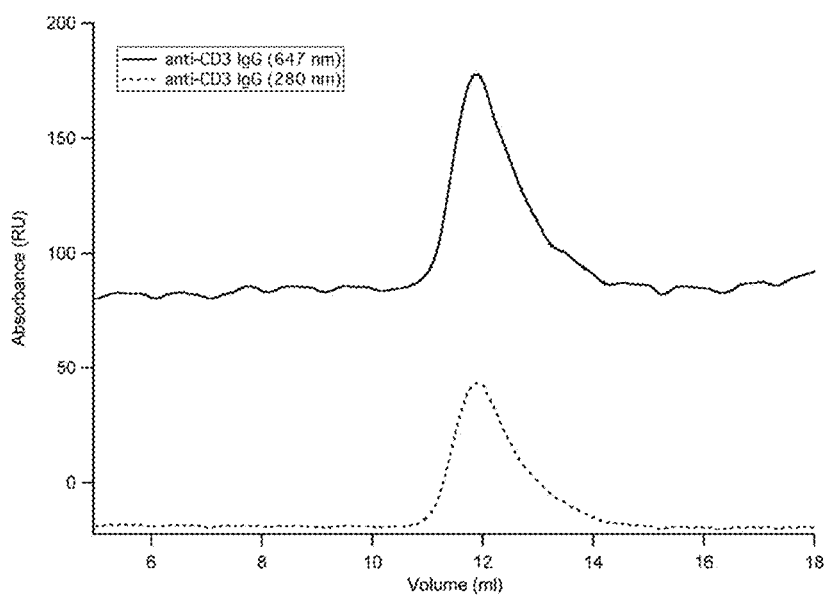
FIG. 8: Meditope-enabled anti-CD3 IgG contacted with DIBO-Alexafluor 647. The parental anti-CD3 (UCHT1) mAb was meditope-enabled, expressed and purified. The 8-azido-5-diphenylalanine meditope was added to the anti-CD3 memAb at near stoichiometry concentrations. Alexafluor 647-DIBO was then added to the solution and allowed to react for 2 h. The mixture was then applied to a size exclusion chromatography column and the absorbance at 280 nm (protein) and 647 nm (Alexafluor647) was simultaneously monitored. The Alexafluor647 signal co-migrated with the IgG, indicating that the Alexafluor647-DIBO reacted with the meditope azido group.
Figure 10:
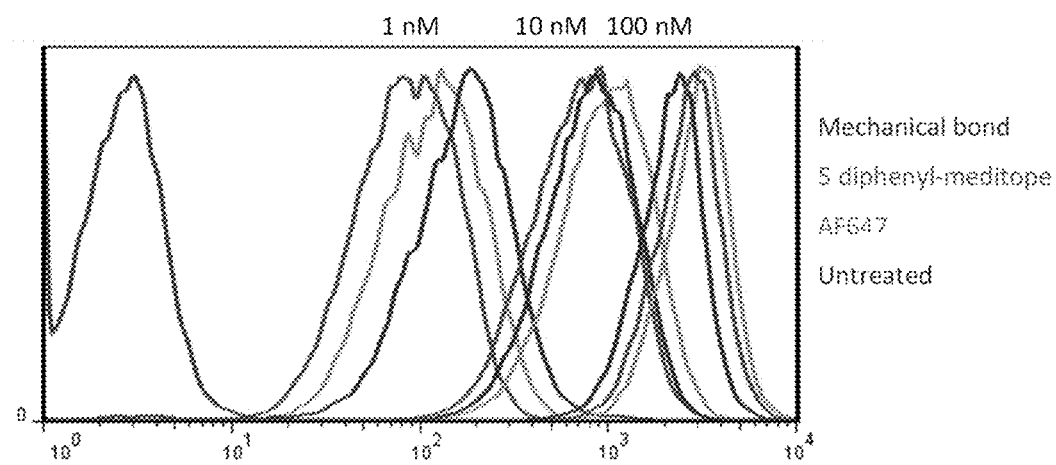
FIG. 10: Analytical Cytometry with trastuzumab memAb. Meditope-enabled trastuzumab (I83E—aka v2) was mixed with 8-azido-5-diphenylalanine meditope at near stoichiometry concentrations. Alexafluor 647-DIBO was then added to the solution and allowed to react for 2 h. The mechanically interlocked trastuzumab memAb was then added to Her2 positive BT474 cells at concentrations of 1 nM, 10 nM and 100 nM. The cells were then analyzed by flow cytometry. As a control, long 5-diphenyl-meditope with Alexafluor647 (conjugated on the lysine) was added to the trastuzumab at saturating concentrations, added to the cells and analyzed in the same manner as the interlocked bond. As a second control, Alexafluor647 directly conjugated to memAb, added to the cells and analyzed in the same manner as the interlocked bond.
Figure 11:
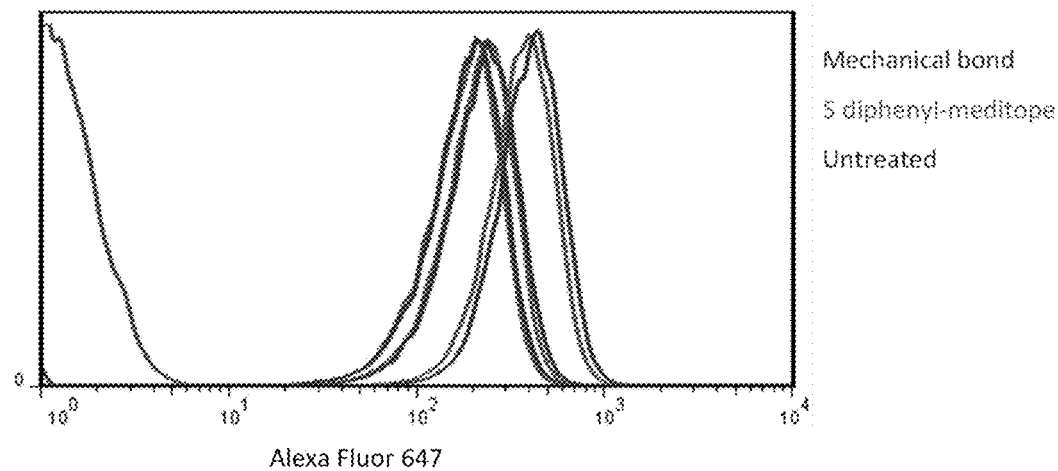
FIG. 11: Analytical Cytometry of anti-CD3 memAb. Meditope-enabled CD3 (based on UCHT1) was mixed with 8-azido-5-diphenylalanine meditope at near stoichiometry concentrations. Alexafluor 647-DIBO was then added to the solution and allowed to react for 2 h. The mechanically interlocked antiCD3 memAb was then added to purified human T cells at concentrations of 1 nM, 10 nM and 100 nM. The cells were then analyzed by flow cytometry. As a control, long 5-diphenyl-meditope with Alexafluor 647 (conjugated on the lysine) was added to the antiCD3 memAb at saturating concentrations, added to the cells and analyzed in the same manner as the interlocked bond.
Figure 12:
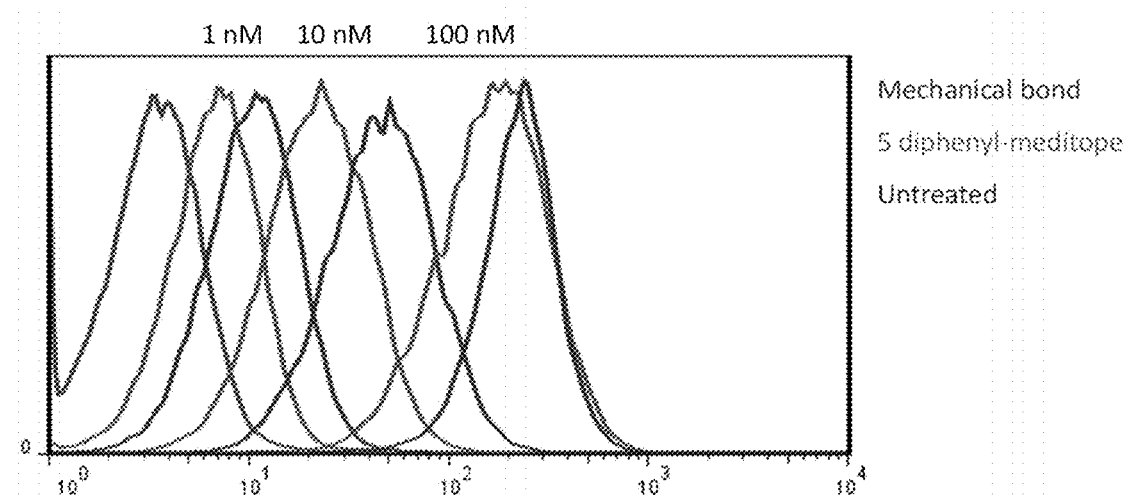
FIG. 12: Cell studies of meditope-enabled Pertuzumab IgG. The parental anti-Her2 (pertuzumab) mAb was meditope-enabled, expressed and purified. The 8-azido-5-diphenylalanine meditope was added to the anti-CD3 memAb at near stoichiometry concentrations. Alexafluor 647-DIBO was then added to the solution and allowed to react for 2 h. The mechanically interlocked pertuzumab memAb was then added to Her2 positive BT474 cells at concentrations of 1 nM, 10 nM and 100 nM. The cells were then analyzed flow cytometry. As a control, long 5-diphenyl-meditope with Alexafluor 647 (conjugated on the lysine) was added to the pertuzumab at saturating concentrations, added to the cells and analyzed in the same manner as the interlocked bond.
Figure 13:
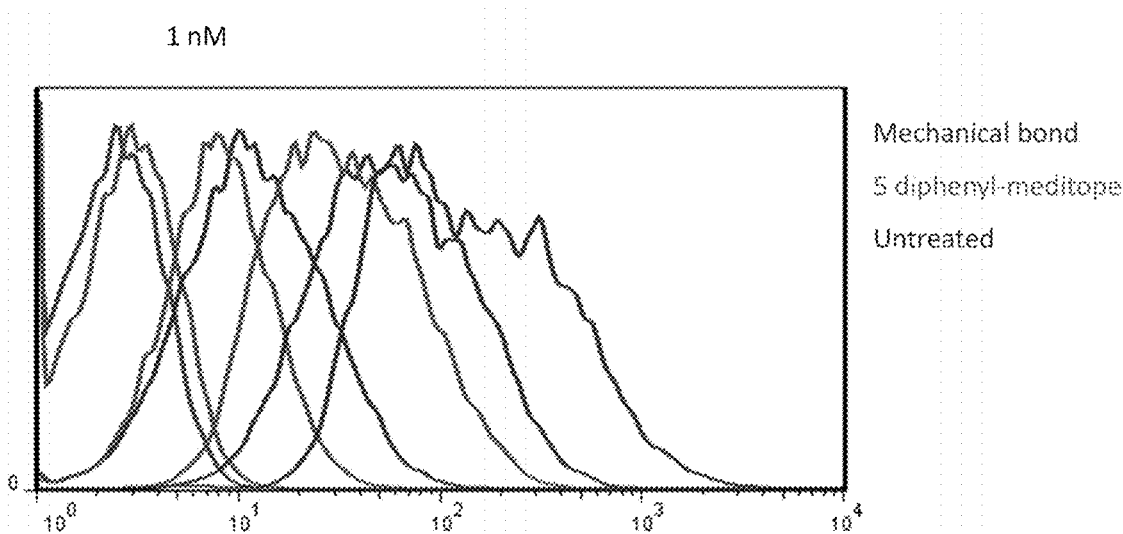
FIG. 13: Anti-CEA (M5A) memAb with the 13M (not I83E) on LS174T cells. Meditope-enabled anti-CEA encoding the original 13 mutation was mixed with 8-azido-5-diphenylalanine meditope at near stoichiometry concentrations. Alexafluor 647-DIBO was then added to the solution and allowed to react for 2 h. The mechanically interlocked anti-CEA memAb was then added to CEA positive LS174T cells at concentrations of 1 nM, 10 nM and 100 nM. The cells were then analyzed by flow cytometry. As a control, long 5-diphenyl-meditope with Alexafluor647 (conjugated on the lysine) was added to the anti-CEA memAb at saturating concentrations, added to the cells and analyzed in the same manner as the interlocked bond.
Figure 14:
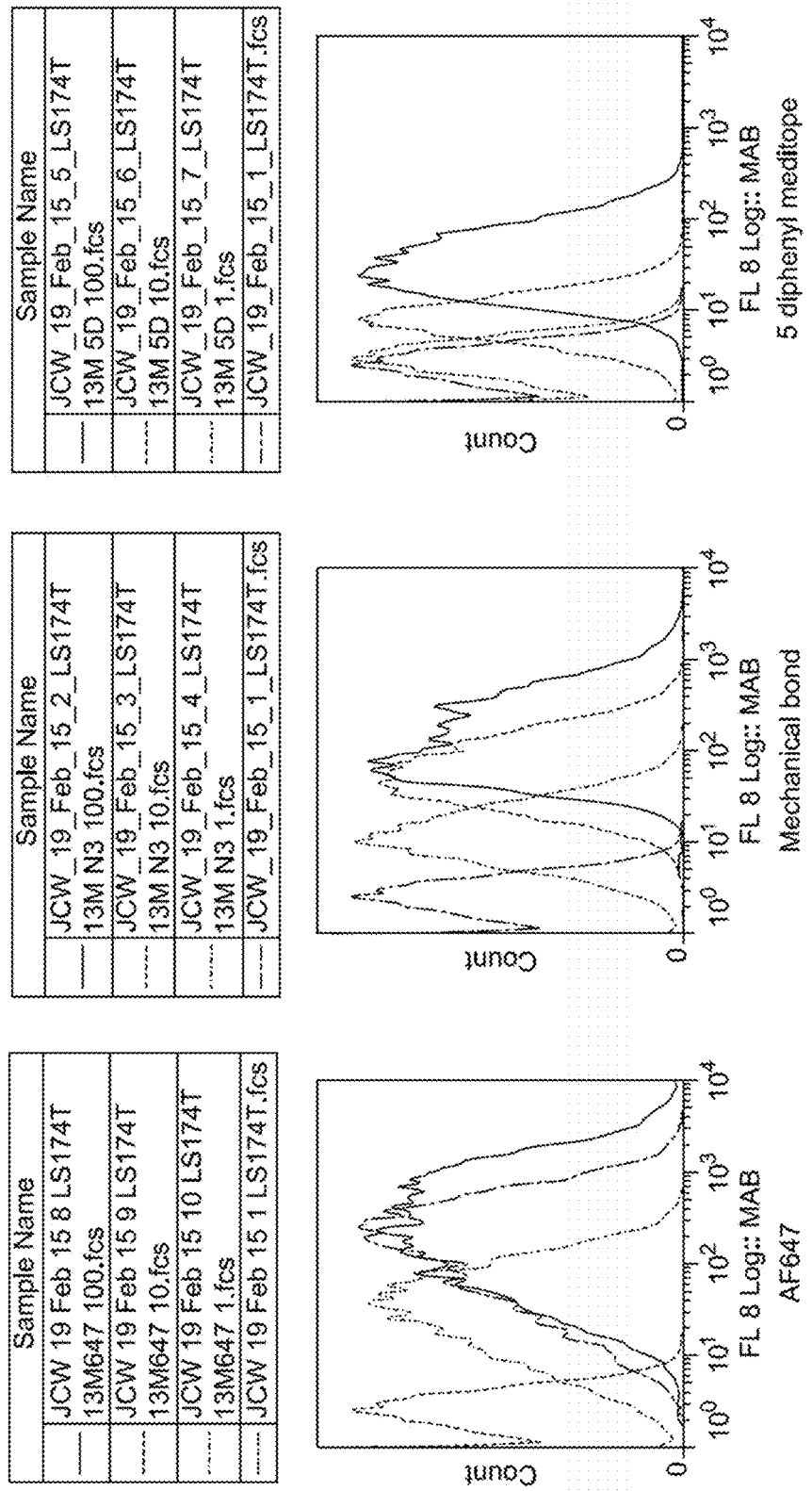
FIG. 14: M5A 13M's at a concentration of 1, 10, or 100 nM on LS174T cells. Meditope-enabled anti-CEA encoding the original 13 mutation was mixed with 8-azido-5-diphenylalanine meditope at near stoichiometry concentrations. Alexafluor 647-DIBO was then added to the solution and allowed to react for 2 h. The mechanically interlocked anti-CEA memAb was then added to CEA positive LS174 cells at concentrations of 1 nM, 10 nM and 100 nM. The cells where then analyzed flow cytometry. As a control, long 5-diphenyl-meditope with Alexafluor647 (conjugated on the lysine) was added to the anti-CEA memAb at saturating concentrations, added to the cells and analyzed in the same manner as the interlocked bond.
Figure 15A:
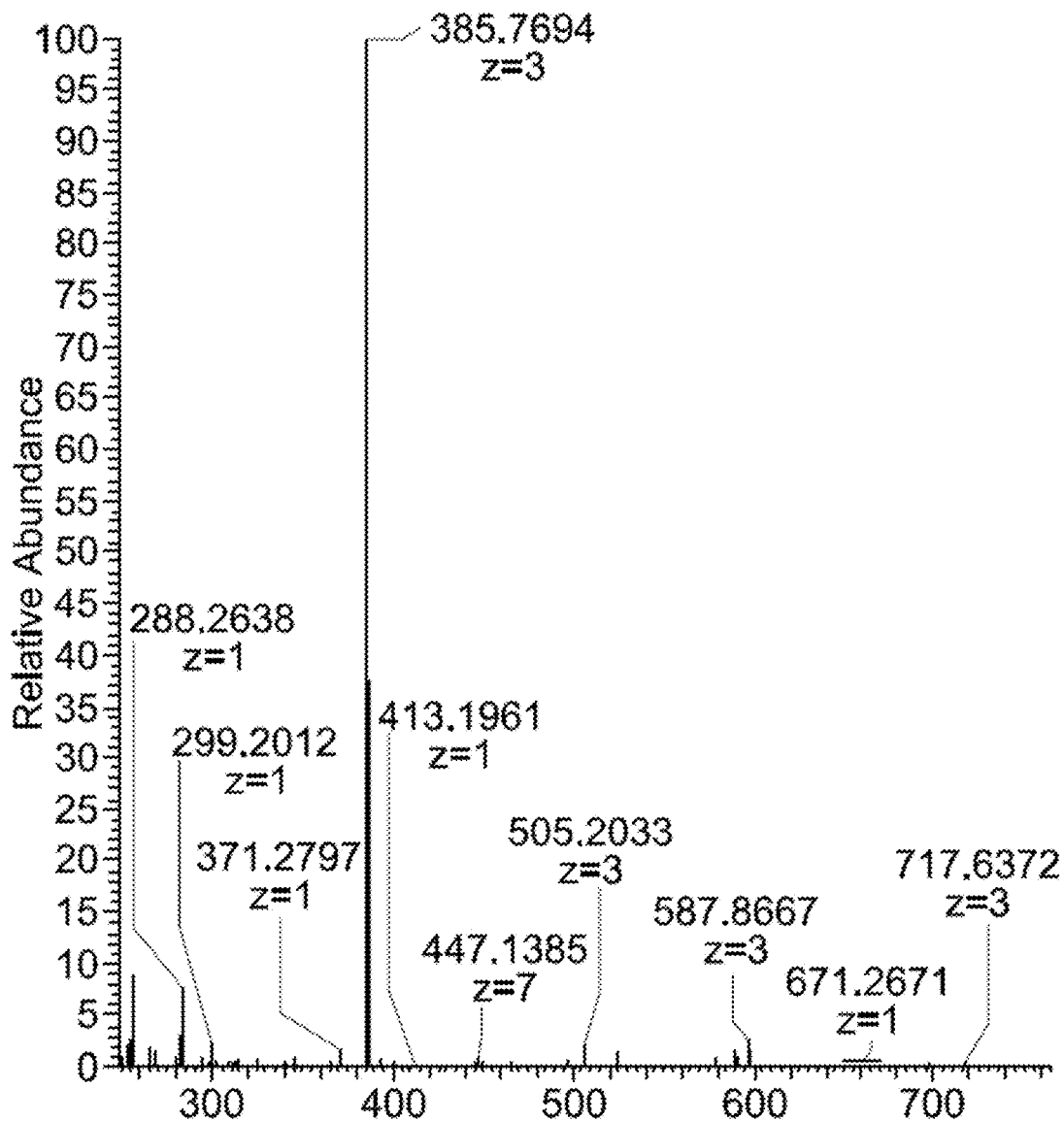
FIGS. 15A-15D: Mass spectrometry analysis of DIBO-AlexaFluor647.
Figure 15B:
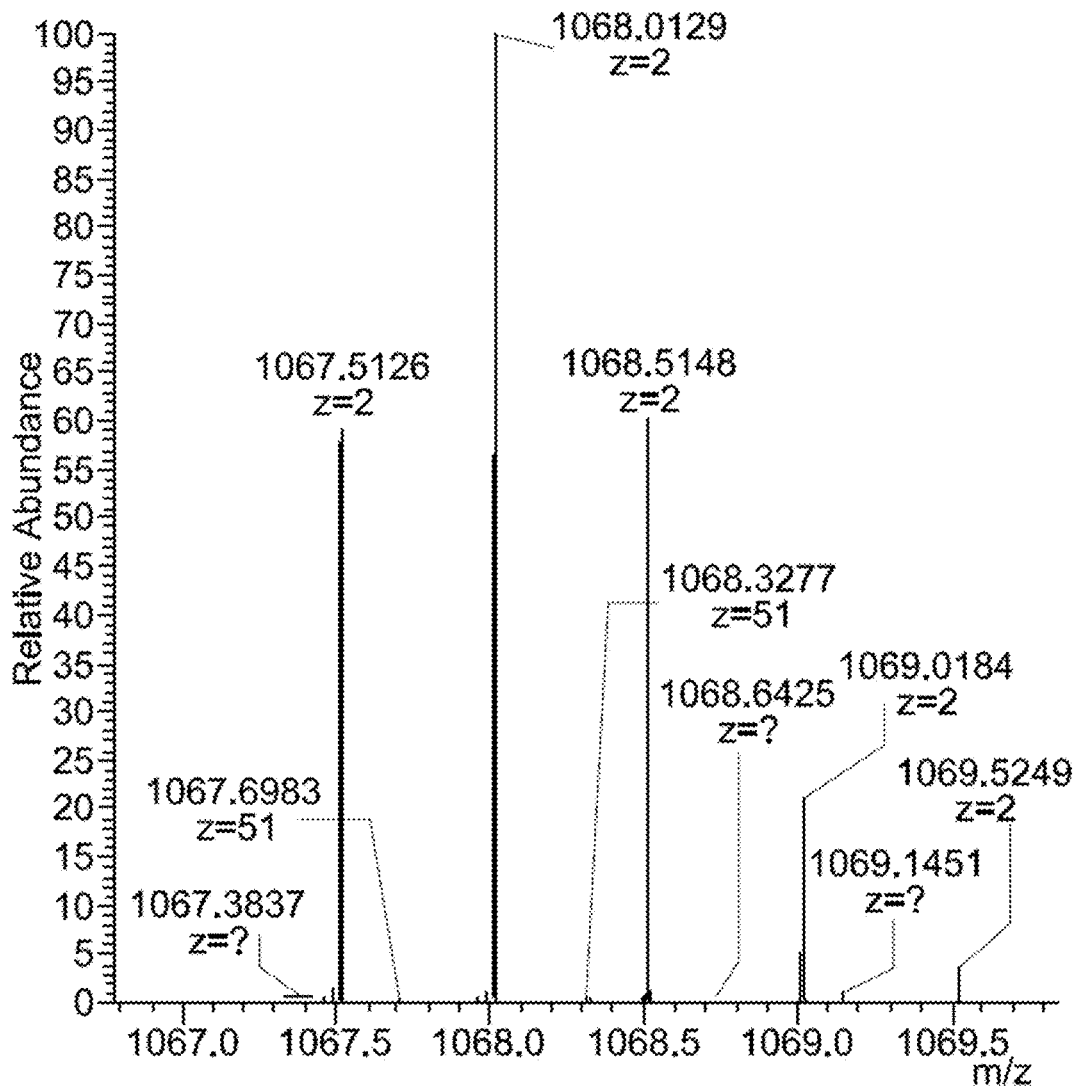
Figure 15C:
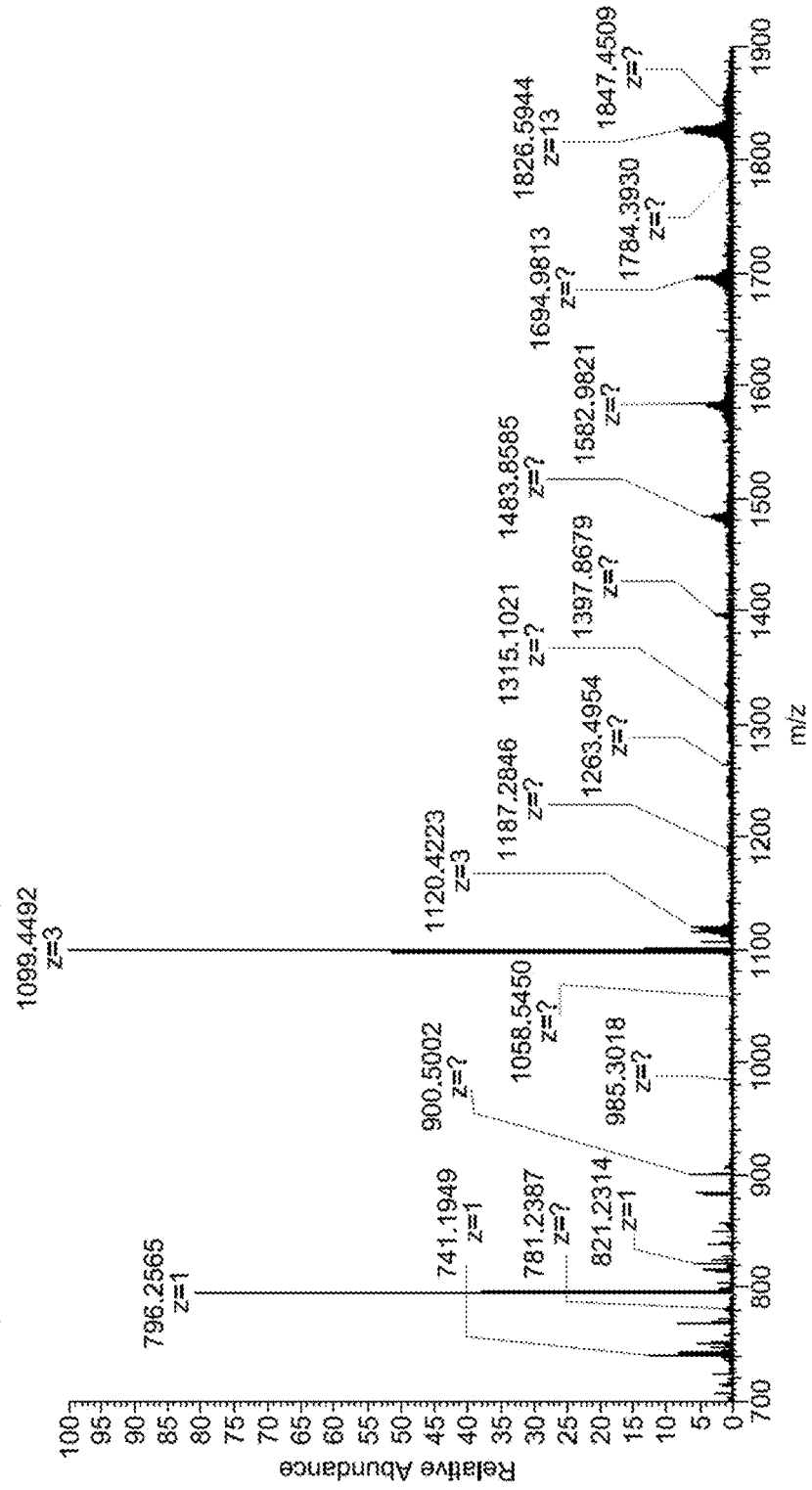
Figure 15D:
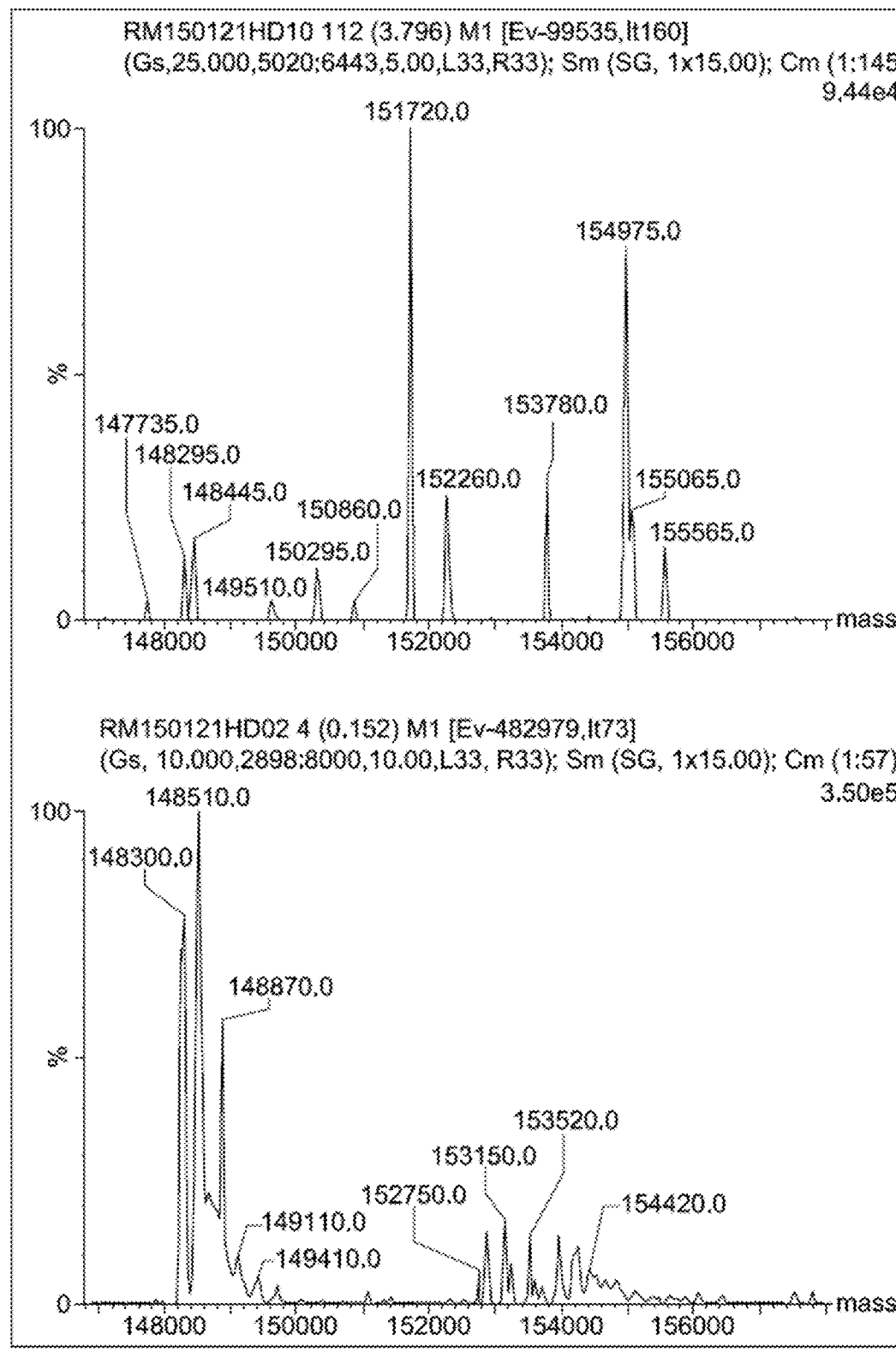
Figure 16:
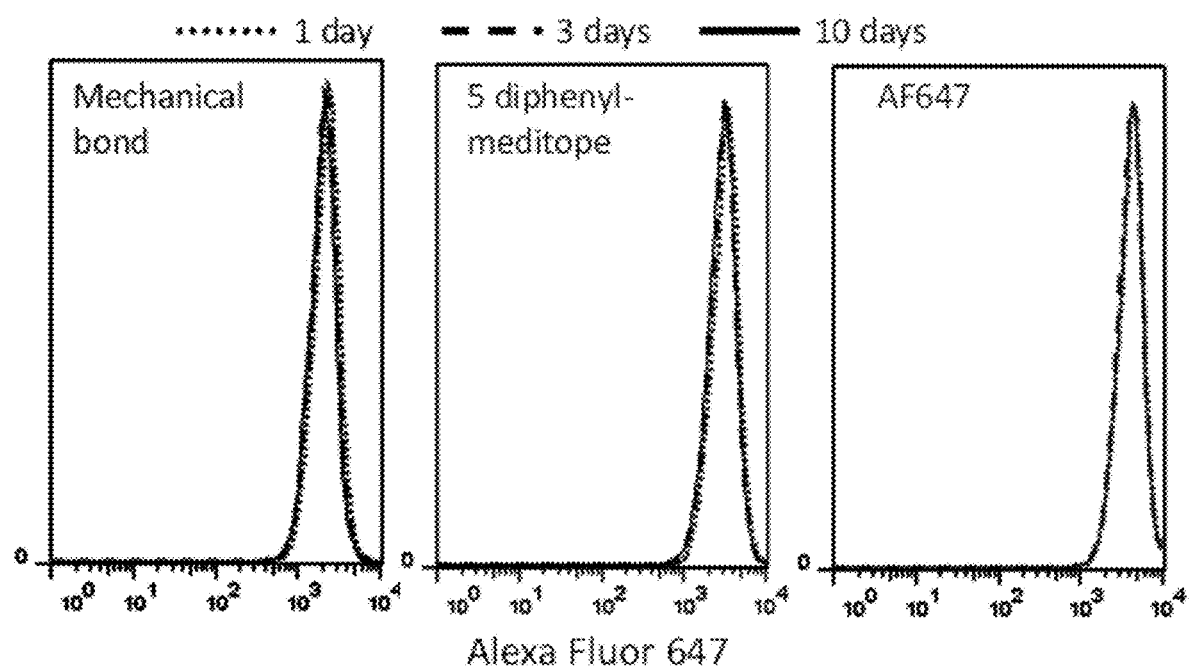
FIG. 16: Stability test. Interlocked meditope-memAb trastuzumab version 2, memAb trastuzumab version 2 saturated with Alexa Fluor 647-5 diphenyl meditope, or Alexa Fluor 647 conjugated memAb trastuzumab version 2 were incubated at 37° C. for 1, 3 or 10 days. The activity of the incubated samples was then tested by FACS. Trypsinized BT474 cells (~1 million cells per treatment) were mixed with 100 nM of each treated sample in 100 μL of 0.3% BSA-PBS for 30 min at room temperature, then the cells were washed with the BSA buffer twice and then analyzed on a CyAn™ ADP Analyzer (Beckman Coulter), and the data were analyzed with Flowjo software.
Figure 17A:
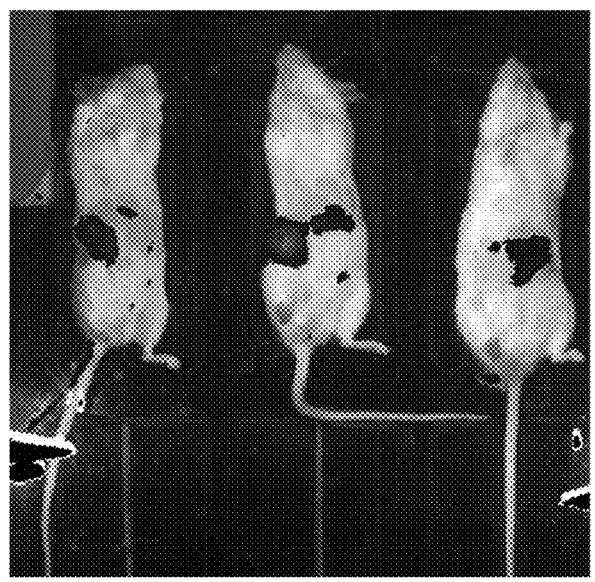
FIGS. 17A-17B: Imaging studies.
Figure 17B:
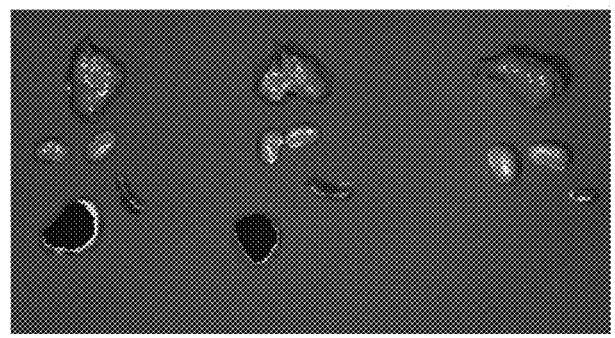
Figure 18:
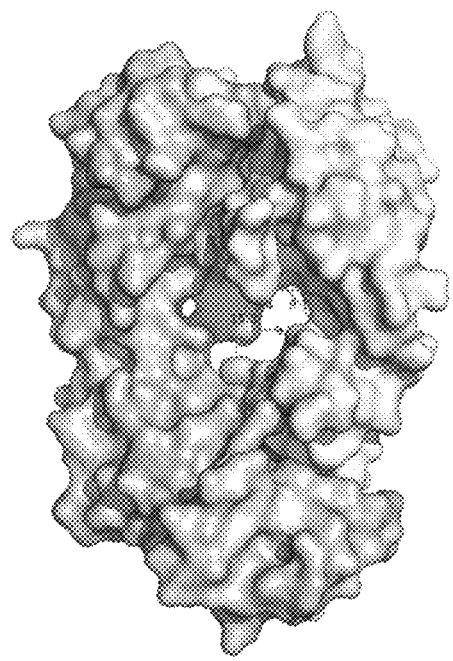
FIG. 18: Schematic representation of the Fab domain and the central cavity including the hole.

Using copper-free click chemistry, Alexa fluor 647 was locked on to trastuzumab, creating a non-covalent, mechanical bond (FIG. 3A, FIG. 4). SEC and mass spectrometry demonstrated the efficient formation of the interlocked complex. It was further demonstrated that the complex was stable beyond ten days at 37° C. (FIG. 16). Finally, it was demonstrated that an interlocked Alexafluor 647-Trastuzumab IgG1 was capable of imaging Her2-positive tumor xenographs in animal studies. In addition, the imaging dye remained in the tumor eight days post-administration (FIG. 17A, FIG. 17B). Collectively, these data indicate that it is possible to specifically and rapidly add functionality with covalent-like affinities to meditope-enabled mAbs. Based on these findings, it may be possible to generate rapidly 100s of unique mAbs drug conjugates, e.g., through the combination of derivatized meditopes and clickable "steric plugs." For instance, it may be possible to add ten unique cytotoxins to the 8-azido-meditope and ten different cytotoxins (or imaging agents) to the clickable steric plug, affording 100 unique combinations. The term "meditope" refers to the Fab binding moiety as described herein. Thus, in embodiments, a meditope is a peptidyl moiety.

Applicants previously discovered a unique peptide binding site within a hole created by the light and heavy chains (Proc Natl Acad Sci USA. 2013 Oct. 22; 110(43):17456-61; Identification and grafting of a unique peptide-binding site in the Fab framework of monoclonal antibodies. Donaldson JM1, Zer C, Avery K N, Bzymek K P, Home D A, Williams J C). Applicants showed that the residues that line this site were unique to cetuximab and not present in human mAbs. Applicants demonstrated that this site could be grafted on trastuzumab, a human mAb used to treat Her2+ cancer. By diffraction and binding studies Applicants showed that the grafting of this site did not perturb the structure and that the effect on antigen binding was indistinguishable from the parental mAb. As such, this site could be used as unique receptor, not only to potentially attach cargo, but also for emerging therapeutic techniques such as pre-targeted imaging.

Applicants observed in the structure of the meditope complexes that the side chain residues, Arg8 and Ser6, are partially accessible from the other side of the Fab hole. This accessibility provided the opportunity to incorporate a non-natural amino acid at either position in the meditope such that the side chain would extend through the hole, exposing a reactive group to the other side and enabling us to chemically couple a steric group to the modified meditope. A mechanical bond was generated to prevent dissociation (Top Curr Chem. 2012; 323:19-72; The mechanical bond: a work of art. Bruns C J, Stoddart J F). To do this, the affinity and the lifetime of the original meditope-Fab complex, $K_D \cong 1000$ nM and $\tau_{1/2} \cong 16$ sec (37° C.) were modified to ensure the Fab would be saturated and that reaction between the modified meditope and steric locking group occurs as part of the complex.

The affinity could be improved through modifications to the meditope, the Fab or both. First, a number of unnatural amino acids were introduced at various positions within the meditope. This included the introduction of branched amino acids, halogens into the side chains and D-amino acids to increase the buried surface area and introduce new hydrogen bonds (supplemental). Through these extensive structure-activity studies, it was observed that the substitution of Leu5 with diphenylalanine significantly increased the affinity of the meditope to meditope-enabled Trastuzumab Fab. At physiological temperatures (37° C.), SPR measurements show the affinity improves from 1000 nM to 41 nM, but with a short half-life, $\tau_{1/2} \cong 60$ sec. The crystal structure of this complex, refined to 2.55 Å with $R/R_{Free}$ of 17.2/21.9, indicates that the phenyl rings of the diphenylalanine straddle Leu115, increasing the buried surface area by 112 Å$^2$, from 883 Å$^2$ to 995 Å$^2$. No other significant changes in the structure were observed in the meditope or the Fab (0.68 Å compare to apo structure).

Next, the Fab domain was altered. Based on the original structure of the complex, an unusual rotamer in Arg9 of the meditope was observed, placing the guanidinium group in a partially buried cavity. Applicants hypothesized that the introduction of a negative charge in this cavity would result in a favorable buried charged-charged interaction. Thus, the mutation was generated, the modified meditope-enabled mAb was generated, the Fab isolated, and the affinity measured. At 37° C., SPR measurements using the original indicated a marked improvement affinity, from 1000 nM to 38 nM. Moreover, the off-rate appreciably decreased, $K_{off}=2.5\times10^{-3}$ s$^{-1}$ with a longer half-life, $\tau_{1/2} \cong 280$ sec. Diffraction studies of the original meditope bound to I83E Fab (refined to 1.78 Å with $R/R_{Free}$ of 15.9/19.7%) verified the formation of a favorable bond. The carboxyl of Glu83 in the Fab to NH1 of Arg8 of the meditope is 2.8 Å. As before, there were no significant changes in the complex, outside the point mutant.

Given the individual improvements, the affinity was measured and the crystal structure of the 5 diphenyl meditope with the E83 substituted trastuzumab Fab was solved. The SPR studies, again at 37° C., indicate that the combination binds tightly ($K_D$=0.86 nM) with a long lifetime, $t_{1/2} \cong 2400$ sec. In fact, the combination is additive or synergistic (Proc Natl Acad Sci USA. 1981 July; 78(7):4046-50. On the attribution and additivity of binding energies. Jencks W P). The increase in affinity is ~1160 fold (1000 nM/0.86 nM) where the individual increase in affinity is ~25 fold for each (1000 nM/40 nM), or 625 fold if multiplied. As before, the structure of the complex, refined at 1.81 Å with $R/R_{Free}$ of 16.3/19.1%, reflects no major differences to original or other substitution structures.

A reactive group was threaded through the Fab hole to create the mechanical bond, focusing on the guanidinium group of Arg8. Initially, it was attempted to add thiol which also included the replacement of cysteines at positions 1 and 12 used to cyclize the meditope. Click chemistry was also considered. Based on the structural data, an azide, spaced by two ethylene glycols, was introduced through zz chemistry. SPR studies indicated that the 8-azido-5-diphenyl meditope bound to the E83 meditope-enabled trastuzumab Fab with similar affinity, $K_D$=2.1 nM, but a long lifetime, $\tau_{1/2}\cong5000$ sec. To form the mechanical bond, the 8-azido-5-diphenyl meditope was mixed with the E83-modified trastuzumab Fab at a 1:1 stoichiometry and copper-free click chemistry was used to lock on the meditope with Alexafluor647-DIBO, a fluorescently labeled, strained alkyne. Using size exclusion chromatography (SEC), the co-elution of dye and the Fab was observed, indicating the formation of a mechanical bond. Mass spectrometry provided further evidence that the mechanical bond was formed. To differentiate the locked-on meditope-Fab complex from unreacted Fab by SEC, the Alexafluor647-DIBO was replaced with a 30 kDal PEG-DIBO. The two species were readily separated. By SPR it was demonstrated that the 30 kDal PEG locked meditope-Fab bound antigen with similar affinities as the parental Fab.

To determine whether the locked-on meditope-mAb could be used for delivery in a biological system, animal imaging studies were performed. First, two additional antibodies were meditope-enabled, an anti-CEA mAb (M5A) and an anti-CD3 mAb (UCHT1). As before, the formation of a mechanical bond using Alexafluor647-DIBO for both these meditope-enabled mAbs was demonstrated. Next, it was shown by analytical cytometry that the interlocked Alexafluor647-meditope-mAbs bound cells lines expressing their respective antigens. It was also demonstrated, in the presence of excess 5-diphenyl meditope, that the interlocked Alexafluor647-meditope-trastuzumab mAb complex remained intact over 10 days at 37° C. Finally, the interlocked Alexafluor647-meditope-trastuzumab mAb was introduced into NGS mice harboring BT474 xenograft tumors by tail vein injection. The animals were imaged 24 and 48 hours after injection, indicating that the Alexafluor647-meditope-trastuzumab mAb complex was predominantly located in the tumor and to a lesser extent in the liver. The organs were harvested 8 day s later and imaged. Strong fluorescent signaling was observed in the tumor. No signal was observed from the liver, kidneys, or spleen.

The structural insights of the meditope-Fab interaction were used to significantly enhance the affinity and lifetime of the interaction, allowing the threading of an azido group through a hole in the Fab and to create a mechanical bond through click chemistry. It was shown that the interlocked complex was stable and that antigen binding was not affected. Utility of this interaction was demonstrated by forming a mechanical bond with Alexafluor 647 and imaging tumor xenografts in animals. It was also shown that other moieties including PEG were interlocked. Collectively, these studies indicate that it is possible to "snap" on functionality to Fabs, opening up the possibility of rapidly creating unique combinations of mAbs by mixing-and-matching meditopes and locking moieties bearing an array of cytotoxins, biologics, and imaging agents.

Example 2

Creation of Two Interlocked Drug Conjugates

Auristatin and mertansine will be individually conjugated to the free lysine of an 8-azido-meditope, the conjugates will be interlocked onto meditope-enabled trastuzumab, and cell growth inhibition/death of the interlocked cytotoxins using BT474 and SKBR3 cell lines will be characterized. The cell growth inhibition will be directly compared to T-DM1 (trastuzumab emtansine). Next, tumor growth inhibition in animals will be tested.

Creation of Interlocked DOTA for Imaging and Radioimmunotherapy.

DOTA will be directly conjugated on to DIBO (dibenzocyclooctyne) and the DOTA-DIBO will be interlocked onto meditope-enabled anti-CEA mAb through the 8-azido-meditope. The DOTA will be charged with 64Cu and used to image LS-174T xenographs in immunodeficient mice or MC38.CEA syngenic tumors in C57B1.CEA transgenic mice. These images will be compared with anti-CEA directly conjugated to DOTA. Success here will allow the use of 67Cu or other radionuclides (90Y or 177Lu) for therapy. Additionally, the DOTA-DIBO will be combined with the auristatin/mertansine meditopes to image the delivery of cytotoxins in animal tumor xenografts. Moreover, this approach will open up the possibility of expanding the repertoire of cytotoxics, biologics, and siRNA that can be locked-on for the treatment of different forms of cancer.

Functionalized mAbs and mAb fragments to effectively kill tumors that are resistant to naked mAbs. The compositions and methods provided herein provide means to rapidly generate and identify combinations of cytotoxins or biologics to treat cancer more effectively. The opportunity to interlock cytotoxins, imaging agents, and other biologics rapidly and efficiently on to meditope-enabled mAbs represents a fundamental shift in the antibody modification field. Currently, the antibody-drug conjugates are typically generated by chemical modification through existing residues (cysteines, lysines or glycans) or require the introduction of an unnatural amino acid. The mAb of interest must be meditope-enabled and Applicants have shown using multiple mAbs that this process is straightforward and produces negligible or no effect on antigen affinity or mAb stability. Moreover, once enabled, the meditope site can be used to purify mAb (without recourse to protein A/L/G columns and high pHs used for elution). As noted, it can also be used for pre-targeted imaging or with multivalent meditopes to enhance internalization. Finally, the ability to conjugate two or more distinct moieties to the same mAb offers the unique ability to simultaneously target two unique pathways driving tumor progression, offering the possibility of rapidly identifying combinations of toxics that act synergistically.

Example 3

Figure 26:
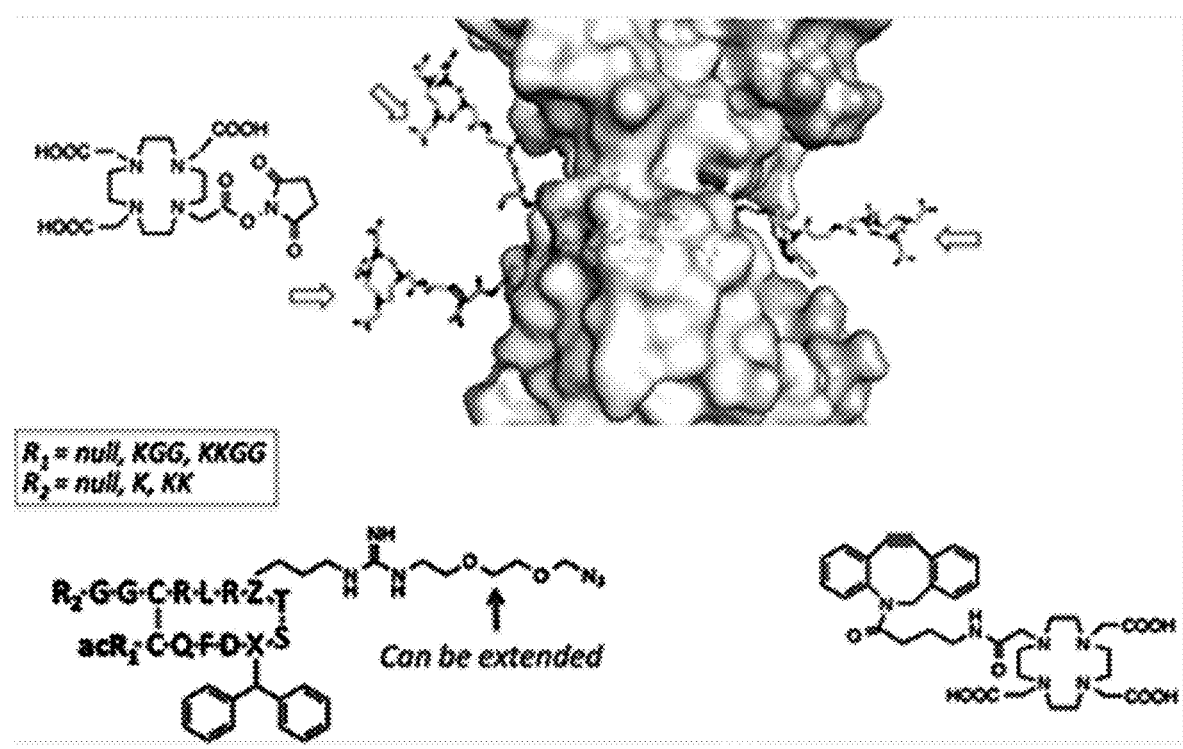
FIG. 26: Addition of DOTA and imaging agents to memAbs. Crystal structure of the 8-azido meditope and the azide bound to meditope-enabled Trastuzumab Fab (surface rendered). This azido-meditope has three ethylene glycol units between the guandinium group of Arg8. One, two or more lysines can be added to the N- and C-termini of the azido meditope. Modeled here is a lysine at the N-terminus and one at the C-terminus. Also modeled (and energy minimized) is the conjugated cyclooctyne, DBCO-DOTA (right side,). Before the adding to the memAb, DOTA will be added to the different lysine-azido meditope bolts or amine-cyclooctyne nut and purified to homogeneity. As the affinity of the 8-azido-meditope is greater than 10's of pM for the memAb at 25° C., the over 99% of the meditope binding sites on the memAb will be occupied at 1 μM concentration of each reactant.

Creation of meditopes for imaging: Applicants created two versions of the high-affinity azido-meditope. One version bridges the azido group to the guanidinium of the arginine with two ethylene glycol units and the other with three ethylene glycol units (FIG. 26). Applicants found that both are equally reactive using DIBO-Alexafluor647 with a yield of 73% (based on UV after purification using SEC). In further experiments, Applicants will mix the azido-meditope with the anti-CEA memAb at 1.1 to 1 stoichiometry where the memAb concentration is 1 µM. The AlexaFluor647 will be added in excess (1.2, 2, and 3 fold) in the different buffer conditions and at different temperatures. Applicants will monitor the efficiency of the reaction by comparing the protein concentration to the fluorescence signal. To deplete unreacted meditope from the anti-CEA memAb, the solution will be heated to 37° C. in the presence of beads conjugated with the high-affinity meditope. Unreacted meditope will dissociate and free memAb will be absorbed on the solid support. The solution will be sized to separate the remaining reactants and side products. Applicants will also use mass spectrometry to ensure the formation of the mechanical bond.

Applicants will also employ different strained analogs. These include DBCO, BARAC, BCN and other strained alkynes (Jewett, J. C., and Bertozzi, C. R. 2010. Cu-free click cycloaddition reactions in chemical biology. Chem Soc Rev 39:1272-1279; Gordon, C. G., Mackey, J. L., Jewett, J. C., Sletten, E. M., Houk, K. N., and Bertozzi, C. R. 2012. Reactivity of biarylazacyclooctynones in copper-free click chemistry. J Am Chem Soc 134:9199-9208). Several analogs are commercially available (Click Chemistry Tools). The others will be synthesized according to published literature (Jewett, J. C., and Bertozzi, C. R. 2010. Cu-free click cycloaddition reactions in chemical biology. Chem Soc Rev 39:1272-1279). Applicants will conjugate AlexaFluor647 to these strained cyclooctynes. Applicants will further add an additional ethylene glycol to "push" the azide further out into the solvent.

Applicants will synthesize additional high-affinity, azido-meditopes adding extra lysines at the N- and/or C-termini (and acetylate the N-terminus). DOTA or tetrazine groups will be added to the lysine amines through NHS chemistry. DOTA will be used for 64Cu labeling, and the tetrazine will be used for 18F labeling. Both DOTA and the tetrazine NHS esters are commercially available (Macrocyclics, Click Chemistry Tools). Applicants will further conjugate DOTA and methyltetrazine on to the optimal strained cyclooctyne group. This will allow to rapidly produce labeled antibodies with multiple radionuclides, either through DOTA or the tetrazine moiety. For instance, Applicants will add two DOTA moieties (e.g., one on each Fab arm), four DOTA moieties, six, eight or more DOTAs (see FIG. 26).

Example 4

Figure 27:
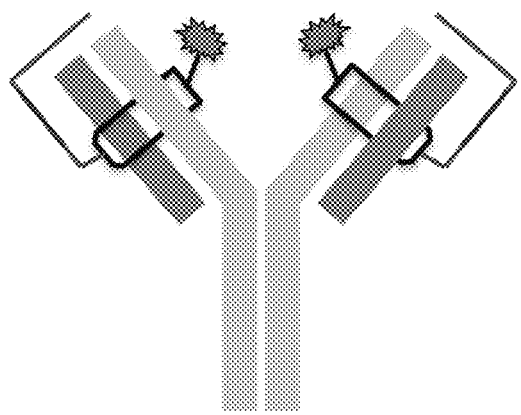
FIG. 27: meditope-enabled Mab including masking peptide moiety and therapeutic moeity (indicated by bubble).
Figure 28:
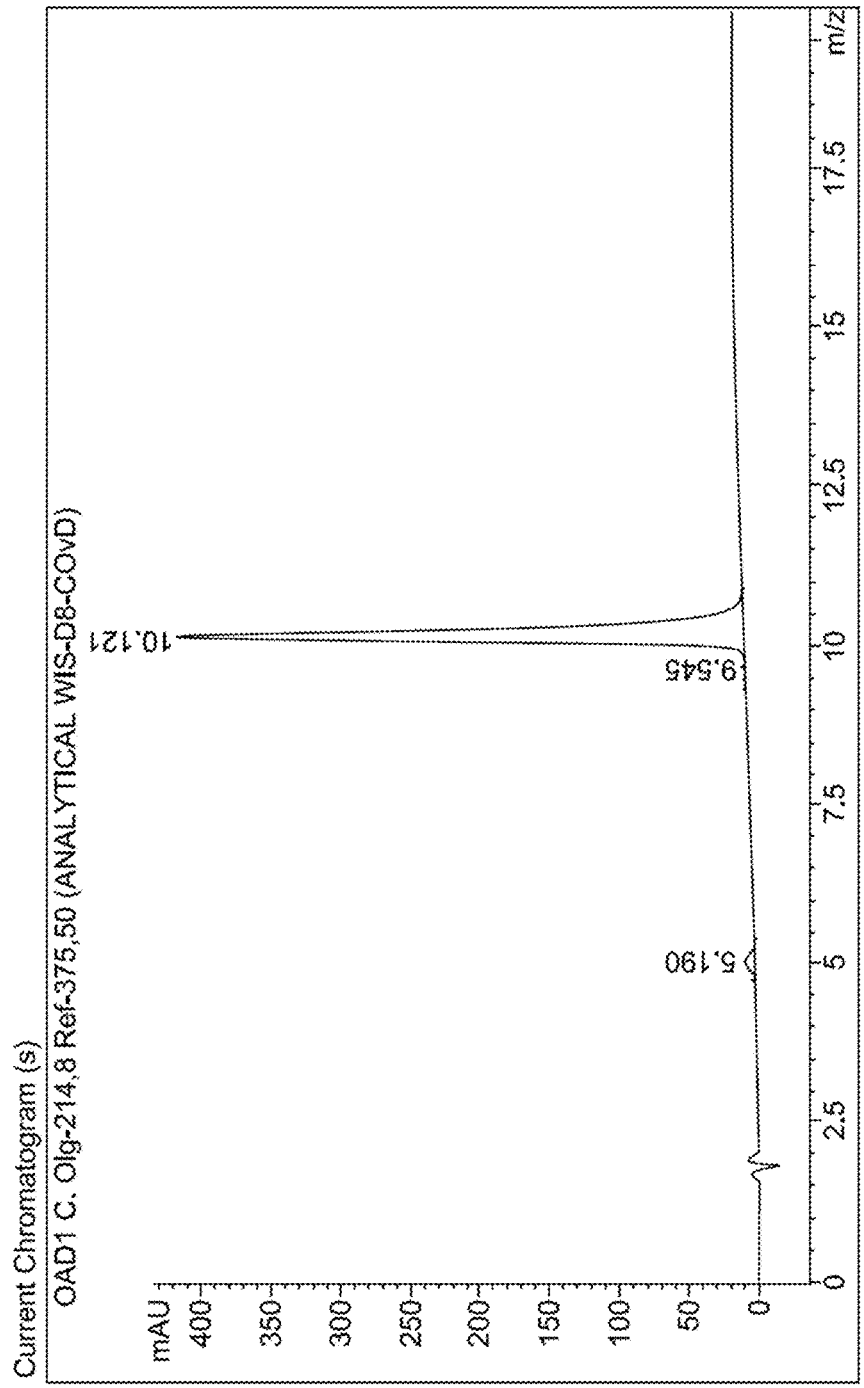
FIG. 28: HPLC of DBCO modified masking peptide (SEQ ID NO:20)
Figure 29:
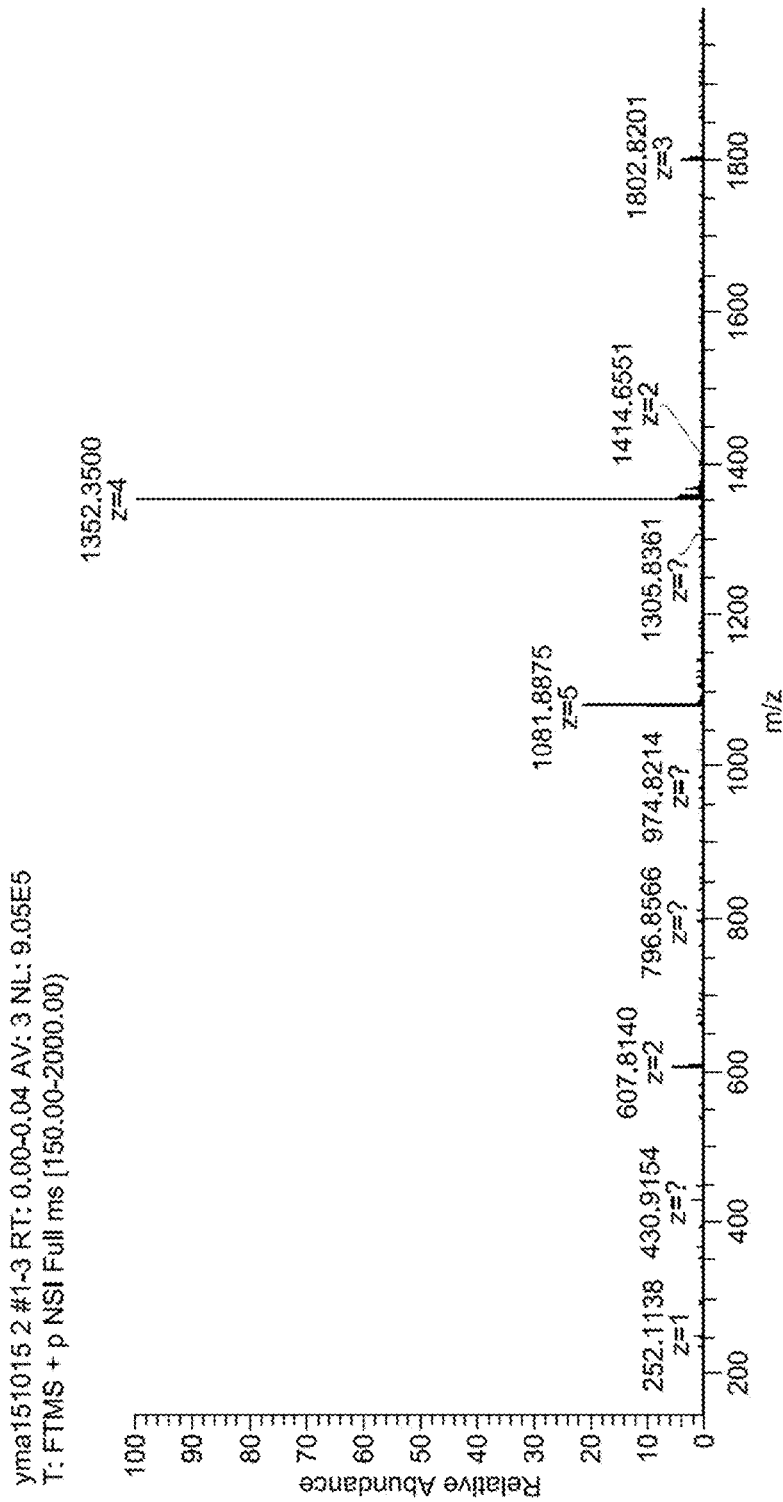
FIG. 29: Mass spec of masking-DIBO.

A number of monoclonal antibodies target tumor antigens and other disease related antigens that are expressed on healthy tissues, albeit at lower levels. Systemic administration of the antibodies can produce severe adverse side effects. For example, Cetuximab, an anti-EGFR mAb, produces can produce a sever skin rash, Trastuzumab can produce cardiomyopathies, Ipilimumab can produce colitis and hypophysitis, and in some cases, gives rise to sepsis which can be fatal, anti-PD1 mAbs can lead to type 1 diabetes. To reduce or eliminate these adverse side effects as well as improve the therapeutic window, Applicants create a tumor-activated mask using the mechanically interlocked meditope technology provided herein. Specifically, peptides can be readily identified that bind to the CDRs of a given mAb and sterically occlude antigen binding. While these peptides can be fused to the N-terminus of the light or heavy chain of the parental antibody, it is also possible to add the masking peptide to a meditope and mechanically interlock the meditope onto a meditope-enabled MAb. (FIG. 27).

EMBODIMENTS

Embodiment 1. A mechanically interlocked complex comprising a compound mechanically interlocked with a fragment antigen-binding (Fab) domain, said Fab domain comprising a hole within a central cavity lined by amino acid residues of the VH, VL, CH1, and CL regions of said Fab domain, wherein said central cavity comprises a non-CDR binding site, said compound comprising a Fab binding moiety attached to a steric hindering chemical moiety through a chemical linker, wherein said Fab binding moiety is bound to said non-CDR binding site, said chemical linker passes through said hole, and steric hindrance occurs between said steric hindering chemical moiety and amino acids lining said hole thereby mechanically interlocking said compound and said Fab.

Embodiment 2. The mechanically interlocked complex of embodiment 1, wherein said non-CDR binding site is a peptide binding site comprising framework region amino acid residues and said Fab binding moiety is a peptidyl moiety.

Embodiment 3. The mechanically interlocked complex of embodiment 2, wherein said peptidyl moiety binds to said peptide binding site with a $K_D$ of less than 100 nM.

Embodiment 4. The mechanically interlocked complex of embodiment 2, wherein said peptidyl moiety binds to said peptide binding site with a $K_D$ of less than 50 nM.

Embodiment 5. The mechanically interlocked complex of embodiment 2, wherein said peptidyl moiety binds to said peptide binding site with a $K_D$ of less than 10 nM.

Embodiment 6. The mechanically interlocked complex of embodiment 2, wherein said peptidyl moiety binds to said peptide binding site with a $K_D$ of less than 1 nM.

Embodiment 7. The mechanically interlocked complex of one of embodiments 2 to 6, wherein said peptidyl moiety binds to said peptide binding site with a $\tau_{1/2}$ of more than 200 seconds.

Embodiment 8. The mechanically interlocked complex of one of embodiments 2 to 6, wherein said peptidyl moiety binds to said peptide binding site with a $\tau_{1/2}$ of more than 500 seconds.

Embodiment 9. The mechanically interlocked complex of one of embodiments 2 to 6, wherein said peptidyl moiety binds to said peptide binding site with a $\tau_{1/2}$ of more than 1000 seconds.

Embodiment 10. The mechanically interlocked complex of one of embodiments 2 to 6, wherein said peptidyl moiety binds to said peptide binding site with a $\tau_{1/2}$ of more than 2000 seconds.

Embodiment 11. The mechanically interlocked complex of one of embodiments 1 to 10, wherein said compound and said Fab are bound together with a $\tau_{1/2}$ of more than 4000 seconds.

Embodiment 12. The mechanically interlocked complex of one of embodiments 1 to 10, wherein said compound and said Fab are bound together with a $\tau_{1/2}$ of more than 4500 seconds.

Embodiment 13. The mechanically interlocked complex of embodiment 1, wherein said compound comprises a therapeutic agent, a diagnostic agent, or a detectable agent.

Embodiment 14. The mechanically interlocked complex of embodiment 1, wherein said Fab binding moiety is conjugated to a therapeutic agent, a diagnostic agent, or a detectable agent.

Embodiment 15. The mechanically interlocked complex of one of embodiments 1 to 14, wherein said compound has the formula $R^1$-$L^1$-$R^2$ wherein, $R^1$ is said peptidyl moiety; $L^1$ is said chemical linker of about 5 Å to about 15 Å in length; and $R^2$ is said steric hindering chemical moiety wherein the longest bond length distance is at least 10 Å.

Embodiment 16. The mechanically interlocked complex of one of embodiments 1 to 15, wherein said chemical linker is a covalent linker.

Embodiment 17. The mechanically interlocked complex of one of embodiments 1 to 15, wherein said chemical linker is a substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene.

Embodiment 18. The mechanically interlocked complex of one of embodiments 1 to 15, wherein said chemical linker is a PEG linker.

Embodiment 19. The mechanically interlocked complex of embodiment 15, wherein $R^1$ is

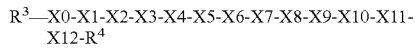

$$R^3\text{—X0-X1-X2-X3-X4-X5-X6-X7-X8-X9-X10-X11-X12-}R^4$$

wherein: X0 is Ser or null; X1 is Cys, Ser, Gly, β-alanine, diaminopropionic acid, β-azidoalanine, or null; X2 is Gln or null; X3 is Phe, Tyr, β,β'-diphenyl-Ala, His, Asp, 2-bromo-L-phenylalanine, 3-bromo-Lphenylalanine, 4-bromo-L-phenylalanine, Asn, Gln, a modified Phe, a hydratable carbonyl-containing residue, or a boronic acid-containing residue; X4 is Asp or Asn; X5 is Leu, β,β'-diphenyl-Ala, Phe, Trp, Tyr, a non-natural analog of phenylalanine, tryptophan, or tyrosine, a hydratable carbonyl-containing residue, or a boronic acid-containing residue; X6 is Ser or Cys; X7 is Thr, Ser or Cys; X8 is an amino acid comprising a side chain of the formula $-L^{1,4}\text{-}L^1\text{-}R^2$, wherein $L^{1,4}$ is substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene; X9 is Arg or Ala; X10 is Leu, Gln, Glu, β,β'-diphenyl-Ala, Phe, Trp, Tyr; a non-natural analog of phenylalanine, tryptophan, or tyrosine, a hydratable carbonyl-containing residue, or a boronic acid-containing residue; X11 is Lys or Arg; X12 is Cys, Gly, 7-aminoheptanoic acid, β-alanine, diaminopropionic acid, propargylglycine, isoaspartic acid, or null, $R^3$ and $R^4$ are independently null, $-L^2\text{-}R^5$ or an amino acid peptide sequence optionally substituted with $-L^2\text{-}R^5$, wherein $L^2$ is a covalent or non-covalent linker and $R^5$ is a therapeutic agent, a diagnostic agent, or a detectable agent; and wherein X1 and X12 are optionally joined together to form a cyclic peptidyl moiety.

Embodiment 20. The mechanically interlocked complex of embodiment 19, wherein X1 and X2 are Cys and are joined together through a disulfide bond to form a cyclic peptidyl moiety.

Embodiment 21. The mechanically interlocked complex of embodiment 19, wherein X0 is null.

Embodiment 22. The mechanically interlocked complex of embodiment 19, wherein X2 is Gln.

Embodiment 23. The mechanically interlocked complex of embodiment 19, wherein X5 is β,β'-diphenyl-Ala.

Embodiment 24. The mechanically interlocked complex of embodiment 19, wherein $L^{1,4}$ is —(CH$_2$)$_3$—NH(N)—NH—.

Embodiment 25. The mechanically interlocked complex of embodiment 19, wherein $R^3$ and $R^4$ are independently null, $-L^2\text{-}R^5$ or a 1 to 100 amino acid peptide sequence optionally substituted with $-L^2\text{-}R^5$, wherein $L^2$ is a covalent or non-covalent linker and $R^5$ is a therapeutic agent, a diagnostic agent, or a detectable agent.

Embodiment 26. The mechanically interlocked complex of embodiment 19, wherein $R^3$ is $-L^2\text{-}R^5$ or an amino acid peptide sequence optionally substituted with $-L^2\text{-}R^5$, and $R^4$ is null.

Embodiment 27. The mechanically interlocked complex of embodiment 19, wherein $R^3$ is a three amino acid peptide sequence optionally substituted with $-L^2\text{-}R^5$.

Embodiment 28. The mechanically interlocked complex of embodiment 19, wherein $R^3$ is Lys-Gly-Gly-optionally substituted with $-L^2\text{-}R^5$.

Embodiment 29. The mechanically interlocked complex of one of embodiments 1 to 28, wherein the non-CDR binding site is formed by amino acids at positions 8, 9, 10, 38, 39, 40, 4142, 43, 44, 45, 82, 83, 84, 85, 86, 87, 99, 100, 101, 102, 103, 104, 105, 142, 162, 163, 164, 165, 166, 167, 168, and 173 of the light chain and 6, 9, 38, 39, 40, 41, 42, 43, 44, 45, 84, 86, 87, 88, 89, 90, 91, 103, 104, 105, 106, 107, 108, 111, 110, 147, 150, 151, 152, 173, 174, 175, 176, 177, 185, 186, and 187 of the heavy chain of the Fab, according to Kabat numbering.

Embodiment 30. The mechanically interlocked complex of one of embodiments 1 to 29, wherein the Fab comprises a Glu at position 83, according to Kabat numbering.

Embodiment 31. The mechanically interlocked complex of one of embodiments 1 to 30, wherein the Fab comprises a Thr or Ser at position 40, according to Kabat numbering.

Embodiment 32. The mechanically interlocked complex of one of embodiments 1 to 31, wherein the Fab comprises an Asn at position 41, according to Kabat numbering.

Embodiment 33. The mechanically interlocked complex of one of embodiments 1 to 32, wherein the Fab comprises an Asp or Asn at position 85, according to Kabat numbering.

Embodiment 34. A method of binding an antigen, said method comprising contacting an antigen with said mechanically interlocked complex of one of embodiments 1 to 33 and allowing said Fab to bind said antigen.

Embodiment 35. A compound having the formula:

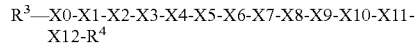

$$R^3\text{—X0-X1-X2-X3-X4-X5-X6-X7-X8-X9-X10-X11-X12-}R^4$$

wherein: X0 is Ser or null; X1 is Cys, Ser, Gly, β-alanine, diaminopropionic acid, β-azidoalanine, or null; X2 is Gln or null; X3 is Phe, Tyr, β,β'-diphenyl-Ala, His, Asp, 2-bromo-L-phenylalanine, 3-bromo-Lphenylalanine, 4-bromo-L-phenylalanine, Asn, Gln, a modified Phe, a hydratable carbonyl-containing residue, or a boronic acid-containing residue; X4 is Asp or Asn; X5 is Leu; β,β'-diphenyl-Ala; Phe; Trp; Tyr; a non-natural analog of phenylalanine, tryptophan, or tyrosine; a hydratable carbonyl-containing residue; or a boronic acid-containing residue; X6 is Ser or Cys; X7 is Thr, Ser or Cys; X8 is an amino acid comprising a side chain of the formula $-L^{1,4}\text{-}L^1\text{-}R^2$, wherein $L^{1,4}$ is substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene; X9 is Arg or Ala; X10 is Leu; Gln; Glu; β,β'-diphenyl-Ala; Phe; Trp; Tyr; a non-natural analog of phenylalanine, tryptophan, or tyrosine; a hydratable carbonyl-containing residue; or a boronic acid-containing residue; X11 is Lys or Arg; X12 is Cys, Gly, 7-aminoheptanoic acid, β-alanine, diaminopropionic acid, propargylglycine, isoaspartic acid, or null, $L^1$ is a chemical linker of about 5 Å to about 15 Å or more in length; $R^2$ is a steric hindering chemical moiety wherein the longest bond length distance is at least 8 Å; $R^3$ and $R^4$ are independently null, $-L^2\text{-}R^5$ or an amino acid peptide sequence optionally substituted with $-L^2\text{-}R^5$, wherein $L^2$ is a covalent or non-covalent linker and $R^5$ is a therapeutic agent, a diagnostic agent, or a detectable agent; and wherein X1 and X12 are optionally joined together to form a cyclic peptidyl moiety.

Embodiment 36. A compound having the formula:

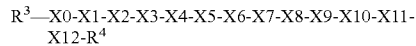

$$R^3\text{—X0-X1-X2-X3-X4-X5-X6-X7-X8-X9-X10-X11-X12-}R^4$$

wherein: X0 is Ser or null; X1 is Cys, Ser, Gly, β-alanine, diaminopropionic acid, β-azidoalanine, or null; X2 is Gln or null; X3 is Phe, Tyr, β,β'-diphenyl-Ala, His, Asp, 2-bromo-L-phenylalanine, 3-bromo-Lphenylalanine, 4-bromo-L-phenylalanine, Asn, Gln, a modified Phe, a hydratable carbonyl-containing residue, or a boronic acid-containing residue; X4 is Asp or Asn; X5 is Leu; β,β'-diphenyl-Ala; Phe; Trp; Tyr;

a non-natural analog of phenylalanine, tryptophan, or tyrosine; a hydratable carbonyl-containing residue; or a boronic acid-containing residue; X6 is Ser or Cys; X7 is Thr, Ser or Cys; X8 is an amino acid comprising a side chain of the formula $-L^{1A}-L^1-R^6$, wherein L1A is substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene; X9 is Arg or Ala; X10 is Leu; Gln; Glu; β,β'-diphenyl-Ala; Phe; Trp; Tyr; a non-natural analog of phenylalanine, tryptophan, or tyrosine; a hydratable carbonyl-containing residue; or a boronic acid-containing residue; X11 is Lys or Arg; and X12 is Cys, Gly, 7-aminoheptanoic acid, β-alanine, diaminopropionic acid, propargylglycine, isoaspartic acid, or null, $R^3$ and $R^4$ are independently null, $-L^2-R^5$ or an amino acid peptide sequence optionally substituted with $-L^2-R^5$, wherein $L^2$ is a covalent or non-covalent linker and $R^5$ is a therapeutic agent, a diagnostic agent, or a detectable agent; $R^6$ is a click chemistry reactive functional group; and wherein X1 and X12 are optionally joined together to form a cyclic peptidyl moiety.

Embodiment 37. The compound of embodiment 36, wherein $R^6$ is —$N_3$ or —SH.

Embodiment 38. The compound of embodiment 36, wherein said compound is bound to a fragment antigen-binding (Fab) domain.

Embodiment 39. The compound of embodiment 38, wherein said Fab domain comprises a hole within a central cavity lined by amino acid residues of the VH, VL, CH1, and CL regions of said Fab domain, wherein said central cavity comprises a non-CDR binding site, wherein said compound is bound to said non-CDR binding site.

Embodiment 40. A method of forming a mechanically interlocked complex, said method comprising: contacting said compound of embodiment 39 with a steric hindering chemical moiety comprising a complementary click chemistry reactive functional group; allowing said complementary click chemistry reactive functional group to react with said click chemistry reactive functional thereby forming a chemical linker between said steric hindering chemical moiety and said compound, wherein said chemical linker passes through said hole and steric hindrance occurs between said steric hindering chemical moiety and amino acids lining said hole thereby mechanically interlocking said compound and said Fab.

Embodiment 41. A method of forming a mechanically interlocked complex, said method comprising: contacting a compound with a steric hindering chemical moiety, said steric hindering chemical moiety comprising a complementary click chemistry reactive functional group and said compound comprising a Fab binding moiety attached to a click chemistry reactive group, wherein said Fab binding moiety is bound to a non-CDR binding site of a Fab domain, said Fab domain comprising a hole within a central cavity lined by amino acid residues of the VH, VL, CH1, and CL regions of said Fab domain, wherein said central cavity comprises said non-CDR binding site; allowing said complementary click chemistry reactive functional group to react with said click chemistry reactive functional group thereby forming a conjugate comprising a steric hindering chemical moiety linked through a chemical linker to said Fab binding moiety, wherein said chemical linker passes through said hole and steric hindrance occurs between said steric hindering chemical moiety and amino acids lining said hole thereby mechanically interlocking said compound and said Fab.

What is claimed is:

1. A mechanically interlocked complex comprising a compound mechanically interlocked with a fragment antigen-binding (Fab) domain, said Fab domain comprising a hole within a central cavity lined by amino acid residues of the VH, VL, CH1, and CL regions of said Fab domain, wherein said central cavity comprises a non-CDR binding site;

wherein said amino acid residues of the VL region are a threonine at position 40, an asparagine at position 41, and an aspartate at position 85, according to Kabat numbering, and wherein said amino acid residues of the VH region are a seine or proline at position 40 and an isoleucine, tyrosine, methionine, phenylalanine, or a tryptophan at position 89, according to Kabat numbering;

said compound comprising a Fab binding moiety attached to a steric hindering chemical moiety through a chemical linker, wherein said Fab binding moiety is bound to said non-CDR binding site, said chemical linker passes through said hole, and steric hindrance occurs between said steric hindering chemical moiety and amino acids lining said hole thereby mechanically interlocking said compound and said Fab;

wherein said compound has the formula:

$R^1-L^1-R^2$ wherein $R^1$ is
$R^3$—X0-X1-X2-X3-X4-X5-X6-X7-X8-X9-X10-X11-X12-$R^4$
wherein:
X0 is Ser or null;
X1 is Cys, Ser, Gly, β-alanine, diaminopropionic acid, β-azidoalanine, or null;
X2 is Gln or null;
X3 is Phe, Tyr, β,β'-diphenyl-Ala, His, Asp, 2-bromo-L-phenylalanine, 3-bromo-L-phenylalanine, 4-bromo-L-phenylalanine, Asn, Gln, a modified Phe, or a boronic acid-containing residue;
X4 is Asp or Asn;
X5 is Leu, β,β'-diphenyl-Ala, Phe, Trp, Tyr, tryptophan, or tyrosine, or a boronic acid-containing residue;
X6 is Ser or Cys;
X7 is Thr, Ser or Cys;
X8 is an amino acid comprising a side chain of the formula -$L^{14}$-$L^1$-$R^2$,
wherein $L^{14}$ is substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene;
wherein $L^1$ is said chemical linker of about 5 Å to about 15 Å in length; and
$R^2$ is said steric hindering chemical moiety wherein the longest bond length distance is at least 10 Å;
X9 is Arg or Ala;
X10 is Leu, Gln, Glu, β,β'-diphenyl-Ala, Phe, Trp, Tyr, tryptophan, or tyrosine, or a boronic acid-containing residue;
X11 is Lys or Arg;
X12 is Cys, Gly, 7-aminoheptanoic acid, β-alanine, diaminopropionic acid, propargylglycine, isoaspartic acid, or null,
$R^3$ and $R^4$ are independently null, -$L^2$-$R^5$ or an amino acid peptide sequence optionally substituted with -$L^2$-$R^5$, wherein $L^2$ is a covalent or non-covalent linker and $R^5$ is a therapeutic agent, a diagnostic agent, or a detectable agent; and
wherein X1 and X12 are optionally joined together to form a cyclic peptidyl moiety.

2. The mechanically interlocked complex of claim 1, wherein said non-CDR binding site is a peptide binding site comprising framework region amino acid residues and said Fab binding moiety is a peptidyl moiety.

3. The mechanically interlocked complex of claim 2, wherein said peptidyl moiety binds to said peptide binding site with a $K_D$ of less than 10 nM.

4. The mechanically interlocked complex of claim 2, wherein said peptidyl moiety binds to said peptide binding site with a $K_D$ of less than 1 nM.

5. The mechanically interlocked complex of claim 2, wherein said peptidyl moiety binds to said peptide binding site with a $\tau_{1/2}$ of more than 2000 seconds.

6. The mechanically interlocked complex of claim 1, wherein said compound and said Fab are bound together with a $\tau_{1/2}$ of more than 4500 seconds.

7. The mechanically interlocked complex of claim 1, wherein said chemical linker is a substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene.

8. The mechanically interlocked complex of claim 1, wherein $L^{14}$ is —$(CH_2)_3$—NH(N)—NH—.

9. The mechanically interlocked complex of claim 1, wherein $R^3$ and $R^4$ are independently null, -$L^2$-$R^5$ or a 1 to 100 amino acid peptide sequence optionally substituted with -$L^2$-$R^5$, wherein $L^2$ is a covalent or non-covalent linker and $R^5$ is a therapeutic agent, a diagnostic agent, or a detectable agent.

10. The mechanically interlocked complex of claim 1, wherein $R^3$ is a three amino acid peptide sequence optionally substituted with $-L^2-R^5$.

11. The mechanically interlocked complex of claim 1, wherein the non-CDR binding site is formed by amino acids at positions 8, 9, 10, 38, 39, 40, 41 42, 43, 44, 45, 82, 83, 84, 85, 86, 87, 99, 100, 101, 102, 103, 104, 105, 142, 162, 163, 164, 165, 166, 167, 168, and 173 of the light chain and 6, 9, 38, 39, 40, 41, 42, 43, 44, 45, 84, 86, 87, 88, 89, 90, 91, 103, 104, 105, 106, 107, 108, 111, 110, 147, 150, 151, 152, 173, 174, 175, 176, 177, 185, 186, and 187 of the heavy chain of the Fab, according to Kabat numbering.

12. A method of binding an antigen, said method comprising contacting an antigen with said mechanically interlocked complex of claim 1 and allowing said Fab to bind said antigen.

* * * * *

SEQUENCE LISTING

```
<160> NUMBER OF SEQ ID NOS: 20

<210> SEQ ID NO 1
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 1

Gln Gly Gln Ser Gly Gln Cys Ile Ser Pro Arg Gly Cys Pro Asp Gly
1               5                   10                  15

Pro Tyr Val Met Tyr
            20

<210> SEQ ID NO 2
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 2

Cys Glu Lys Trp Phe Arg Phe Met Cys
1               5

<210> SEQ ID NO 3
<211> LENGTH: 9
<212> TYPE: PRT
<213> ORGANISM: Artificial Sequence
```

```
<220> FEATURE:
<223> OTHER INFORMATION: Synthetic polypeptide

<400> SEQUENCE: 3

Cys Val Thr Gly Phe Glu Phe Leu Cys
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 4

Cys Ser Val Leu Pro Pro Phe Met Cys
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 5

Cys Ser Val Leu Leu Pro Phe Met Cys
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 6

Cys Trp Ser Pro Leu Pro Phe Met Cys
1               5

<210> SEQ ID NO 7
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 7

Cys Pro Arg Pro Leu Tyr Trp Leu Cys
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 8

Cys Phe Thr Pro Trp Pro Glu Ala Cys
1               5

<210> SEQ ID NO 9
<211> LENGTH: 9
<212> TYPE: PRT
<213> ORGANISM: Artificial Sequence
<220> FEATURE:
```

```
<223> OTHER INFORMATION: Synthetic polypeptide

<400> SEQUENCE: 9

Cys Phe His Ala Pro Trp Ala Pro Cys
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 10

Cys Asn Asn Tyr Lys Gly Gly Arg Cys
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 11

Cys Trp Pro Glu Trp Asp Leu Trp Cys
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 12

Cys Leu Pro Glu Ile Ser Phe Leu Cys
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 13

Cys Arg Ile Asp Glu Arg Leu Gln Cys
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 14

Cys Tyr Leu Glu Leu Met His Ser Cys
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic polypeptide
```

```
<400> SEQUENCE: 15

Cys Tyr Gly Leu Gly Phe Asn Phe Cys
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 16

Lys Ser Ala Asp Ala Ser Lys
1               5

<210> SEQ ID NO 17
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 17

Ser Ser Gly Thr Gly Gly Ser Gly Ser Gly Lys
1               5                   10

<210> SEQ ID NO 18
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 18

Ser Gly Arg Ser Asp Asn His Gly
1               5

<210> SEQ ID NO 19
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 19

Gly Ser Ser Gly Gly Ser Gly Gly Ser Gly Gly Ser Gly Leu
1               5                   10

<210> SEQ ID NO 20
<211> LENGTH: 54
<212> TYPE: PRT
<213> ORGANISM: Artificial Sequence
<220> FEATURE:
<223> OTHER INFORMATION: Synthetic polypeptide
```

```
<400> SEQUENCE: 20

Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
            20                  25                  30

Ser Gly Leu Ser Gly Arg Ser Asp Asn His Gly Ser Ser Gly Thr Gly
            35                  40                  45

Gly Ser Gly Ser Gly Lys
            50
```